US012569588B2

(12) United States Patent
Wu et al.

(10) Patent No.: US 12,569,588 B2
(45) Date of Patent: Mar. 10, 2026

(54) SELF-ASSEMBLING GRAPHENE OXIDE-PROTEIN MATRIX

(71) Applicant: UNIVERSITY OF NOTTINGHAM, Nottingham (GB)

(72) Inventors: Yuanhao Wu, London (GB); Wen Wang, London (GB); Alvaro Mata Chavarria, London (GB)

(73) Assignee: UNIVERSITY OF NOTTINGHAM, Nottingham (GB)

(*) Notice: Subject to any disclaimer, the term of this patent is extended or adjusted under 35 U.S.C. 154(b) by 974 days.

(21) Appl. No.: 17/277,341

(22) PCT Filed: Sep. 19, 2019

(86) PCT No.: PCT/EP2019/075264
§ 371 (c)(1),
(2) Date: Mar. 18, 2021

(87) PCT Pub. No.: WO2020/058456
PCT Pub. Date: Mar. 26, 2020

(65) Prior Publication Data
US 2021/0346570 A1    Nov. 11, 2021

(30) Foreign Application Priority Data
Sep. 19, 2018    (GB) ...................................... 1815285

(51) Int. Cl.
*A61L 27/08*        (2006.01)
*A61L 27/22*        (2006.01)
(Continued)

(52) U.S. Cl.
CPC ............. *A61L 27/08* (2013.01); *A61L 27/227* (2013.01); *A61L 27/3808* (2013.01);
(Continued)

(58) Field of Classification Search
CPC .... A61L 27/08; A61L 27/227; A61L 27/3808; A61L 27/507; A61L 2300/214;
(Continued)

(56) References Cited

FOREIGN PATENT DOCUMENTS

| | | |
|---|---|---|
| CN | 105268021 | 1/2016 |
| CN | 105903071 | 8/2016 |
| WO | 2014102547 | 7/2014 |

OTHER PUBLICATIONS

Qingdao Sandi Biotechnology Co Ltd, machine translation provided from FIT via PE2E of CN 105903071, 2016 (Year: 2016).*

(Continued)

*Primary Examiner* — Bethany P Barham
*Assistant Examiner* — Ayaan A Alam
(74) *Attorney, Agent, or Firm* — Riverside Law LLP

(57)                    ABSTRACT

The present invention relates to a stable self-assembling graphene oxide-protein matrix comprising a disordered protein (DP) and graphene oxide (GO), wherein the DP has an opposite charge to the GO, further wherein the graphene oxide-protein matrix is in the form of a 3D structure having a lumen defined by a membrane having an inner and outer surface. The invention further relates to methods and kits for preparing such a graphene oxide-protein matrix and its uses.

Figure 1:
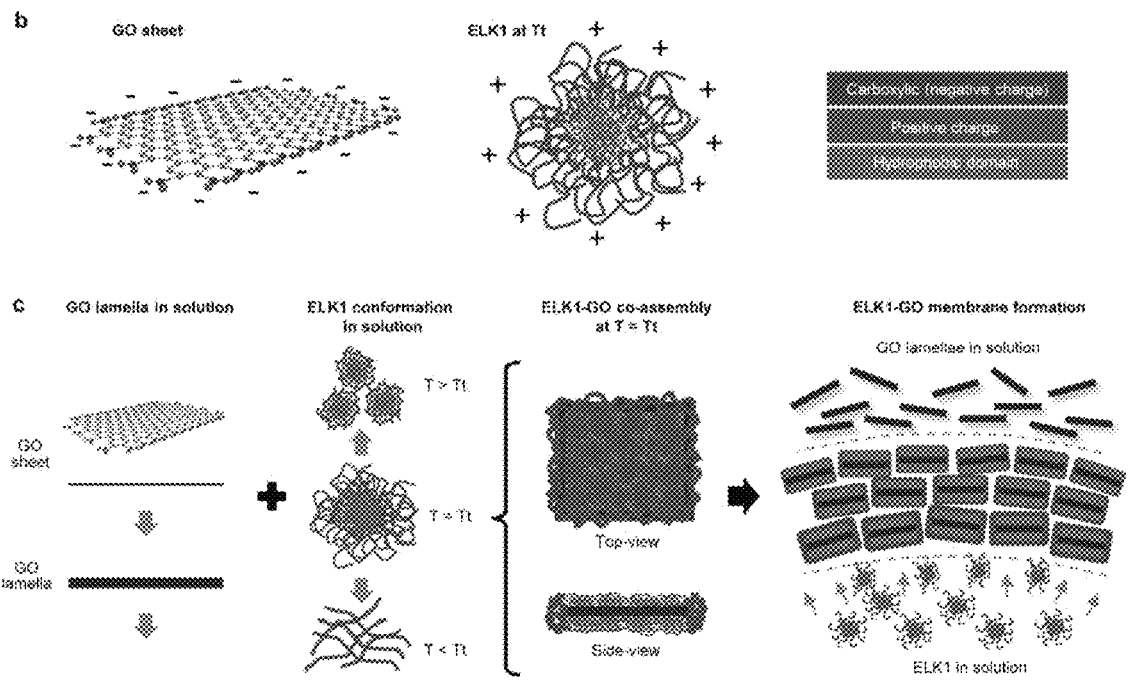

20 Claims, 26 Drawing Sheets
Specification includes a Sequence Listing.

(51) Int. Cl.

| | |
|---|---|
| *A61L 27/38* | (2006.01) |
| *A61L 27/50* | (2006.01) |
| *B33Y 10/00* | (2015.01) |
| *B33Y 80/00* | (2015.01) |

(52) U.S. Cl.
CPC .............. *A61L 27/507* (2013.01); *B33Y 10/00* (2014.12); *B33Y 80/00* (2014.12); *A61L 2300/214* (2013.01); *A61L 2300/414* (2013.01); *A61L 2300/622* (2013.01); *A61L 2300/624* (2013.01); *A61L 2430/40* (2013.01)

(58) Field of Classification Search
CPC ......... A61L 2300/414; A61L 2300/622; A61L 2300/624; A61L 2430/40; B33Y 10/00; B33Y 80/00
See application file for complete search history.

(56) References Cited

OTHER PUBLICATIONS

Univ China Petroleum, machine translation provided from FIT via PE2E of CN 105268021, 2016 (Year: 2016).*

Liu, Application of Graphene Oxide in Water Treatment, 2017, Earth and Environmental Science, 94, 1-6 (Year: 2017).*

Meana et al., Graphene oxide membranes for ocular tissue engineering, 2016, Investigative Ophthalmology & Visual Science, 57, 897 (Year: 2016).*

Li et al., Recruitment of multiple cell lines by collagen-synthetic copolymer matrices in corneal regeneration, Biomaterials, 26, 3093-3104 (Year: 2005).*

Misbah et al., Recombinant DNA technology and click chemistry: a powerful combination for generating a hybrid elastin-like-tatherin hydrogel to control calcium phosphate mineralization, 2017, Beilstein Journal of Nanotechnology, 8, 772-783 (Year: 2017).*

Santo et al., Temperature-responsive bioactive hydrogels based on a multifunctional recombinant elastin-like polymer, 2015, Biomaterials and Biomedical Engineering, 2, 47-59 (Year: 2015).*

Alagoz et al., "PHBV wet-spun scaffold coated with ELR-REDV improves vascularization for bone tissue engineering", Biomedical Materials, Institute of Physics Publishing, Bristol, GB, vol. 13, No. 5 (2018), 55010, XP020330233.

Altschul, et al., "Basic Local Alignment Search Tool", J Mol Biol., 215, 403-410, 1990.

Devereux, et al., "A comprehensive set of sequence analysis programs for the VAX", Nucleic Acids Research, vol. 12, No. 1, 1984.

Izukaf et al, "The Disordered and β Conformations of Silk Fibroin in Solution*", Biochemistry, vol. 7, No. 6 (1968), pp. 2218-2228, XP055650192.

Okesola, et al., "Multicomponent self-assembly as a tool to harness new properties from peptides and proteins in material design", Chem Soc Rev., 47, 3721, 2018.

Park, et al., "Graphene Oxide Flakes as a Cellular Adhesive: Prevention of Reactive Oxygen Species Mediated Death of Implanted Cells for Cardiac Repair", American Chemical Society, vol. 9, No. 5, 4987-4999, 2015.

PCT International Search Report, PCT/EP2019/075264, sent Dec. 18, 2019, 3 pages.

Reina, et al., "Promises, facts and challenges for graphene in biodedical applications", Chem Soc Rev., 46, 4400, 2017.

Van Der Lee, et al., "Classification of Intrinsically Disordered Regions and Proteins", American Chemical Society, 114, 6589-6631, 2014.

Wang et al., "Graphene-Based Materials Functionalized with Elastin-like Polypeptides", Langmuir, US, (Feb. 19, 2014), vol. 30, No. 8 (2014), pp. 2223-2229, XP055649379.

Yang, et al., "Graphene based materials for biomedical applications", Materials Today, vol. 16, No. 10, 2013, 9 pages.

* cited by examiner a    Molecular information of elastin-like recombinamers (ELRs)

| ELR molecules | | Sequence | Tt (°C) (2% water solution) | Molecular weight (kDa) |
|---|---|---|---|---|
| ELR-I120 | (ELK0) | MESLLP-(VPGIG VPGIG VPGIG VPGIG VPGIG)24 | 15 | 51.6 |
| ELR-IK24 | (ELK1) | MESLLP-(VPGIG VPGIG VPGKG VPGIG VPGIG)24 | 30 | 51.9 |
| ELR-(IK3)24 | (ELK3) | MESLLP-(VPGIG VPGKG VPGKG VPGKG VPGIG)24 | 80 | 52.7 |

| Resilin | | | | | Resilin+GO | | | |
|---|---|---|---|---|---|---|---|---|
| Temperature (°c) | beta-sheet | beta-turn | random | alpha-helix | Temperature (°c) | beta-sheet | beta-turn | random | alpha-helix |
| <Tt | 57.4 | 0.8 | 38.4 | 3.2 | <Tt | 28.6 | 16.1 | 50.9 | 4.3 |
| >Tt | 12.8 | 3.8 | 69.9 | 13.3 | >Tt | 46.3 | 4.3 | 45.2 | 4.2 | a)

b)

a)

b)

Bottom view

First layer
Second layer a)

| Height | 21 mm |
|---|---|
| Pressure | 0.05 Mpa |
| Inject points | 5 |
| Open valve time | 100 µs | b)

Inkjet parameters

| Height | 21 mm |
|---|---|
| Inject points | 5 |
| Open valve time | 100 μs |
| Close valve time | 1000 μs |

| Pressure (Mpa) | 0.05 | 0.06 | 0.07 | 0.08 |
|---|---|---|---|---|
| structure | | | | split | a)

b)

0.05% GO-2% ELK1

0.10% GO-2% ELK1

0.15% GO-2% ELK1 a.

b.

c.

a.

inside outside 0.05% GO          0.10% GO          0.15% GO b.

% Porosity -% GO c.

Average pore size (µm)

| % GO | 0.05 | 0.10 | 0.15 |
|---|---|---|---|
| inside | 1.2±0.6 | 0.7±0.5 | 0.5±0.4 |
| outside | 4.0±0.5 | 2.0±0.6 | 1.6±0.8 |

Figure 13 b.

Tuneable permeability (FITC-Dextran 20kDa)

Tuneable permeability (Fluorescein sodium salt )

| % GO | FITC-Dextran 20kDa permeability constant ($10^{-6}$ cm/s) | Fluorescein sodium salt permeability constant ($10^{-5}$ cm/s) |
|---|---|---|
| 0.05 | 58 | 5.2 |
| 0.10 | 4.9 | 4.6 |
| 0.15 | 2 | 1.4 | b.

| Cell density (/mL) | Permeability constant $10^{-6}$ cm/s |
|---|---|
| control(0) | 2.2 |
| $5 \times 10^3$ | 1.2 |
| $10^4$ | 0.72 |
| $5 \times 10^4$ | 0.65 |

0.15% GO       0.05% GO

| | $E_{0\ max}$ [kPa] | $E_{0\ min}$ [kPa] | $T_{0\ max}$ [mJ/g] | $T_{0\ min}$ [mJ/g] | $\sigma_{0\ max}$ [kPa] | $\sigma_{0\ min}$ [kPa] | $\varepsilon_0$ [-] |
|---|---|---|---|---|---|---|---|
| 0.05% | 147.37 | 128.78 | 0.55 | 0.48 | 19.58 | 14.65 | 0.19 |
| 0.10% | 247.15 | 212.90 | 1.12 | 1.11 | 21.74 | 19.30 | 0.29 |
| 0.15% | 208.16 | 159.57 | 3.50 | 2.10 | 34.10 | 29.07 | 0.38 |

ELP

ELP-GO mixture

Dense aggregate
of ELP with GO

SEQUENCE LISTING

```
<160> NUMBER OF SEQ ID NOS: 15

<210> SEQ ID NO 1
<211> LENGTH: 9
<212> TYPE: PRT
<213> ORGANISM: Artificial Sequence
<220> FEATURE:
<223> OTHER INFORMATION: graphene binding peptide or graphene
      stabilising peptide

<400> SEQUENCE: 1

His Asn Trp Tyr His Trp Trp Pro His
1               5

<210> SEQ ID NO 2
<211> LENGTH: 12
<212> TYPE: PRT
<213> ORGANISM: Artificial Sequence
<220> FEATURE:
<223> OTHER INFORMATION: graphene binding peptide or graphene
      stabilising peptide
```

-continued

```
<400> SEQUENCE: 2

His Ser Ser Tyr Trp Tyr Ala Phe Asn Asn Lys Thr
1               5                   10

<210> SEQ ID NO 3
<211> LENGTH: 5
<212> TYPE: PRT
<213> ORGANISM: Artificial Sequence
<220> FEATURE:
<223> OTHER INFORMATION: pentamer

<400> SEQUENCE: 3

Val Pro Gly Val Gly
1               5

<210> SEQ ID NO 4
<211> LENGTH: 5
<212> TYPE: PRT
<213> ORGANISM: Artificial Sequence
<220> FEATURE:
<223> OTHER INFORMATION: pentamer

<400> SEQUENCE: 4

Val Pro Gly Asp Gly
1               5

<210> SEQ ID NO 5
<211> LENGTH: 5
<212> TYPE: PRT
<213> ORGANISM: Artificial Sequence
<220> FEATURE:
<223> OTHER INFORMATION: pentamer

<400> SEQUENCE: 5

Val Pro Gly Glu Gly
1               5

<210> SEQ ID NO 6
<211> LENGTH: 5
<212> TYPE: PRT
<213> ORGANISM: Artificial Sequence
<220> FEATURE:
<223> OTHER INFORMATION: pentamer

<400> SEQUENCE: 6

Val Gly Ile Pro Gly
1               5

<210> SEQ ID NO 7
<211> LENGTH: 5
<212> TYPE: PRT
<213> ORGANISM: Artificial Sequence
<220> FEATURE:
<223> OTHER INFORMATION: pentamer

<400> SEQUENCE: 7

Val Pro Gly Ile Gly
1               5

<210> SEQ ID NO 8
<211> LENGTH: 5
<212> TYPE: PRT
<213> ORGANISM: Artificial Sequence
<220> FEATURE:
<223> OTHER INFORMATION: pentamer
```

-continued

```
<400> SEQUENCE: 8

Val Pro Gly Lys Gly
1               5

<210> SEQ ID NO 9
<211> LENGTH: 5
<212> TYPE: PRT
<213> ORGANISM: Artificial Sequence
<220> FEATURE:
<223> OTHER INFORMATION: pentamer
<220> FEATURE:
<221> NAME/KEY: MISC_FEATURE
<222> LOCATION: (4)..(4)
<223> OTHER INFORMATION: wherein X is any amino acid apart from proline

<400> SEQUENCE: 9

Val Pro Gly Xaa Gly
1               5

<210> SEQ ID NO 10
<211> LENGTH: 31
<212> TYPE: PRT
<213> ORGANISM: Artificial Sequence
<220> FEATURE:
<223> OTHER INFORMATION: ELK1

<400> SEQUENCE: 10

Met Glu Ser Leu Leu Pro Val Pro Gly Ile Gly Val Pro Gly Ile Gly
1               5                   10                  15

Val Pro Gly Lys Gly Val Pro Gly Ile Gly Val Pro Gly Ile Gly
            20                  25                  30

<210> SEQ ID NO 11
<211> LENGTH: 629
<212> TYPE: PRT
<213> ORGANISM: Artificial Sequence
<220> FEATURE:
<223> OTHER INFORMATION: ELK0

<400> SEQUENCE: 11

Met Glu Ser Leu Leu Val Pro Gly Ile Gly Val Pro Gly Ile Gly Val
1               5                   10                  15

Pro Gly Ile Gly Val Pro Gly Ile Gly Val Pro Gly Ile Gly Val Val
            20                  25                  30

Pro Gly Ile Gly Val Pro Gly Ile Gly Val Pro Gly Ile Gly Val Pro
        35                  40                  45

Gly Ile Gly Val Pro Gly Ile Gly Val Val Pro Gly Ile Gly Val Pro
    50                  55                  60

Gly Ile Gly Val Pro Gly Ile Gly Val Pro Gly Ile Gly Val Pro Gly
65                  70                  75                  80

Ile Gly Val Val Pro Gly Ile Gly Val Pro Gly Ile Gly Val Pro Gly
                85                  90                  95

Ile Gly Val Pro Gly Ile Gly Val Pro Gly Ile Gly Val Val Pro Gly
            100                 105                 110

Ile Gly Val Pro Gly Ile Gly Val Pro Gly Ile Gly Val Pro Gly Ile
        115                 120                 125

Gly Val Pro Gly Ile Gly Val Val Pro Gly Ile Gly Val Pro Gly Ile
    130                 135                 140

Gly Val Pro Gly Ile Gly Val Pro Gly Ile Gly Val Pro Gly Ile Gly
145                 150                 155                 160

Val Val Pro Gly Ile Gly Val Pro Gly Ile Gly Val Pro Gly Ile Gly
```

-continued

```
                165               170               175
Val Pro Gly Ile Gly Val Pro Gly Ile Gly Val Val Pro Gly Ile Gly
            180               185               190

Val Pro Gly Ile Gly Val Pro Gly Ile Gly Val Pro Gly Ile Gly Val
            195               200               205

Pro Gly Ile Gly Val Val Pro Gly Ile Gly Val Pro Gly Ile Gly Val
            210               215               220

Pro Gly Ile Gly Val Pro Gly Ile Gly Val Pro Gly Ile Gly Val Val
225               230               235               240

Pro Gly Ile Gly Val Pro Gly Ile Gly Val Pro Gly Ile Gly Val Pro
            245               250               255

Gly Ile Gly Val Pro Gly Ile Gly Val Val Pro Gly Ile Gly Val Pro
            260               265               270

Gly Ile Gly Val Pro Gly Ile Gly Val Pro Gly Ile Gly Val Pro Gly
            275               280               285

Ile Gly Val Val Pro Gly Ile Gly Val Pro Gly Ile Gly Val Pro Gly
            290               295               300

Ile Gly Val Pro Gly Ile Gly Val Pro Gly Ile Gly Val Val Pro Gly
305               310               315               320

Ile Gly Val Pro Gly Ile Gly Val Pro Gly Ile Gly Val Pro Gly Ile
            325               330               335

Gly Val Pro Gly Ile Gly Val Val Pro Gly Ile Gly Val Pro Gly Ile
            340               345               350

Gly Val Pro Gly Ile Gly Val Pro Gly Ile Gly Val Pro Gly Ile Gly
            355               360               365

Val Val Pro Gly Ile Gly Val Pro Gly Ile Gly Val Pro Gly Ile Gly
            370               375               380

Val Pro Gly Ile Gly Val Pro Gly Ile Gly Val Val Pro Gly Ile Gly
385               390               395               400

Val Pro Gly Ile Gly Val Pro Gly Ile Gly Val Pro Gly Ile Gly Val
            405               410               415

Pro Gly Ile Gly Val Val Pro Gly Ile Gly Val Pro Gly Ile Gly Val
            420               425               430

Pro Gly Ile Gly Val Pro Gly Ile Gly Val Pro Gly Ile Gly Val Val
            435               440               445

Pro Gly Ile Gly Val Pro Gly Ile Gly Val Pro Gly Ile Gly Val Pro
    450               455               460

Gly Ile Gly Val Pro Gly Ile Gly Val Val Pro Gly Ile Gly Val Pro
465               470               475               480

Gly Ile Gly Val Pro Gly Ile Gly Val Pro Gly Ile Gly Val Pro Gly
            485               490               495

Ile Gly Val Val Pro Gly Ile Gly Val Pro Gly Ile Gly Val Pro Gly
            500               505               510

Ile Gly Val Pro Gly Ile Gly Val Pro Gly Ile Gly Val Val Pro Gly
            515               520               525

Ile Gly Val Pro Gly Ile Gly Val Pro Gly Ile Gly Val Pro Gly Ile
    530               535               540

Gly Val Pro Gly Ile Gly Val Pro Gly Ile Gly Val Pro Gly Ile
545               550               555               560

Gly Val Pro Gly Ile Gly Val Pro Gly Ile Gly Val Pro Gly Ile Gly
            565               570               575

Val Val Pro Gly Ile Gly Val Pro Gly Ile Gly Val Pro Gly Ile Gly
            580               585               590
```

-continued

```
Val Pro Gly Ile Gly Val Pro Gly Ile Gly Val Pro Gly Ile Gly
        595                 600                 605

Val Pro Gly Ile Gly Val Pro Gly Ile Gly Val Pro Gly Ile Gly Val
    610                 615                 620

Pro Gly Ile Gly Val
625

<210> SEQ ID NO 12
<211> LENGTH: 606
<212> TYPE: PRT
<213> ORGANISM: Artificial Sequence
<220> FEATURE:
<223> OTHER INFORMATION: ELK1

<400> SEQUENCE: 12

Met Glu Ser Leu Leu Pro Val Pro Gly Ile Gly Val Pro Gly Ile Gly
1               5                   10                  15

Val Pro Gly Lys Gly Val Pro Gly Ile Gly Val Pro Gly Ile Gly Val
            20                  25                  30

Pro Gly Ile Gly Val Pro Gly Ile Gly Val Pro Gly Lys Gly Val Pro
        35                  40                  45

Gly Ile Gly Val Pro Gly Ile Gly Val Pro Gly Ile Gly Val Pro Gly
    50                  55                  60

Ile Gly Val Pro Gly Lys Gly Val Pro Gly Ile Gly Val Pro Gly Ile
65                  70                  75                  80

Gly Val Pro Gly Ile Gly Val Pro Gly Ile Gly Val Pro Gly Lys Gly
            85                  90                  95

Val Pro Gly Ile Gly Val Pro Gly Ile Gly Val Pro Gly Ile Gly Val
            100                 105                 110

Pro Gly Ile Gly Val Pro Gly Lys Gly Val Pro Gly Ile Gly Val Pro
        115                 120                 125

Gly Ile Gly Val Pro Gly Ile Gly Val Pro Gly Ile Gly Val Pro Gly
    130                 135                 140

Lys Gly Val Pro Gly Ile Gly Val Pro Gly Ile Gly Val Pro Gly Ile
145                 150                 155                 160

Gly Val Pro Gly Ile Gly Val Pro Gly Lys Gly Val Pro Gly Ile Gly
            165                 170                 175

Val Pro Gly Ile Gly Val Pro Gly Ile Gly Val Pro Gly Ile Gly Val
            180                 185                 190

Pro Gly Lys Gly Val Pro Gly Ile Gly Val Pro Gly Ile Gly Val Pro
        195                 200                 205

Gly Ile Gly Val Pro Gly Ile Gly Val Pro Gly Lys Gly Val Pro Gly
    210                 215                 220

Ile Gly Val Pro Gly Ile Gly Val Pro Gly Ile Gly Val Pro Gly Ile
225                 230                 235                 240

Gly Val Pro Gly Lys Gly Val Pro Gly Ile Gly Val Pro Gly Ile Gly
            245                 250                 255

Val Pro Gly Ile Gly Val Pro Gly Ile Gly Val Pro Gly Lys Gly Val
            260                 265                 270

Pro Gly Ile Gly Val Pro Gly Ile Gly Val Pro Gly Ile Gly Val Pro
        275                 280                 285

Gly Ile Gly Val Pro Gly Lys Gly Val Pro Gly Ile Gly Val Pro Gly
    290                 295                 300

Ile Gly Val Pro Gly Ile Gly Val Pro Gly Ile Gly Val Pro Gly Lys
305                 310                 315                 320
```

-continued

```
Gly Val Pro Gly Ile Gly Val Pro Gly Ile Gly Val Pro Gly Ile Gly
            325                 330                 335

Val Pro Gly Ile Gly Val Pro Gly Lys Gly Val Pro Gly Ile Gly Val
            340                 345                 350

Pro Gly Ile Gly Val Pro Gly Ile Gly Val Pro Gly Ile Gly Val Pro
            355                 360                 365

Gly Lys Gly Val Pro Gly Ile Gly Val Pro Gly Ile Gly Val Pro Gly
            370                 375                 380

Ile Gly Val Pro Gly Ile Gly Val Pro Gly Lys Gly Val Pro Gly Ile
385                 390                 395                 400

Gly Val Pro Gly Ile Gly Val Pro Gly Ile Gly Val Pro Gly Ile Gly
            405                 410                 415

Val Pro Gly Lys Gly Val Pro Gly Ile Gly Val Pro Gly Ile Gly Val
            420                 425                 430

Pro Gly Ile Gly Val Pro Gly Ile Gly Val Pro Gly Lys Gly Val Pro
            435                 440                 445

Gly Ile Gly Val Pro Gly Ile Gly Val Pro Gly Ile Gly Val Pro Gly
            450                 455                 460

Ile Gly Val Pro Gly Lys Gly Val Pro Gly Ile Gly Val Pro Gly Ile
465                 470                 475                 480

Gly Val Pro Gly Ile Gly Val Pro Gly Ile Gly Val Pro Gly Lys Gly
            485                 490                 495

Val Pro Gly Ile Gly Val Pro Gly Ile Gly Val Pro Gly Ile Gly Val
            500                 505                 510

Pro Gly Ile Gly Val Pro Gly Lys Gly Val Pro Gly Ile Gly Val Pro
            515                 520                 525

Gly Ile Gly Val Pro Gly Ile Gly Val Pro Gly Ile Gly Val Pro Gly
            530                 535                 540

Lys Gly Val Pro Gly Ile Gly Val Pro Gly Ile Gly Val Pro Gly Ile
545                 550                 555                 560

Gly Val Pro Gly Ile Gly Val Pro Gly Lys Gly Val Pro Gly Ile Gly
            565                 570                 575

Val Pro Gly Ile Gly Val Pro Gly Ile Gly Val Pro Gly Ile Gly Val
            580                 585                 590

Pro Gly Lys Gly Val Pro Gly Ile Gly Val Pro Gly Ile Gly
            595                 600                 605
```

```
<210> SEQ ID NO 13
<211> LENGTH: 606
<212> TYPE: PRT
<213> ORGANISM: Artificial Sequence
<220> FEATURE:
<223> OTHER INFORMATION: ELK3

<400> SEQUENCE: 13

Met Glu Ser Leu Leu Pro Val Pro Gly Ile Gly Val Pro Gly Lys Gly
1               5                   10                  15

Val Pro Gly Lys Gly Val Pro Gly Lys Gly Val Pro Gly Ile Gly Val
            20                  25                  30

Pro Gly Ile Gly Val Pro Gly Lys Gly Val Pro Gly Lys Gly Val Pro
            35                  40                  45

Gly Lys Gly Val Pro Gly Ile Gly Val Pro Gly Ile Gly Val Pro Gly
        50                  55                  60

Lys Gly Val Pro Gly Lys Gly Val Pro Gly Lys Gly Val Pro Gly Ile
65                  70                  75                  80
```

-continued

```
Gly Val Pro Gly Ile Gly Val Pro Gly Lys Gly Val Pro Gly Lys Gly
                85                  90                  95

Val Pro Gly Lys Gly Val Pro Gly Ile Gly Val Pro Gly Ile Gly Val
               100                 105                 110

Pro Gly Lys Gly Val Pro Gly Lys Gly Val Pro Gly Lys Gly Val Pro
               115                 120                 125

Gly Ile Gly Val Pro Gly Ile Gly Val Pro Gly Lys Gly Val Pro Gly
           130                 135                 140

Lys Gly Val Pro Gly Lys Gly Val Pro Gly Ile Gly Val Pro Gly Ile
145                 150                 155                 160

Gly Val Pro Gly Lys Gly Val Pro Gly Lys Gly Val Pro Gly Lys Gly
               165                 170                 175

Val Pro Gly Ile Gly Val Pro Gly Ile Gly Val Pro Gly Lys Gly Val
               180                 185                 190

Pro Gly Lys Gly Val Pro Gly Lys Gly Val Pro Gly Ile Gly Val Pro
               195                 200                 205

Gly Ile Gly Val Pro Gly Lys Gly Val Pro Gly Lys Gly Val Pro Gly
           210                 215                 220

Lys Gly Val Pro Gly Ile Gly Val Pro Gly Ile Gly Val Pro Gly Lys
225                 230                 235                 240

Gly Val Pro Gly Lys Gly Val Pro Gly Lys Gly Val Pro Gly Ile Gly
               245                 250                 255

Val Pro Gly Ile Gly Val Pro Gly Lys Gly Val Pro Gly Lys Gly Val
               260                 265                 270

Pro Gly Lys Gly Val Pro Gly Ile Gly Val Pro Gly Ile Gly Val Pro
               275                 280                 285

Gly Lys Gly Val Pro Gly Lys Gly Val Pro Gly Lys Gly Val Pro Gly
           290                 295                 300

Ile Gly Val Pro Gly Ile Gly Val Pro Gly Lys Gly Val Pro Gly Lys
305                 310                 315                 320

Gly Val Pro Gly Lys Gly Val Pro Gly Ile Gly Val Pro Gly Ile Gly
               325                 330                 335

Val Pro Gly Lys Gly Val Pro Gly Lys Gly Val Pro Gly Lys Gly Val
               340                 345                 350

Pro Gly Ile Gly Val Pro Gly Ile Gly Val Pro Gly Lys Gly Val Pro
           355                 360                 365

Gly Lys Gly Val Pro Gly Lys Gly Val Pro Gly Ile Gly Val Pro Gly
           370                 375                 380

Ile Gly Val Pro Gly Lys Gly Val Pro Gly Lys Gly Val Pro Gly Lys
385                 390                 395                 400

Gly Val Pro Gly Ile Gly Val Pro Gly Ile Gly Val Pro Gly Lys Gly
               405                 410                 415

Val Pro Gly Lys Gly Val Pro Gly Lys Gly Val Pro Gly Ile Gly Val
               420                 425                 430

Pro Gly Ile Gly Val Pro Gly Lys Gly Val Pro Gly Lys Gly Val Pro
           435                 440                 445

Gly Lys Gly Val Pro Gly Ile Gly Val Pro Gly Ile Gly Val Pro Gly
           450                 455                 460

Lys Gly Val Pro Gly Lys Gly Val Pro Gly Lys Gly Val Pro Gly Ile
465                 470                 475                 480

Gly Val Pro Gly Ile Gly Val Pro Gly Lys Gly Val Pro Gly Lys Gly
               485                 490                 495
```

-continued

```
Val Pro Gly Lys Gly Val Pro Gly Ile Gly Val Pro Gly Ile Gly Val
        500             505             510

Pro Gly Lys Gly Val Pro Gly Lys Gly Val Pro Gly Lys Gly Val Pro
        515             520             525

Gly Ile Gly Val Pro Gly Ile Gly Val Pro Gly Lys Gly Val Pro Gly
        530             535             540

Lys Gly Val Pro Gly Lys Gly Val Pro Gly Ile Gly Val Pro Gly Ile
545             550             555             560

Gly Val Pro Gly Lys Gly Val Pro Gly Lys Gly Val Pro Gly Lys Gly
            565             570             575

Val Pro Gly Ile Gly Val Pro Gly Ile Gly Val Pro Gly Lys Gly Val
        580             585             590

Pro Gly Lys Gly Val Pro Gly Lys Gly Val Pro Gly Ile Gly
        595             600             605

<210> SEQ ID NO 14
<211> LENGTH: 13
<212> TYPE: PRT
<213> ORGANISM: Artificial Sequence
<220> FEATURE:
<223> OTHER INFORMATION: disordered protein

<400> SEQUENCE: 14

Met Ser Lys Gly Pro Gly Arg Gly Asp Gln Pro Tyr Gln
1               5               10

<210> SEQ ID NO 15
<211> LENGTH: 165
<212> TYPE: PRT
<213> ORGANISM: Artificial Sequence
<220> FEATURE:
<223> OTHER INFORMATION: disordered protein

<400> SEQUENCE: 15

Met Ser Lys Gly Pro Gly Arg Gly Asp Gln Pro Tyr Gln Gly Arg Gly
1               5               10              15

Asp Gln Pro Tyr Gln Gly Arg Gly Asp Gln Pro Tyr Gln Gly Arg Gly
            20              25              30

Asp Gln Pro Tyr Gln Gly Arg Gly Asp Gln Pro Tyr Gln Gly Arg Gly
        35              40              45

Asp Gln Pro Tyr Gln Gly Arg Gly Asp Gln Pro Tyr Gln Gly Arg Gly
        50              55              60

Asp Gln Pro Tyr Gln Gly Arg Gly Asp Gln Pro Tyr Gln Gly Arg Gly
65              70              75              80

Asp Gln Pro Tyr Gln Gly Arg Gly Asp Gln Pro Tyr Gln Gly Arg Gly
            85              90              95

Asp Gln Pro Tyr Gln Gly Arg Gly Asp Gln Pro Tyr Gln Gly Arg Gly
            100             105             110

Asp Gln Pro Tyr Gln Gly Arg Gly Asp Gln Pro Tyr Gln Gly Arg Gly
        115             120             125

Asp Gln Pro Tyr Gln Gly Arg Gly Asp Gln Pro Tyr Gln Gly Arg Gly
        130             135             140

Asp Gln Pro Tyr Gln Gly Arg Gly Asp Gln Pro Tyr Gln Gly Arg Gly
145             150             155             160

Asp Gln Pro Tyr Gln
            165
```

SELF-ASSEMBLING GRAPHENE OXIDE-PROTEIN MATRIX

CROSS-REFERENCE TO RELATED APPLICATIONS

This application is the U.S. national phase application filed under 35 U.S.C. § 371 claiming benefit to International Patent Application No. PCT/EP2019/075264, filed on Sep. 19, 2019, which claims priority to GB Patent Application No. 1815285.0, filed Sep. 19, 2018, the disclosures of which are incorporated herein by reference in their entirety.

FIELD OF THE INVENTION

The present invention relates to a stable self-assembling graphene oxide-protein matrix, methods and kits for preparing such a graphene oxide-protein matrix and its uses.

BACKGROUND

There is an increasing interest in the generation of materials with bioinspired functions such as the capacity to grow, self-replicate, or controllably respond to specific stimuli. Biological materials acquire most of these functionalities as a consequence of their ability to self-assemble various types of building blocks at multiple length scales. Human tissues, for example, are composed of an assortment of well-organized macromolecules and proteins that give rise to hierarchical structures with amazing properties and function. However, such complex structures require more than just well-organized building-blocks, but rather dynamic and well-controlled mechanisms that direct self-assembly with precise spatiotemporal control.

Engineering materials in this manner provides an opportunity to not only take advantage of the individual building-blocks, but also enables emergent properties as a result of the interactions between the different components. In this way, structures with enhanced modularity, complexity, and tuneability of properties such as structural hierarchy, adhesion, electrical conductivity, or the capacity to grow can be generated. Consequently, multicomponent self-assembly represents an attractive route to move beyond structure and, from a holistic perspective, develop more complex, dynamic, and functional materials (Mata et al, *Chem. Soc. Rev.* 47, (2018)).

Proteins are the most functional building-blocks of organisms and, as such, have been thoroughly explored to engineer intelligent materials. However, new discoveries are shaping our understanding of how proteins function and providing new and advanced strategies for their utilisation. For example, there is increasing evidence that both ordered (i.e. β-sheet, α-helix) and disordered (i.e. random coil) regions of proteins play a role in their functionality (Van der Lee et al. *Chem. Rev.* 114, (2014)). Furthermore, there is a growing acceptance that this functionality is regulated by their interaction with other molecules.

Based on these principles, proteins are emerging as dynamic building blocks of multicomponent systems that can be used to engineer intelligent materials. For example, the disordered nature of proteins such as resilin or elastin-like polypeptides (ELPs) to modulate their conformation and generate dynamic or hierarchically mineralizing materials can be exploited. ELPs, also known as elastin-like recombinamers (ELRs), are based on the natural elastin motif Val-Pro-Gly-X-Gly (VPGXG), where X could be any amino acid apart from proline.

Multicomponent self-assembly also offers a unique opportunity to engineer complex hybrid systems. In particular, the controlled incorporation of graphene as a building-block could lead to the design of new biomaterials that benefit from its distinctive two-dimensional (2D) structure and outstanding electronic, thermal, and mechanical properties (Yang et al, *Mater. Today* 16, (2013)). Towards this goal, graphene and its derivatives have been modified with biomacromolecules such as DNA, proteins, and biopolymers and used in, for example, implants and scaffolds for cell culture and regenerative medicine (Park et al, *ACS Nano* 9, (2015)). Furthermore, graphene oxide (GO) is gaining significant interest and being used instead of graphene given its rich oxygen functional groups (hydroxyl, epoxy, carbonyl, and carboxyl), which facilitate designed interactions with different molecules. GO is easy dispersed in water and other organic solvents, as well as in different matrixes, due to the presence of the oxygen functionalities. GO can also be functionalised using these oxygen groups.

However, both graphene and GO exhibit key limitations such as dose-depend toxicity and issues associated with hierarchical organisation and the ability to generate uniform and stable structures (Reina et al, *Chem. Soc. Rev.* 46, (2017).

Previous studies have demonstrated the possibility to co-assemble peptides with large macromolecules to generate hierarchical membranes at a liquid-liquid interface. These systems rely on both molecular interactions between the two components as well as their respective individual properties such as molecular weight, charge, and 3D conformation. However, the resulting materials tend to either be weak or rely on specific environmental conditions, which limit their functionality and widespread use. There remains an unmet need to turn molecular self-assembly into functional devices with practical applications at the macroscale, which have advanced properties such as the capacity to withstand flow.

Material platforms that exploit the functionalities of proteins and GO as well as the benefits of multicomponent self-assembly offer exciting possibilities for the engineering of advanced materials that are both stable and dynamic. Experimental approaches, molecular dynamics (MD) simulations and rapid prototyping techniques can be used to harness the inherent properties of both disordered proteins (DPs) and graphene oxide (GO), elucidate the underlying molecular mechanism and develop rules for its use to transform rational molecular design into functional engineering with potential wide-spread use.

Regenerative medicine is the field concerned with repairing or replacing cells or tissues to restore normal function. It may involve transplantation, stimulation of the body's own repair processes, or the use of cells as delivery-vehicles for therapeutic agents. Regenerative medicine also provides the possibility of growing tissues and organs in a laboratory and implanting them in a subject. This can be used to address the problem of the shortage of organs available for donation, and the problem of organ transplant rejection. This overlaps with the field of tissue engineering and the need to grow artificial tissues and organs. However, there are many difficulties associated with the growth of artificial tissues and organs, such as high cost, rejection and lack of certain biological functions. There is an unmet need in the art for tissues and organs that are robust, stable and accurately mimic the properties of natural tissues or organs and time and cost-efficient methods of preparing these.

For example, cardiovascular diseases are the number one cause of unnatural death globally. Increasing aged population with higher risk of developing cardiovascular disorders is key factor expected to propel growth of the market for treatment and prevention of cardiovascular disease. Such high prevalence of cardiovascular diseases will increase the need for artificial blood vessels since the vascular damage caused by injury, atherosclerosis, cardiovascular disease, congenital heart disease and cerebrovascular diseases cannot be cured with drugs alone.

A serious trauma can be repaired by tissue transplantation with certain arteries or veins, but it cannot be done if the vessels are injured or the patient does not have a vessel suitable for prosthetic replacement due to size mismatch or venous disease. The strong rejection reaction of allografts and xenografts can also be a serious, often life-threating complication if it occurs. For these reasons, artificial blood vessels (ABV) are required to treat cardiovascular disease and injury.

Artificial blood vessels should be permeable since enabling diffusion of nutrients, oxygen, waste materials, and cell migration may be critical. In order to create the most realistic artificial blood vessels this permeability should be able to be modulated within the structure. For example, to enable recreation of biological structures that have aniso-tropic structures, there must be the possibility to create tubes with different levels of permeability along the long axis of the tube. Creating this in a single injection is not currently possible using any known methods.

However, expensive vascular graft procedures, high cost and high risk of developing infection are just a few of the difficulties faced. There is a need in the art to develop robust, stable and dynamic artificial blood vessels that are porous, biocompatible and can support cell growth, but are not difficult or expensive to produce.

3D printing is also used in the field of tissue engineering and regenerative medicine to print biological structures or biomedical components to mimic the characteristics of natu-ral tissues. However, artificial organs such as livers and kidneys made by 3D bioprinting have been shown to lack elements that may be crucial such as working blood vessels, tubules for collecting urine and other features to allow oxygen and nutrients to perfuse the entire tissue. A further difficulty with current 3D bioprinting methods is also cre-ating and maintaining a stable structure with practical mechanical properties once the printing is complete. A key challenge in 3D bioprinting is the bioinks are often com-prised of a thick slurry of cells to facilitate printing and solidification of the bioink after printing, this high viscosity necessary to solidify the bioink can be detrimental to cell viability during the printing process. One of the major challenges for bioinks is their capacity to keep the cells alive during and after the printing because the bioink has to be cell friendly (provide nutrients, have pores, be the right stiffness) as well as have properties suitable for printing (flowing, fast setting, low shear stress). This means that even if bioinks are able to bioprint cells that are robust (such as cell lines) they are normally not able to safely print more delicate cells. Furthermore, using current 3D bioprinting techniques the ability to make small, robust microtubes is limited by the printing resolution. In other words, in current 3D printing methods the resolution of the final structure is determined by the printer rather than by the bioink itself. This is a limiting factor when trying to print small features (e.g. those below 50 µm). There is therefore an unmet need in the art for methods of 3D bioprinting that can reproduce elements of tissues or organs, print delicate cell types and create stable and robust structures in a cost and time-effective manner.

Microfluidic devices can be utilised in biological fields such as high-throughput screening, DNA chips, lab-on-a- chip technology, enzymatic analysis, DNA analysis (e.g., polymerase chain reaction and high-throughput sequenc-ing), and proteomics. Microfluidic biochips aim to integrate assay operations such as detection, sample pre-treatment and sample preparation on one chip, for example DNA or protein microarrays.

Lab-on-a-chip devices may use microfluidics and is con-cerned with laboratory experiments carried out on a very small scale. It can integrate several laboratory functions on a chip of size ranging from a few millimetres to a few square centimetres. This may be used in diagnostics, analysis, synthesis and sequencing. However, physical and chemical properties such as surface roughness, capillary forces, and chemical interactions between materials are more significant at the microscale level. This can often result in complica-tions during lab-on-a-chip experiments. Furthermore, the micro-manufacturing process required to make them is complex and labour intensive, requiring expensive equip-ment and experienced personnel. There is a need in the art for a cheap, simple way to prepare robust and effective lab-on-a-chip devices.

Organ-on-a-chip devices are 3D microfluidic cell culture chips that have the ability to simulate the activities, mechan-ics and physiological response of whole organs and organ systems. Areas of application include regenerative medicine, drug and toxin testing and replacing animal testing. Never-theless, even the best 3D culture models fail to mimic an organ's cellular properties including tissue-to-tissue inter-faces, spatiotemporal gradients of chemicals, and the mechanically active microenvironments. There is a need in the art for a cheap, simple way to prepare robust and effective organ-on-a-chip devices which better mimic an organ's properties.

Bioelectronics is a discipline resulting from the conver-gence of biology and electronics. It seeks to exploit biology in conjunction with electronics, for example, biological fuel cells, bionics and biomaterials for information processing, information storage, electronic components and actuators. Bio computers use systems of biological molecules, such as DNA and proteins, to perform computational functions involving storing, retrieving, and processing data. This is a developing field and there in an unmet need in the art for methods of manufacturing such bioelectronic devices or systems and conductive biological materials that can be used therein.

Through rapid prototyping techniques the inventors dem-onstrate the capacity to guide self-assembly with spatio-temporal control into well-defined, capillary-like, tubular fluidic microstructures with a high level of biocompatibility and the capacity to withstand flow. The current invention presents a new and innovative approach to grow complex and functional devices such as tissue engineering scaffolds, microfluidic systems, lab-on-a-chip or organs-on-a-chip by self-assembly.

SUMMARY OF THE INVENTION

A first aspect of the invention provides a method of preparing a graphene oxide-protein matrix, the method com-prising; admixing an aqueous solution of a disordered pro-tein (DP) with an aqueous solution of graphene oxide (GO), wherein the DP has an opposite charge to the GO, further wherein the graphene oxide-protein matrix is in the form of a three-dimensional (3D) structure having a lumen defined by a membrane having an inner and outer surface.

A second aspect of the invention provides a graphene oxide-protein matrix comprising a disordered protein (DP)

and graphene oxide (GO), wherein the DP has an opposite charge to the GO, further wherein the graphene oxide-protein matrix is in the form of a 3D structure having a lumen defined by a membrane having an inner and outer surface.

A third aspect of the invention provides a kit for preparing a graphene oxide-protein matrix, the kit comprising;

a. an aqueous solution of a disordered protein (DP)

b. an aqueous solution of graphene oxide (GO)

wherein when the aqueous solution of DP and the aqueous solution of GO are admixed, a graphene oxide-protein matrix in the form of a 3D structure having a lumen defined by a membrane having an inner and outer surface is formed spontaneously, further wherein the DP has an opposite charge to the GO.

DETAILED DESCRIPTION OF THE INVENTION

The invention as described herein provides a method of preparing a graphene oxide-protein matrix, the method comprising; admixing an aqueous solution of a disordered protein (DP) with an aqueous solution of graphene oxide (GO). The DP has an opposite charge to that of the GO. The DP and GO spontaneously self-assemble into the GO-protein matrix.

The graphene oxide-protein matrix may be in the form of a 3D structure. The graphene oxide-protein matrix may have a lumen defined by a membrane having an inner and outer surface. The membrane as described herein is comprised of the GO-protein matrix.

In some embodiments, GO-protein matrices may form without a lumen, for example in a planar form, such as a membrane or a gel.

In some embodiments, the GO-protein matrix may form a membrane that may define a lumen defined by a membrane having an inner and outer surface. This enables the membrane to form shapes such as sacs and tubes. The GO forms planar sheets with negatively charged peripheries comprised of carboxyl groups. These sheets stack on top of one another to form a GO lamella comprised of multiple layers of GO sheets (or lattices).

The DPs comprise one or more hydrophobic domains and one or more positively charged domains. The hydrophobic domains aggregate to form a hydrophobic core surrounded by a shell of positively charged domains. The form the DP takes in solution (for example the size of the core) may vary, for example depending on the temperature. When admixed, the GO and DP spontaneously self-assemble into a matrix. In the assembled matrix the positively charged domains of the DP contact the negatively charged peripheries of the GO sheets, the neutral charge hydrophobic domains of the DPs contact the planar surface of the GO sheets and the hydrophobic domains of the DP are encapsulated by a thin layer of positively charged DP domains. In this way the GO lamella is encapsulated by the DP during spontaneous self-assembly. The GO lamella may be encapsulated by the DP. The positively charged domains of the DP may contact the negatively charged peripheries of the GO sheets. The neutral charge hydrophobic domains of the DPs may contact the planar surface of the GO sheets. The hydrophobic domains may also be encapsulated by a thin layer of positively charged domains. (FIG. 1)

A matrix as described herein is an organised structure, for example a membrane, a multi-lamella structure, a network (for example a tubular network), a mesh or a gel. Preferably, the matrix as described herein may be multilamellar. The matrix as described herein may be two-dimensional (2D) or three-dimensional (3D) but preferably will be three-dimensional. The matrix as described herein may take the form of a higher order structure, for example, three-dimensional structure such as a tube or tubular structure, a sphere, a sponge, a cavity, a sac or a vesicle. The matrix as described herein is not an aggregate. The matrix as described herein has an ordered, hierarchal structure.

Three-dimensional (3D) refers to an object which can be measured in three different dimensions, for example height, depth and width. Two-dimensional (2D), as described herein, may refer to an object which is planar, meaning it is related to or situated in one plane.

The GO-protein matrix, as defined herein, may be a planar structure such as a membrane.

Alternatively, the GO-protein matrix may have a 3D structure. The 3D structure may have a lumen defined by a membrane or wall having an inner surface and outer surface. The lumen may have a substantially annular cross section and may have an interior diameter from about 10 μm to about 10 cm. The interior diameter may be from about 10 μm to about 1 cm. Preferably the interior diameter may be from about 10 μm to about 1 mm. In some embodiments, the lumen may have an interior diameter of at least about 10 μm.

The lumen, as described herein, may be capable of storing or transporting a substance such as a liquid or a gas. The lumen may have the capacity to withstand flow, such as flow rates of at least about 2 mL/min, or about 4 mL/min, or about 6 mL/min, or about 8 mL/min, or about 10 mL/min, or about 12 mL/min. In particular, the lumen may withstand the flow without sustaining damage. References to withstand flow without sustaining damage mean the ability to store, transport or hold a substance (such as a liquid or gas) without the membrane being disrupted by said substance or the flow of said substance.

The lumen may be formed and be able to withstand flow within about 10 seconds, about 20 seconds, about 30 seconds, about 1 minute, about 2 minutes, about 3 minutes, about 5 minutes, about 10 minutes or about 20 minutes of its formation by admixing GO and DP solutions. In suitable embodiment, the lumen may be formed and be able to withstand flow within about 1 minute of its formation by admixing the GO and DP solutions.

The lumen is defined by the inner surface of a membrane, which faces into the lumen. The membrane may also have an outer surface, which faces away from the lumen. The thickness of the membrane, or the distance between the inner surface and outer surface, may be from about 5 μm to about 100 μm, or from about 10 μm to about 50 μm or from about 10 μm to about 25 μm. Preferably the membrane may have a thickness of from about 10 μm to about 50 μm.

The membrane forming the lumen may have one or more apertures.

The membrane which defines the lumen, as defined herein, is comprised of the self-assembled graphene-oxide-protein matrix and comprises the graphene oxide, and the disordered protein, such as an elastin-like polypeptide or resilin. The membrane may also comprise cells and/or exosomes and/or additional structures as described herein.

The graphene oxide-protein matrix as described herein is comprised of a supramolecular framework of stacked sheets of graphene oxide in a lamellar conformation which acts as a scaffold that interacts with (i.e. contacts) the disordered protein (FIG. 1).

The "DP solution" or "solution of DP" as described herein may be a "DP dispersion" or "DP suspension". The DP solution, dispersion or suspension may comprise DP in an aqueous medium such as water, cell culture media and/or PBS.

The "GO solution" as described herein may be a "GO dispersion" or "GO suspension". The GO solution, dispersion or suspension may comprise GO sheets in an aqueous medium such as water, cell culture media and/or PBS.

The graphene oxide-protein matrix is formed by admixing an aqueous solution of a disordered protein with an aqueous solution of graphene oxide. The admixing step can comprise adding a volume of DP solution into a larger volume of GO solution. Admixing DP and GO solution initiates spontaneous self-assembly of graphene oxide-protein matrix in the form of a 3D structure, which may have a lumen defined by a membrane having an inner and outer surface, such as a tube.

"Spontaneous self-assembly", as used herein, refers to the formation of an organised structure from a disorganised system of components resulting from interactions between the components themselves without any external direction.

No additional components are needed to initiate the spontaneous self-assembly into ordered hierarchal structure such as tubes. Graphene binding peptides or graphene stabilising peptides are also not required. A graphene binding peptide or graphene stabilising peptide may consist of the amino acid sequence HNWYHWWPH, or HSSYWY-AFNNKT.

Through hydrophobic and electrostatic interactions between the DP molecules and high surface area GO lamella, a diffusion-reaction mechanism leads to an interfacial membrane with both enhanced stability and dynamic properties, facilitating material manipulation and the capacity to engineer with it.

The admixing step, as used herein, may comprise adding a volume of the GO solution to a larger volume of the DP solution. In this circumstance spontaneous self-assembly is initiated, but the resultant graphene oxide-protein structure may be in the form of a membrane, a 2D sheet, a gel or an aggregate and the formation of tubular structures is not observed. These structures may be collapsed or may not comprise a lumen. It is therefore preferred to add the DP solution into the GO solution in order to form tubes or other 3D structures comprising a lumen.

The graphene oxide-protein matrices as described herein are dynamic, enable opening and controlled anisotropic growth, and are highly stable. The matrices can withstand large temperature changes exhibiting no apparent effects on their multi-layered structure when the temperature drops below the transition temperature or rises far above the transition temperature (Tt) of the DP. In fact, once formed the GO-protein matrices can be heated to about 1000° C. and still retain their multilayer structure. This enhanced stability is also evidenced by the capability to co-assemble capillary-like structures as small as about 10 μm in internal diameter and with walls as thin as about 5 μm in thickness (FIG. 2c).

The GO sheets as described herein may be present throughout the cross-section of the membrane. The disordered protein may also be present throughout the membrane, as evidenced by the adhesive properties of the membrane and by electron and fluorescence microscopy.

Graphene oxide is a carbon-based compound formed of various ratios of carbon, oxygen, and hydrogen. It may be obtained by treating graphite with strong oxidizers, such as sulphuric acid, to make graphite oxide (also known as graphitic oxide or graphitic acid). Graphene oxide is effectively a by-product of this oxidisation as when the oxidising agents react with graphite, the interplanar spacing between the layers of graphite is increased. The completely oxidised compound can then be dispersed in a base solution such as water which yields graphene oxide in monomolecular sheets comprising carbon atoms arranged in a hexagonal lattice. Graphene oxide is chemically similar to graphite oxide, although structurally very different as they have different interplanar spacing between the individual atomic layers of the compounds, caused by water intercalation. It is also possible to modify the surface of graphene oxide to change its properties. Graphene oxide can be further reduced into reduced Graphene oxide (rGO) or graphene.

Figure 7:
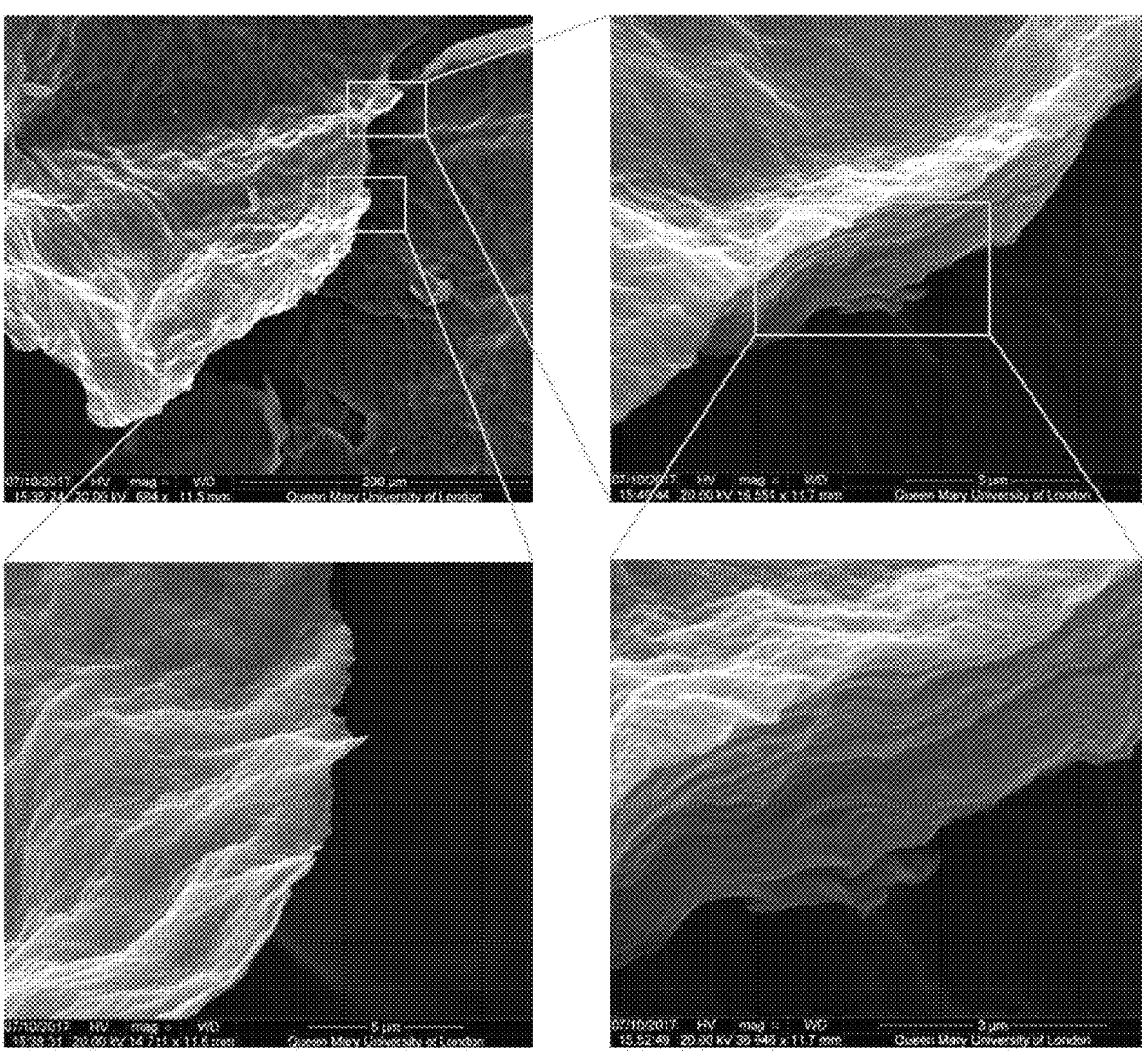

Reduction of graphene oxide can be achieved by heating the GO to 1000° C. to make graphene, which has very high electrical conductivity. This can be done to the GO whilst it is in the GO-protein matrix. A method of reducing GO comprises the step of raising the temperature of the structures, once formed, to about 1000° C. This "reduces" the GO to make Graphene. The multi-layered membrane remains present above 1000° C. The membranes become electrically conductive once the GO is reduced to graphene, which means that GO can be successfully reduced into graphene while still maintaining the multi-layered 3D structure. This means the methods as described herein can be used to build complex conductive structures. This is also referred to as carbonisation of the structure (FIG. 7). Accordingly, in some embodiments, reduced graphene oxide is used to form the matrices, and/or the graphene oxide is reduced once it is already present in the matrix. In some embodiments, GO in the 3D structures can be reduced by heating the DP-GO structure in ethanol. For example, GO in the 3D structures can be reduced by heating the DP-GO structure in 70% ethanol at 80° C. for more than about 8 h. The integrated tubular structure is found to be retained after this procedure (see FIG. 19). This has applications for methods and products requiring semiconductive and conductive materials. In biology neurons and cardiac cells are electrically stimulated for example and other types of devices can be created that integrate benefits from the semiconductive industry (GO) as well as from biological systems (proteins).

Graphene oxide sheets as described herein are about 1.1±0.2 nm thick. In some embodiments graphene oxide sheets may be between about 0.5 nm and about 1.5 nm thick, or between about 0.9 nm and about 1.3 nm thick. In some embodiments graphene oxide sheets may be 0.9 nm thick, or 1 nm thick, or 1.1 nm thick, or 1.2 nm thick or 1.3 nm thick. The edges of each sheet are terminated with carboxyl and carbonyl groups. The GO sheets have a net negative charge. The GO sheets typically have a hydrophobic surface area.

As described herein, GO sheets of two different average lateral sizes may be used, including larger GO (GO-L) measuring 10.5±4.5 μm and smaller GO (GO-S) of 2.3±0.9 μm, both exhibiting a typical hydrophobic surface and negatively charged carboxylic groups on their periphery.

An aqueous solution of GO, as described herein, may comprise GO at a concentration of from about 0.01% wt/vol to about 0.5% wt/vol, or preferably from about 0.01% wt/vol to about 0.2% wt/vol. In an aqueous solution of GO as described herein, the solvent may be water or another water-based medium such as an aqueous cell culture medium or an aqueous buffer solution (such as phosphate-buffered saline (PBS)).

The disordered protein (DP) as described herein may preferably be an elastin-like polypeptide (ELP). ELPs are also known as elastin-like recombinamers (ELRs) or elastin-like polymers. As described herein, ELPs are disordered proteinaceous polymers which are based on the recurrence of certain short monomers that are considered as "building blocks" in natural elastin due to their striking repetition with no or little variation along its sequence. ELPs are normally rich in amino acids such as glycine (G), valine (V) and proline (P). ELPs are generally based on an amino acid pentamer as the monomer. ELPs, as described herein, comprising the amino acid pentamer motif Val-Pro-Gly-X-Gly (VPGXG)$_n$, wherein X is any amino acid apart from proline, and n is from about 2 to about 50.

These ELP molecules exhibit a reversible-phase transition with a change in temperature and have been used to create biocompatible materials. Their Tt can be easily altered by varying the amino acid sequence and bio-activity can also be added via the incorporation of specific peptide domains.

For example, many ELPs are based on the pentamer VPGVG (as monomer) or modifications of this in which one or more amino acids have been substituted by other natural or modified amino acids. Therefore, preferably, the ELPs comprise a polymer of the pentamer VPGVG and/or a pentamer in which one or more (e.g. two or three) amino acids have been substituted by other natural or modified amino acids. The ELPs may comprise a polymer formed from more than one pentamer.

The ELPs are charged. The ELPs may be negatively charged or positively charged. The ELPs may be negatively charged. More preferably, the ELPs are positively charged. The charge polarity and zeta potential should be opposite to that of the GO. The difference between the charge of the GO and the charge of the DP may be marginal.

The DP may be charged. The DP solution may be charged. The DPs may be negatively charged or positively charged. The DP solutions may be negatively charged or positively charged. Preferably, the DPs are positively charged. Preferably, the DP solutions are positively charged. The charge polarity and zeta potential of the DP should be opposite to that of the GO. The charge polarity and zeta potential of the DP solution should be opposite to that of the GO.

The DP may be polymer with a repeating unit. The polymer may comprise a repeating unit (such as a pentamer) which contains a negatively charged amino acid such as aspartic acid (D) or glutamic acid (E). The polymer may comprise a pentamer which contains a positively charged amino acid such as histadine (H), lysine (K) or arginine (R). For example, the amino acid X in one or more of the repeating pentamers may be a positively charged amino acid. As described herein at least about 15%, at least about 20% or at least about 50% of the repeating pentamers may be positively charged.

The ELPs may comprise a plurality of hydrophobic regions. For example, one or more of the repeating pentamers may be hydrophobic. Wherein the repeating unit of the ELP comprises the amino acid X in one or more of the repeating units (such as pentamers), the amino acid X may be a hydrophobic amino acid, for example such as glycine, alanine, valine, leucine, isoleucine, phenylalanine, methionine, or tryptophan. This helps in the self-assembly of the 3D structures. It also allows an opening to be formed in the membrane by way of an aperture forming in the lumen, which allows the formation of different tube geometries. For example, at least 50%, or at least 80% of the repeating pentamers may be hydrophobic.

The ELPs may have a critical temperature (also referred to in the art as a transition temperature—Tt) at which phase transitional behaviour occurs. Below this temperature, the polymer chains may remain disordered, relatively extended, in solution if they are not crosslinked, and fully hydrated mainly by hydrophobic hydration. On the contrary, above the Tt, the polymer chain may hydrophobically fold and assemble to form a phase separated state in which the chains adopt a dynamic structure, called 13-spiral, involving one type II 0-turn per pentamer, and stabilized by intraspiral inter-turn and inter-spiral hydrophobic contacts. The ELPs may have a Tt of from about 0° C. to about 100° C., or from about 5° C. to about 70° C., or from about 25° C. to 45° C.

The disordered proteins as described herein may have a transition temperature. When a disorder protein has a transition temperature as described herein, GO-protein matrices may be formed at or above the transition temperature.

Particular pentamers which can be used in the formation of an ELP preferably include but are not limited to VPGIG and VPGKG.

Other pentamers which can be present in an ELP include but are not limited to VPGVG, VPGDG, VPGEG, VGIPG and VPGIG.

As described herein, the ELPs may comprise a polymer comprising, as a monomer, one or more pentamers selected from VPGIG, VPGKG or (VPGXG)$_n$ wherein X is any amino acid other than proline and n is from about 2 to about 50.

In other embodiments, the ELPs comprise a polymer comprising, as monomers, two or more pentamers selected from VPGIG, VPGKG or (VPGXG)$_n$ wherein X is any amino acid other than proline and n is from about 2 to about 50.

The polymer may contain the pentamers in the following ratios relative to each other:

a) VPGIG: 40-80 b) VPGKG: 20-60

It has been found that ELPs with these ratios of components may be especially good at forming self-assembling graphene oxide-protein matrices, 3D structures and tubes as described herein.

The ELPs may comprise additional components as part of the polymer in addition to the monomers (e.g. pentamers). For example, the ELPs may comprise a bioactive domain to elicit a specific biological effect. The ELPs may comprise a plurality of bioactive domains. The bioactive domain may be a peptide sequence. The bioactive domain may cause cell adhesion. For example, the peptide sequence RGD can be inserted into the ELP as a cell adhesion domain.

As described herein, the ELP may be ELR-IK24 (also referred to herein as ELK1). The sequence of ELK1 may comprise or consist of: MESLLP-(VPGIG VPGIG VPGKG VPGIG VPGIG)$_n$, wherein n is greater than 5. Preferably the sequence of ELK1 may comprise or consist of: MESLLP-(VPGIG VPGIG VPGKG VPGIG VPGIG)$_{24}$.

ELK1 is positively charged. ELK1 has a transition temperature of 30° C. ELK1 has a molecular weight of 51.9 kDa. ELK1 is particular preferred for forming self-assembling graphene oxide-protein matrices, 3D structures and tubes as described herein.

Table 1 shows the percentage of secondary structure found in ELK1 at (30° C.), above (45° C.) and below (4° C.) its Tt, alone and when in complex with GO. ELK1 will form GO-protein matrices at, above or below its Tt. Most preferably ELK1 will be used to form GO-protein matrices at its Tt of 30° C.

TABLE 1

| | ELK1 | | | | | ELK1-GO | | | |
|---|---|---|---|---|---|---|---|---|---|
| T (° C.) | α-helix (%) | ß-sheet (%) | Random (%) | ß-turn (%) | T (° C.) | α-helix (%) | ß-sheet (%) | Random (%) | ß-turn (%) |
| 4 | 8.6 | 45.5 | 40.5 | 11.4 | 4 | 14.8 | 33.2 | 44.3 | 7.7 |
| 30 | 16.8 | 35.5 | 37.6 | 10.1 | 30 | 15.1 | 41.2 | 34.8 | 8.4 |
| 45 | 8.2 | 38.2 | 46.6 | 7.0 | 45 | 15.5 | 37.8 | 39.2 | 7.5 |

A protein, as described herein, means, in general terms, a plurality of amino acid residues joined together by peptide bonds. It is used interchangeably and means the same as peptide, or polypeptide, and includes glycoproteins and derivatives thereof. The term "protein" is also intended to include fragments, analogues and derivatives of a protein wherein the fragment, analogue or derivative retains essentially the same biological activity or function as a reference protein.

The fragment, derivative or analogue of the protein may be (i) one in which one or more of the amino acid residues are substituted with a conserved or non-conserved amino acid residue (preferably, a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence which is employed for purification of the polypeptide. Such fragments, derivatives and analogues are deemed to be within the scope of those skilled in the art from the teachings herein.

Particularly preferred are variants, analogues, derivatives and fragments having the amino acid sequence of the protein in which several e.g. 5 to 10, or 1 to 5, or 1 to 3, 2, 1 or no amino acid residues are substituted, deleted or added in any combination. Especially preferred among these are silent substitutions, additions and deletions, which do not alter the properties and activities of the protein of the present invention. Also especially preferred in this regard are conservative substitutions.

An example of a variant of the present invention is a disordered protein as defined herein, apart from the substitution of one or more amino acids with one or more other amino acids. The skilled person is aware that various amino acids have similar properties. One or more such amino acids of a substance can often be substituted by one or more other such amino acids without eliminating a desired activity of that substance.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains that may be charged); aspartate and glutamate (amino acids having acidic side chains); asparagine and glutamine (amino acids having amide side chains that may be charged); and cysteine and methionine (amino acids having sulphur containing side chains). The amino acids glycine, alanine, valine, leucine, isoleucine, proline, phenylalanine, methionine, and tryptophan have hydrophobic, non-polar side chains. The amino acids serine, threonine, asparagine and glutamine, have hydrophilic side chains. The amino acids serine, threonine, cysteine, asparagine, glutamine, and tyrosine have polar side chains.

Substitutions of this nature are often referred to as "conservative" or "semi-conservative" amino acid substitutions.

Amino acid deletions or insertions may also be made relative to the amino acid sequence for the fusion protein referred to above. Thus, for example, amino acids which do not have a substantial effect on the activity of the polypeptide, or at least which do not eliminate such activity, may be deleted. Such deletions can be advantageous since the overall length and the molecular weight of a polypeptide can be reduced whilst still retaining activity. This can enable the amount of polypeptide required for a particular purpose to be reduced—for example, dosage levels can be reduced.

Amino acid insertions relative to the sequence of the disordered protein above can also be made. This may be done to alter the properties of a substance of the present invention (e.g. to assist in identification, purification or expression).

Amino acid changes relative to the sequence for the disordered protein of the invention can be made using any suitable technique e.g. by using site-directed mutagenesis. It should be appreciated that amino acid substitutions or insertions within the scope of the present invention can be made using naturally occurring or non-naturally occurring amino acids. Whether or not natural or synthetic amino acids are used, it is preferred that only L-amino acids are present.

A protein according to the invention may have additional N-terminal and/or C-terminal amino acid sequences. Such sequences can be provided for various reasons, for example, glycosylation.

"Identity" as known in the art is the relationship between two or more polypeptide sequences or two or more polynucleotide sequences, as determined by comparing the sequences. In the art, identity also means the degree of sequence relatedness (homology) between polypeptide or polynucleotide sequences, as the case may be, as determined by the match between strings of such sequences. While there exist a number of methods to measure identity between two polypeptide or two polynucleotide sequences, methods commonly employed to determine identity are codified in computer programs. Preferred computer programs to determine identity between two sequences include, but are not limited to, GCG program package (Devereux, et al., Nucleic acids Research, 12, 387 (1984), BLASTP, BLASTN, and FASTA (Atschul et al., J. Molec. Biol. 215, 403 (1990).

Proteins, as described herein, have a hierarchical structure. The primary structure of a protein, as described herein, is the linear arrangement, or sequence, of amino acid residues that constitute the polypeptide chain. The secondary structure of a protein refers to the organisation of the polypeptide chain, which can assume several different spatial arrangements.

Without stabilising interactions, such as hydrogen bonds, a polypeptide assumes a random coil structure. A random coil, as described herein, is a protein conformation in which the amino acids are oriented randomly while still being bonded to adjacent units. In other words, they lack secondary structure and are only defined by their primary structure.

When stabilising hydrogen bonds form between amino acid resides the amino acid backbone folds to form α-helices and β-sheets.

An alpha (α) helix, as described herein, is a right-handed spiral conformation (helix) stabilized by hydrogen bonds between the NH and CO groups of the polypeptide chain. More specifically, every backbone N—H group donates a hydrogen bond to the backbone C═O group of the amino acid located four residues earlier (towards the C-terminus) along the amino acid sequence. The hydrophobic or hydrophilic quality of the helix is determined by the amino side chains, which point outwards, because the polar groups of the peptide backbone are already involved in hydrogen bonding in the helix and are therefore unable to affect its hydrophobicity or hydrophilicity.

A beta (ß) sheet (also known as a ß-pleated sheet), as described herein, consists of laterally packed R strands. Each β strand is a short (5-8 amino acid residue) polypeptide chain that is nearly fully extended. Hydrogen bonding between backbone atoms in adjacent β strands, within either the same or different polypeptide chains, forms a β sheet. β strands have a polarity defined by the orientation of the peptide bond. Adjacent β strands can be oriented antiparallel or parallel with respect to each other. In both arrangements of the backbone, the side chains project from both faces of the sheet.

Turns, as described herein, are U-shaped secondary structures comprising short sequences of amino acid residues (for example, 3 amino acids or 4 amino acids) stabilised by a hydrogen bond between their end residues. A β turn (also known as β turns, β-turns, β-bends, tight turns, reverse turns or Venkatachalam turns) consist of 4 amino acid residues wherein the C═O group of the first amino acid is hydrogen bonded to the N—H group of the $3^{rd}$ amino acid. A β turn, as described herein, causes a change in direction of the polypeptide chain.

Tertiary structure of a protein, as described herein, defines the overall three-dimensional spatial arrangement of all amino acid residues in a protein. Tertiary structure is stabilised by hydrophobic interactions between the nonpolar side chains and, in some proteins, by disulfide bonds. These stabilizing forces hold the α helices, β strands, turns, and random coils in a compact internal scaffold.

Quaternary structure of a protein, as described herein, is the arrangement and number of multiple protein or biomolecular subunits in a complex.

Disordered proteins, as described herein, lack a fixed or ordered 3D structure, or comprise a substantial portion that lacks a fixed or ordered 3D structure (i.e. secondary structure). Disordered regions of proteins may be said to exist in a random coil format. This can include proteins that are fully or partially unstructured and may contain disordered regions. Disorder can be found in intrinsically disordered regions within an otherwise well-structured protein. The term disordered protein (DP) as described herein therefore includes proteins that contain disordered regions as well as fully disordered proteins.

DPs as described herein may change their conformation. DPs may adopt a fixed 3D structure after binding to other macromolecules. This transition to a more ordered state can involve a few interacting residues, or it might involve an entire protein domain. Certain disordered regions serve as "molecular switches" in regulating certain biological function by switching to ordered conformation upon molecular recognition such as; small molecule-binding, DNA/RNA binding and ion interactions. Some disordered proteins retain their disorder or conformational freedom even when they bind specifically to other proteins.

Such disordered regions as described herein can include flexible regions, linkers or loops that may link different domains. Flexible linkers allow the connecting domains to freely twist and rotate to recruit their binding partners via protein domain dynamics. They also allow their binding partners to induce larger scale conformational changes by long-range allostery.

Other disordered regions as described herein can include linear motifs. Linear motifs are short, disordered segments of proteins that may mediate functional interactions with other proteins or biomolecules such as RNA, DNA or sugars. Linear motifs may have roles in cell regulation and are often post-translationally modified. Many DPs contain pre-structured linear motifs that are transient secondary structural elements primed for target recognition. These transient structures can become full and stable secondary structures, e.g., helices, upon target binding. Short linear motifs, short stretches of protein sequence that mediate protein-protein interaction, are often over-represented in disordered proteins.

Many disordered proteins as described herein comprise regions without any regular secondary structure and have a low content of predicted regular secondary structure. These regions are also known as flexible regions.

DPs as used herein may comprise a large percentage of random coil structure. DPs as used herein may comprise a large percentage of random coil structure prior to admixing with GO. In some embodiments disordered proteins may preferably comprise at least 35% random coil structure. In some embodiments disordered proteins may comprise at least 20%, at least 30%, at least 35%, at least 40%, at least 50%, at least 60% or at least 70% random coil structure.

Prior to matrix assembly, DPs may comprise at least 35% random coil structure and at least 5% α-helical structure.

The disordered protein as described herein may comprise a greater percentage of random coil structure than percentage of ß-sheet structure.

The disordered protein as described herein may increase its percentage of ß-sheet structure when complexed with GO.

The disordered protein as described herein may comprise at least 10%, at least 20%, at least 30%, at least 40%, at least 50% ß-sheet structure.

The disordered protein as described herein may comprise less than 10%, less than 12%, less than 14%, less than 16%, less than 18%, less than 20%, less than 30% or less than 40% ß-turn structure.

The disordered protein as described herein may comprise at least 5%, at least 10%, at least 20%, at least 30% or at least 40% α-helix structure.

In some embodiments, prior to matrix assembly, the disordered proteins may comprise at least 35% random coil structure, at least 5% α-helical structure, and a greater percentage of random coil structure than percentage of ß-sheet structure. Additionally, the disordered protein may increase its percentage of ß-sheet structure when complexed with GO.

If the DP exhibits a transition temperature, the method may be conducted at or above the transition temperature of the DP. For example, this may be case if the protein only exhibits the appropriate relative amounts of random coil, α-helical structure and ß-sheet structure at or above its transition temperature.

Disorder, as described herein, can be predicted with high accuracy using disorder prediction algorithms based on the primary amino acid sequence composition, physiochemical properties of amino acids, structural information such as linear motif sites and other parameters such as comparison to X-ray crystallography or NMR protein databases. Exemplary disorder prediction software available includes; SLIDER (Super-fast predictor of proteins with Long Intrinsically DisordERed regions—Peng et al, (2014) Proteins: Struc, Func, and Bioinf, 82(1): 145-158) or PONDR (Predictor of Natural Disordered Regions—Molecular Kinetics, Inc.). A person skilled in the art would be able to select and use the relevant method or computer software to predict whether a certain protein is disordered or contains disordered regions.

Disordered proteins as described herein also comprise low complexity sequences. Low complexity sequences are sequences with over-representation of a few residues.

DPs as described herein are characterised by a low content of bulky or hydrophobic amino acids and a high proportion of polar, charged and hydrophilic amino acids.

For example, the following amino acids alanine, arginine, glycine, glutamine, serine, proline, glutamic acid and lysine may be characterised as "disorder-promoting amino acids". The amino acids tryptophan, cysteine, phenylalanine, isoleucine, tyrosine, valine, leucine, and asparagine are characterised as "order-promoting amino acids". Amino acids histidine, methionine, threonine and aspartic acid are ambiguous, found in both ordered and unstructured regions.

The DPs, as described herein, may be a naturally occurring protein or may be a synthetic protein. The skilled person is familiar with methods of sourcing, extracting, isolating and purifying proteins from their source. Naturally occurring proteins as described herein may also be synthesised or expressed by methods known in the art rather than extracted from the natural source. The skilled person is also familiar with methods of designing and synthesising proteins. Synthetic proteins may have genetic sequences not found in naturally occurring proteins or may mimic the structure and function of the naturally occurring protein.

The disordered protein, as described herein, may comprise a polypeptide having a repeating amino acid sequence motif. The polypeptide may be a polymer comprising monomers wherein the monomers are the repeating amino acid sequence motif. The repeating amino acid sequence motif (the monomer) may be comprised of from about 2 to about 30 amino acids, or from about 2 to about 15 amino acids, or from about 2 to about 10 amino acids, or 3, 4, 5, 6, 7, 8, 9, 10, 11, 12, 13, 14 or 15 amino acids. The repeating amino acid sequence motif (the monomer) may be repeated from about 2 to about 50 times within the molecule. Preferably, the repeating amino acid sequence motif (the monomer) is a pentamer, comprises a sequence of 5 amino acids (a pentamer). The monomer may comprise a general formula wherein one or more amino acids may be substituted for other amino acids. The monomers in the polymer may be identical to the other monomers or the polymer may comprise multiple monomers of the same general formula wherein there may be different amino acid substitutions in each monomer.

In some embodiments, the molecular weight of the DPs (such as ELPs) range from about 2 kDa to about 400 kDa. In some embodiments, the molecular weight of the DPs (such as ELPs) range from about 5 kDa to about 300 kDa. In other embodiments, the molecular weight of the DPs (such as ELPs) range from about 10 kDa to about 250 kDa.

The DPs (such as ELPs) may exhibit the preferred relative amounts of alpha-helix, B-sheet and random coil components as discussed herein.

The DPs may have an average molecular weight of from about 2 kDa to about 55 kDa. In some embodiments, the DPs may have an average molecular weight of from about 10 kDa to about 55 kDa.

Resilin, as described herein, is an elastic polymer found primarily in arthropods and insects. Elastic proteins or elastomers are defined as polymers that display rubber like elasticity and possesses viscoelasticity (i.e., both viscosity and elasticity) and very weak intermolecular forces, and generally low Young's modulus and high failure strain compared with other materials. It provides elastic properties to mechanically active tissues.

Resilin is one of the most efficient elastic proteins (very little of the stored energy is lost as heat). It is comprised primarily of random coil structures and has little or no secondary structure. This confers elasticity. Resilin has a transition temperature of 40° C. and a molecular weight of 18.9 kDa. Resilin is a disordered protein; however its segments may take on secondary structures under different conditions. It may take on secondary structure such as the polyproline helix indicated by the high occurrence of proline and glycine in some resilin domains. Resilin contains a number of repeating amino acid sequence motifs. The sequence of the DP may comprise or consist of MSKGP-(GRGDQPYQ)$_n$ wherein n is at least 5, preferably wherein n is 20.

The disordered protein as described herein may be resilin. The aqueous solution of resilin may comprise resilin at a concentration of from about 0.2% wt/vol to about 7.5% wt/vol, or preferably from about 0.5% wt/vol to about 3% wt/vol. For aqueous solutions of resilin the solvent is water or another water based medium such as cell culture medium or a buffer solution such as phosphate-buffered saline (PBS). The pH of the aqueous solution comprising resilin may from about pH 6.0 to about pH 9.0, or preferably from about pH 7.0 to about pH 8.0.

Table 2 shows the percentage of secondary structure found in resilin at and below its Tt, alone and when in complex with GO. Resilin may form GO-protein matrices at or above its Tt.

TABLE 2

| | Resilin | | | | | Resilin + GO | | | |
|---|---|---|---|---|---|---|---|---|---|
| Temperature (° C.) | ß-sheet (%) | ß-turn (%) | Random (%) | α-helix (%) | Temperature (° C.) | ß-sheet (%) | ß-turn (%) | Random (%) | α-helix (%) |
| <Tt | 57.4 | 0.8 | 38.4 | 3.2 | <Tt | 28.6 | 16.1 | 50.9 | 4.3 |
| >Tt | 12.8 | 3.8 | 69.0 | 15.3 | >Tt | 46.3 | 4.3 | 45.2 | 4.2 |

An aqueous solution of DP, as described herein, may comprise DP at a concentration of from about 0.2% wt/vol to about 7.5% wt/vol, or preferably from about 0.5% wt/vol to about 3% wt/vol wherein the solvent is water or another water-based medium such as cell culture medium or a buffer solution such as phosphate-buffered saline (PBS).

The ratio of concentration of DP solution to concentration of GO solution may be at least about 10:1 or preferably at least about 15:1.

A GO-protein matrix may be formed by admixing a DP solution of from about 0.2% wt/vol to about 7.5% wt/vol with a GO solution of from about 0.01% wt/vol to about 0.5% wt/vol, providing the ratio of concentration of DP solution to concentration of GO solution is at least about 10:1 or preferably at least about 15:1.

Preferably, a GO-protein matrix may be formed by admixing a DP solution of from about 0.5% wt/vol to about 3% wt/vol with a GO solution of from about 0.05% wt/vol to about 0.2% wt/vol, providing the ratio of concentration of DP solution to concentration of GO solution is at least about 10:1 or preferably at least about 15:1.

The graphene oxide-protein matrix as described herein can spontaneously self-assemble into tubes. These tubes or tubular microstructures as described herein are formed by a method comprising admixing an aqueous solution of a disordered protein (DP) with an aqueous solution of graphene oxide (GO).

A tube as described herein may be a hollow, cylindrical shape with a central lumen capable of holding or transporting something, for example a liquid or a gas. A tube as described herein may have a circular cross section. A tube as described herein may have a semi-circular cross section. A tube as described herein may have one or more apertures in the lumen, creating openings. The tube may be open at one or more ends or it may be closed. A tube as described herein may be branched or bifurcated and may be capable of connection or communication with other tubes or objects to form complex tubular networks or bridges. A tube can also be functional when not holding or transporting anything, for example as a hollow "bridge" to allow travel from end to the other, for example by cells or exosomes.

The features and mechanical properties of such tubes may be assessed by assessing tube geometry visually and robustness manually or by carrying out nanotensile tests. Such tensile tests can be performed on the graphene oxide-protein matrices, such as tubes, to test if the mechanical properties changed with differing concentration of GO. Samples with a GO concentration of 0.10% wt/vol are stiffer (and the elastic modulus higher) than other samples tested. Apart from the elastic modulus, the other mechanical properties such as the strength, the strain at break, and the toughness modulus increase when increasing the GO concentration. However, these preliminary results suggest that samples with 0.10% GO could exhibit higher stiffness without compromising its strain and dissipated energy. A preferred concentration of GO solution may be 0.1% wt/vol.

As described herein, the aqueous solution of DP may be introduced to the aqueous solution of GO under pressure. This may be positive pressure or negative pressure. This may be via injection, pipetting, immersion, a drop or via the use of negative pressure to introduce the DP solution to the GO solution. The aqueous solution of DP, as described herein may be injected slowly into a larger volume of the aqueous solution of GO. This may be achieved by using a hand-held pipette, syringe or nozzle, or by automating the process and using a computer operated nozzle, syringe or pipette to inject the DP into the GO. The injection device may be moved slowly in a pattern through the GO solution while injecting in order to form a tube of the corresponding shape (FIG. 2h). Such a method may also be used to create a tubular bridge between two surfaces by simply touching two distant surfaces while injecting the ELK1 solution into the GO solution (FIG. 2e). As the material touches a surface soon after co-assembly, it adheres, opens, and seals to the surface, enabling growth by continual injection of ELK1 solution until the next surface touch.

The 3D structures, as described herein, may also be formed by immersing a DP solution in a GO solution. For example, this may be by simply allowing a drop of DP solution to fall in a GO solution, wherein gravity provides the pressure behind the introduction of DP solution to GO solution. Such a method may form a closed sac structure when a drop of, for example, ELK1 solution is immersed in a larger GO solution. This closed sac structure may open upon contacting an interface of the structure within the first seconds of formation, and grown and manipulated into longer tubes on demand by displacing said interface, for example by pulling on the tube (FIG. 2a). More GO solution may be added to smaller tubes to facilitate further growth. The method as described herein may further comprise the step of manipulating the 3D structure during formation so as to determine the final shape of the 3D structure.

The step of admixing the DP and GO solutions can also be carried out using an apparatus for 3D printing, such as a 3D printer or apparatus that has the capacity to administer one solution into another solution in a controlled manner and can execute the administration in a defined pattern. Such patterns could be determined by a computer program, such as 3D printing software which may also comprise operator input. In this way the tubes, as described herein, may be printed quickly and easily into any configuration, such as tubular networks, microfluidic devices, capillaries, blood vessels, tubules or connective tissues.

This may provide valuable progress into the possibility of 3D printing artificial organs meets a need in the art since artificial organs such as livers and kidneys made by 3D bioprinting have been shown to lack elements that may be crucial such as working blood vessels, and tubules, for example for collecting urine. Without these components the body has no way to get the essential nutrients and oxygen to the entire artificial organ.

As described herein, the pH of the DP solution is preferably from about pH5 to about pH9. The pH of the DP solution may be, for example, pH 4.0, 5.0, 6.0, 7.0, 7.5, 8.0 or 9.0.

As described herein, the pH of the GO solution is preferably from about pH 2 to about pH 6. The pH of the GO solution may be, for example, pH 2.0, 3.0, 4.0, 5.0, or 6.0.

To further explore the role of electrostatic forces, tubes were formed with ELR and GO solutions at varying pHs and it was found that more robust tubes formed when the zeta potential or charge difference between the GO and DP components was marginal (FIG. 4c, d). The charge polarities and zeta potentials of the ELR and GO solutions are opposite, the charge and zeta potential of the DP is positive, and the charge and zeta potential of the GO is negative. These results suggest that optimum co-assembly does not solely depend on electrostatic forces but rather on a synergistic effect between both electrostatic and hydrophobic forces, which could be related to the 3D conformation of the DP and its ability to interact with the GO lamellae.

As described herein, a transition temperature (Tt) is the temperature at which a substance gains or loses a distinctive property, or changes from one crystal state to another. DPs as described herein, for example ELPs, may have a transition temperature and therefore have the capacity to change their conformation at different temperatures (FIG. 4e, graph). Below the transition temperature DPs may be disordered and above the transition temperature they may assume a more ordered, folded structure. Tubes, as described herein were formed at either below the transition temperature of the DP (for example, 4° C.), above the transition temperature of the DP (for example 45° C.), or at the transition temperature of the DP (for example, 30° C.) (FIG. 4e).

While tubes formed at all temperatures, they were more robust and exhibited better-defined multilayers and tubular geometry (FIG. 4e, images) at the transition temperature of the DP, suggesting stronger interactions at this temperature. This enhanced interaction was confirmed by DLS, which revealed the presence of larger DP-GO structures at the transition temperature compared to below the transition temperature and above the transition temperature (FIG. 40. These results indicate that the 3D conformation of the DP at the different temperatures determines its interaction with the GO lamellae, which would in turn play a role in the diffusion-reaction mechanism and consequently on the structure and properties of the resulting tubes (FIG. 4e, images).

The 3D structures, as described herein, may be formed at a temperature from about 4° C. to about 100° C., preferably from about 18° C. to about 75° C. The 3D structures may be formed above the transition temperature of the DP, below the transition temperature of the DP or at the transition temperature of the DP. Preferably the 3D structures are formed at or above the transition temperature of the DP.

The structures as described herein forms immediately upon mixing. However, immediately after co-assembly, it begins to strengthen as it assembles. There is generally no further change in the structural integrity/strength of the 3D structures after about 20 minutes of assembly. The thickness of the membrane described herein may reach its maximum thickness about 3 minutes after assembly. If the process is stopped earlier than 3 minutes, for example after 2 minutes, tubes with membranes of less than maximum thickness may still be formed. These thinner walled tubes are weaker tubes but still can be handled and are functional. The significance of this is that it is possible to form tubes defined by thin membranes (for example at least about 5 μm) or thicker membranes (for example from at least about 50 μm to at least about 10 cm) using the methods described herein by modulating the amount of time the DP and GO solutions are allowed to admix for. For a thicker membrane, the DP and GO solution can be allowed to interact for a longer time period, for example from about 3 to about 60 minutes. For a thin membrane, the DP and GO solution can be allowed to interact for a shorter time period, for example from about 1 to about 3 minutes. FIG. 2c, for example, shows membranes about 10 μm in thickness.

Modifying the amount of GO used provides another way to modulate the membrane thickness. In some embodiments, increasing the concentration of GO that is admixed with DP increases the thickness of the membrane. In some embodiments, decreasing the concentration of GO that is admixed with DP decreases the thickness of the membrane.

For a thicker tubular wall membrane, the concentration of GO used may be increased, for example to 0.10% GO-2% ELK1 or 0.15% GO-2% ELK1. Fora thinner tubular wall membrane, the concentration of GO used may be decreased, for example to 0.05% GO-2% ELK1 (see FIG. 11).

The DPs and the GOs as described herein may have opposite charges. GO generally has a net negative charge due to the negatively charged carboxylic groups on the periphery of the GO sheets. The GO solution generally has a net negative charge due to the negatively charged carboxylic groups on the periphery of the GO sheets.

Preferably the DP as described herein will have a net positive charge. At a pH below their isoelectric point (pI), proteins may carry a net positive charge; above their pI they may carry a net negative charge. The isoelectric point may be determined by determining the zeta potential ($\zeta$) of a material. Some DP molecules were found to be positively charged at pH values from 5 to 9, but negatively charged at pH 10. GO was found to be negatively charged at all tested pH values. The positive charge of the DP may arise as a result of the amino acid side chains comprising the protein.

The zeta potential ($\zeta$) of a material is a measurement of the electrokinetic potential between the surface of a solid particle immersed in a conducting liquid and the bulk of the liquid in a colloidal dispersion. The zeta potential is an indicator of the stability of colloidal dispersions (a mixture in which one substance of dispersed insoluble particles is suspended throughout another substance, normally a liquid). The magnitude of the zeta potential is an indication of the electrostatic repulsion between particles in a dispersion. Therefore, a high (negative or positive) zeta potential generally indicates stability and the dispersion or solution will resist aggregation. A small (negative or positive) zeta potential indicates the attractive forces of the particles may exceed the electrostatic repulsion causing the dispersion to aggregate. The zeta potential is partly caused by the net electrical charge.

Zeta potentials can be calculated using theoretical models known to those skilled in the art or measured, for example by using a Zetasizer (Nano-ZS ZEN 3600, Malvern Instruments, UK) at 30° C. under various pH conditions.

As described herein, the DP solution may have a positive zeta potential. The GO solution may have a negative zeta potential. The DP and GO solutions may have opposite zeta potentials wherein the DP solution has a positive zeta potential and the GO solution has a negative zeta potential.

The zeta potential of the DP solution may be from about −5 mV and about 15 mV. At pH values above about pH 9 DP the DP may be negatively charged and have a negative zeta potential. At pH values from about pH 5 to about pH9 the DP may be positively charged and have a positive zeta potential from about 5 mV to about 15 mV, preferably wherein the zeta potential is from about 6 mV to about 10 mV.

The zeta potential of the GO solution may be from about –0.1 mV and about –40 mV. At pH values from about pH 1 to about pH7 the GO is negatively charged and has a negative zeta potential. Preferably the zeta potential of GO solution is from about –20 mV to about –40 mV.

The DP solution may have a zeta potential of from about –5 mV and about 15 mV. The GO may have a zeta potential from about –0.1 mV and about –40 mV. Preferably the zeta potential of the DP solution is from about 6 mV to about 10 mV and the zeta potential of GO solution is from about –20 mV to about –40 mV.

Preferably the difference in zeta potentials of the GO solution and DP solution is small, while remaining opposite. For example, the difference between the zeta potentials of DP solution and GO solution may be less than 10 mV, or less than 30 mV, or less than 50 mV, or less than 70 mV.

Furthermore, the assembly or tubes and 3D structures as described herein can occur in salt-containing solutions such as cell culture media, which enables co-assembly in the presence of cells without affecting the structural integrity of the generated membrane. This capability opens new opportunities to grow robust geometrically complex tissue engineered constructs comprising and embedding cells in the absence of chemical crosslinking agents (FIG. 2d).

Cell culture media is a substance designed to support the growth of cells. It is usually a liquid or a gel and may comprise a source of energy, amino acids, vitamins, inorganic salts, glucose, cell cycle regulators, serum, a source of growth factors, hormones, and attachment factors. In addition to nutrients, the medium may also help maintain pH and osmolality and may further contain a buffering system which may be natural or chemical, such as PBS. The cell culture medium may contain antibiotics or other means for selection, if appropriate. Most cell culture media are aqueous as they may mimic biological conditions.

The ability of the graphene oxide-protein matrix as described herein to self-assemble in salt-containing solutions such as cell culture media, also enables co-assembly in the presence of other structures, or biological structures, without affecting the structural integrity of the generated membrane.

The methods as described herein may therefore comprise an additional step of adding additional structures to the 3D structure prior to, during or after admixing the DP and GO solutions. These structures may be embedded or localised to the 3D structure resulting from self-assembly.

The graphene oxide-protein matrix as described herein may further comprise additional structures.

These additional structures may be synthetic or may be biological. The additional structures may be vesicles, such as exosomes, liposomes, lysosomes, endosomes, secretory vesicles or transport vesicles. The additional structures may be nanostructures such as nanocapsules, nanocages, nanofibers, nanoflakes, nanoparticles, nanoshells, or quantum dots. The additional structures may be proteins such as membrane proteins, receptors, enzymes, cell adhesion molecules, proteoglycans hormones or growth factors. The additional structures may be a polymer such as a polysaccharide, a, DNA, RNA or heparan sulfate.

The graphene oxide-protein matrix as described herein may further comprise a vesicle, wherein the vesicle is a liposome.

The graphene oxide-protein matrix as described herein may further comprise a nanostructure, wherein the nanostructure is a nanocapsule or a quantum dot.

The graphene oxide-protein matrix as described herein may further comprise a protein, wherein the protein is a growth factor.

The graphene oxide-protein matrix as described herein may further comprise a polysaccharide, wherein the polysaccharide is heparan sulphate.

The graphene oxide-protein matrix as described herein may further comprise vesicles, wherein the vesicles are exosomes.

The methods described herein may therefore comprise a further step of adding any of the above additional structures to one of the DP or GO solutions prior to admixing them. The methods described herein may therefore comprise a further step of adding any of the above additional structures to the graphene oxide matrix whilst it is forming or after the matrix has formed.

These additional components may be localised to the inner surface or the outer surface of the membrane defining the lumen, or they may be embedded within the matrix.

Exosomes are extracellular vesicles released from cells upon fusion of vesicular bodies with the plasma membrane. Exosomes may provide a means of intercellular communication and of transmission of macromolecules, such as proteins, lipids, mRNA, miRNA and DNA and other signalling molecules, between cells. This may be due to their ability to bud off from one cell and merge with a distant cell, depositing their contents in the target cell. Exosomes may also contribute to the spread and development diseases. Exosomes have recently been found to be useful vectors for drugs because they are composed of cell membranes, rather than synthetic polymers, and as such do not invoke an immune response.

As described herein, exosomes may be added to the 3D structure prior, during or after admixing the DP and GO solutions and the exosomes may localise in or on the multi-layered membrane. (see FIG. 6).

The exosomes may be added at a concentration of from about $10^4$/ml to about $10^{10}$/ml. The exosomes may also be suspended in the DP or GO solutions prior to admixing.

The 3D structures as described herein have the capacity to embed, localise, and/or deliver the additional structure, such as exosomes. 3D structures such as membranes and tubes may be successfully assembled in the presence of the additional structures, such as exosomes which, upon GO-DP co-assembly, are localised within the multi-layered membrane. This further enhances the possibility to build structures that are bioactive and can deliver signalling molecules to cells.

The 3D structure as described herein may be permeable. The 3D structure, such as a tube, may allow for the flow or diffusion of small molecules (drugs, nutrients, water, ions or gases such as oxygen or carbon dioxide) or even exosomes or whole cells in and out of the tube. This may be very important for biomedical applications as enabling diffusion of nutrients, oxygen, waste materials, and cell migration may be critical. This permeability may be selective. This capacity allows the formation of functional capillaries.

Figure 14:
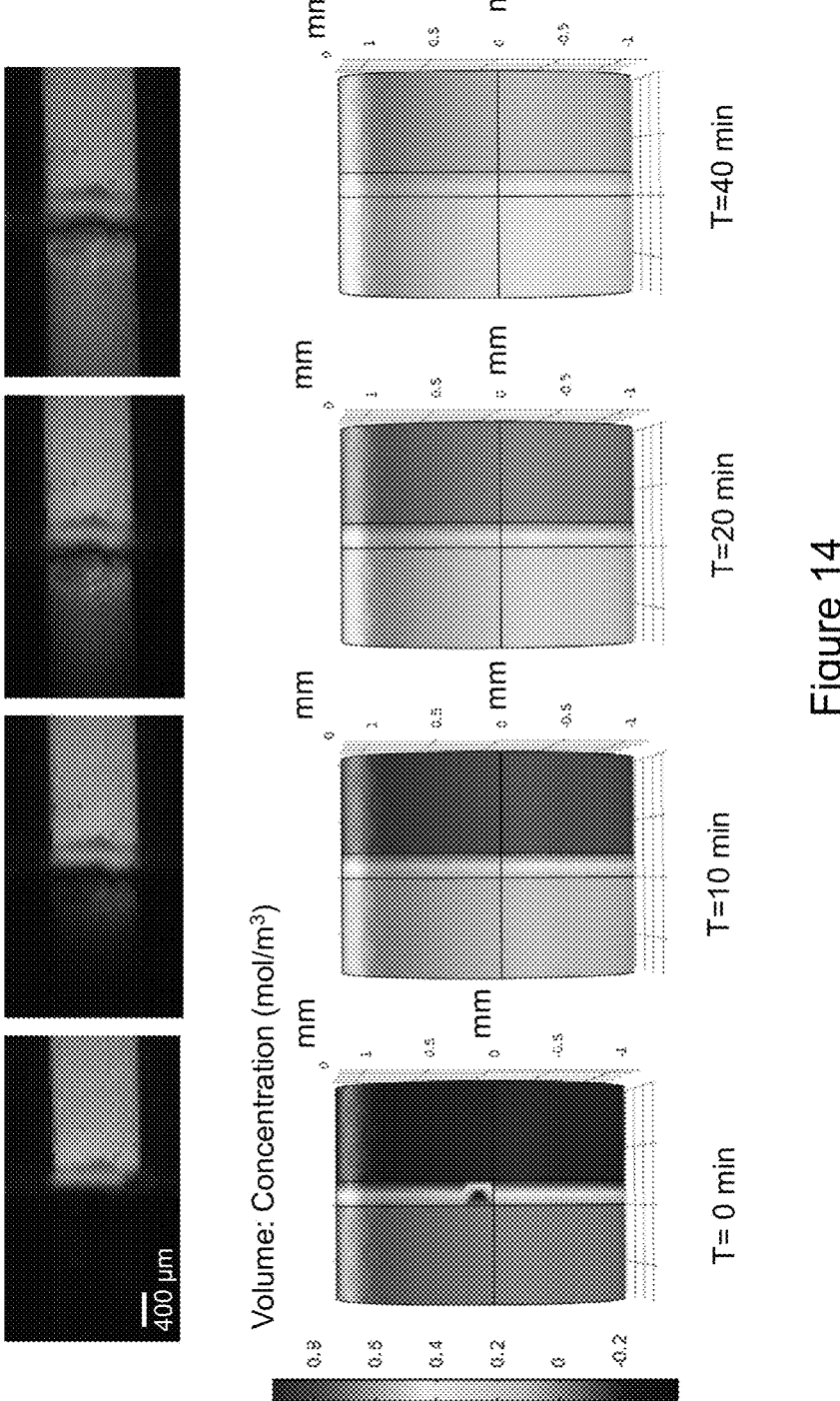
Figure 14:
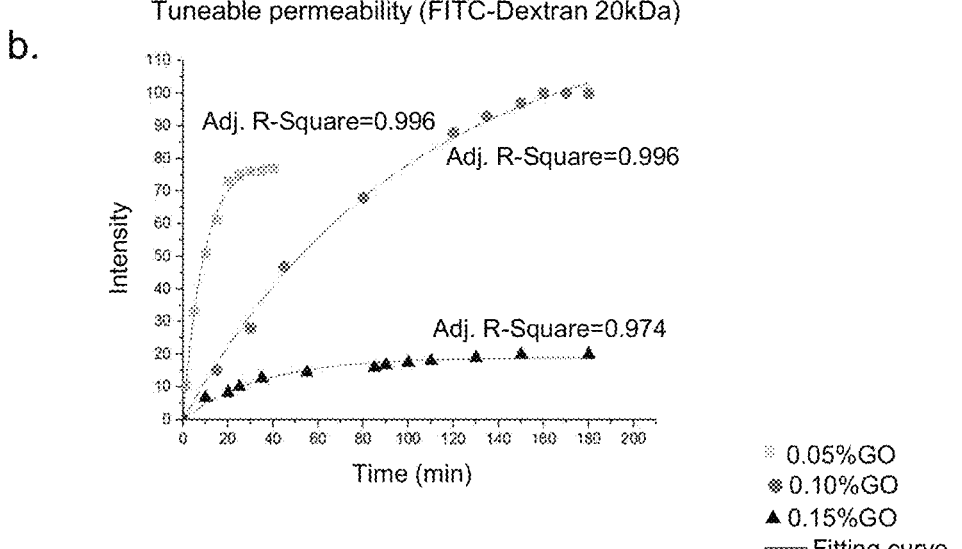
Figure 14:
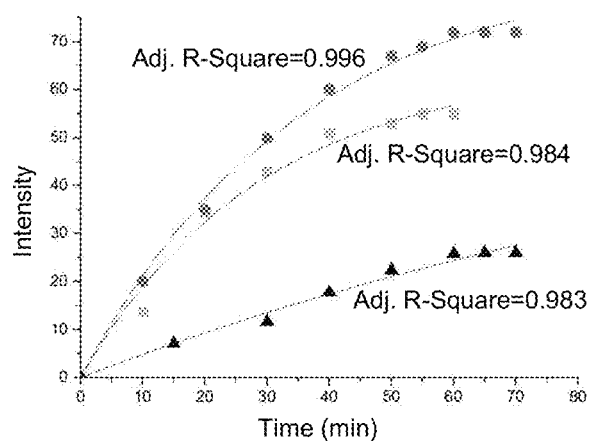
Figure 15:
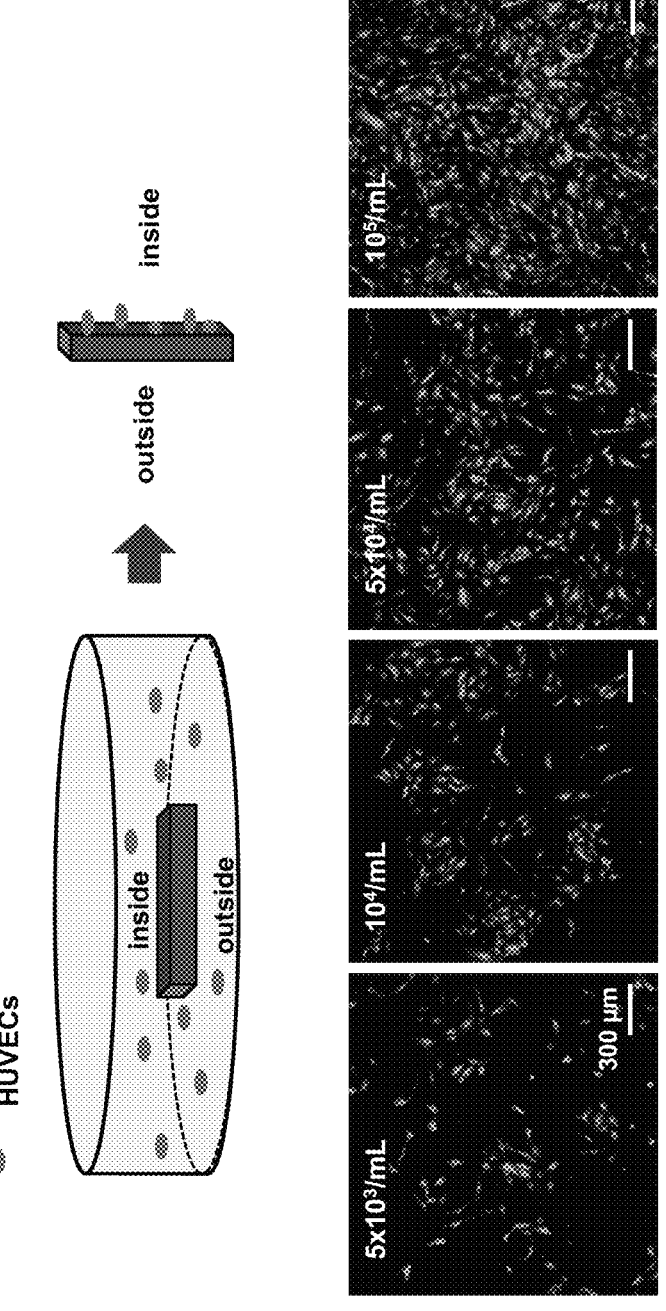
Figure 15:
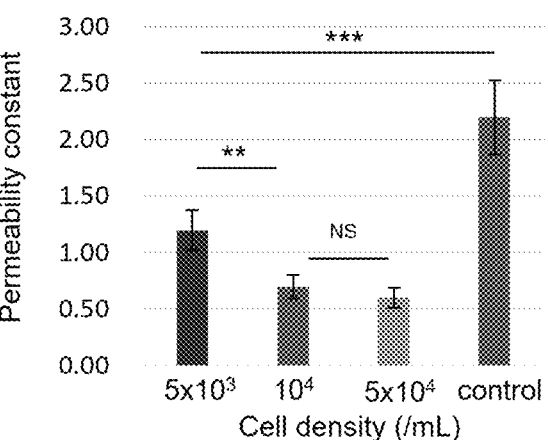
Figure 15:
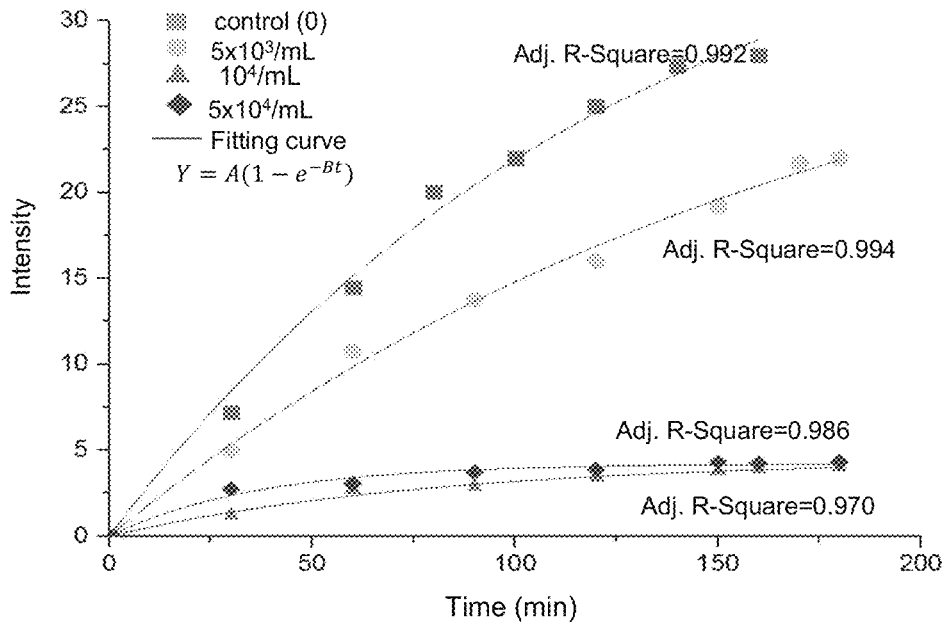

The 3D structures as described herein are not only permeable but the level of permeability and/or porosity can be modulated (see FIG. 13-15). The 3D structures described herein may comprise a tube with different levels of permeability along the long axis of the tube. This enables recreation of biological structures that have anisotropic structures.

The porosity and/or permeability of the 3D structure disclosed herein is tuneable by varying the GO concentration. The porosity of the 3D structures may decrease as the concentration of GO increases. In some embodiments decreasing the concentration of GO that is admixed with DP may increase the permeability of the 3D structure. In some embodiments increasing the concentration of GO that is admixed with DP may decrease the permeability of the 3D structure.

For example, a 3D structure comprising 0.05% GO-2% ELK1 may be more permeable than a 3D structure comprising 0.1% GO-2% ELK1. A 3D structure comprising 0.1% GO-2% ELK1 may be more permeable than a 3D structure comprising 0.15% GO-2% ELK1.

In addition, by culturing cells on the 3D structures, endothelilizing the 3D structures, it is possible to then define the permeability of the 3D biohybrid structure based on these cells (See FIG. 15). This may be very important in a tissue engineered device where the cells, which now play an active part in the fabricated structure, can define the level of permeability and can modulate it. This is what happens in veins and vasculature in vivo and therefore may be important to consider when recreating tissue in a lab situation. If cells are using a polymer tube, rather than one of the 3D structures described herein, the material is not permeable so the cells do not really play a role in the permeability of the tube.

Using different densities of seeded cells (e.g. hUVECs) on the 3D structure can lead to differing permeabilities. For example, increasing the confluency of hUVECs may decrease the permeability of the 3D structure.

The capacity to design and modulate permeability in the 3D structures disclosed herein enables them to mimic different biological tissues and other devices with similar levels of permeabilities.

The 3D matrix is biocompatible. Given the capability to incorporate cells, additional structures and/or exosomes during the assembly process, capillary-like structures having cells, additional structures or exosomes embedded within and on the membrane defining the tube were successfully grown (FIG. 2d). Based on this simple, yet robust, tubular assembly and growth, as well as the capacity to incorporate cells, additional structures or exosomes and immediately withstand flow of solutions, this enables the use of rapid-prototyping techniques to control co-assembly spatio-temporally and fabricate more complex capillary-based micro-fluidic devices. For example this could be achieved by applying the methods as described herein to a 3D printing device and using a 3D printer to fabricate the tubes as described herein.

The capacity of the material to self-assemble in cell friendly environments opens opportunities to biofabricate complex and functional capillary-based fluidic devices that may offer a higher level of biological relevance compared with traditional devices. This potential was assessed by suspending human umbilical vascular endothelial cells (hUVECs) within the DP solution prior to co-assembly and growing the tubes in a similar manner. Fluorescence microscopy revealed the cells were present both within the assembled GO-protein matrix as well as inside the lumen of the corresponding tubes right after co-assembly (FIG. 2d). Without wishing to be bound by theory, it is hypothesised that that as the diffusion-reaction mechanism of formation takes place, cells, additional structures or exosomes located at the interface between both solutions are either trapped within or adhered to the assembling membrane. At this point, cells, additional structures or exosomes suspended in the newly enclosed DP solution further bind to the inner membrane of the tube. Cells were observed to spread and grow for at least 7 days both within the membrane and on the lumen of the tubular structures, indicating that the material is able to support cell survival and growth. Exosomes and other additional structures as described herein may also be localised, embedded and delivered by the 3D structures.

To confirm this finding, cell adhesion and proliferation assays were conducted on both the inside and outside surfaces of the membranes of preformed ELK1-GO tubes. Remarkably, cells were found to adhere and proliferate at similar levels as those growing on tissue culture plastic surface (FIG. 3a, b), forming a confluent layer on both sides of the membrane (FIG. 3c). To further assess the cell behaviour on the tubular structures, VE-cadherin (CD144) was labelled to observe the organization of the intercellular junctions, which may be critical for the formation of an intact endothelial monolayer. Confocal images revealed that hUVECs were able to form an integral monolayer on both sides of the ELK1-GO membrane (FIG. 3d). The formation of such intercellular junctions is of particular implication for the vasculogenesis on the ELK1-GO membrane.

This notable cell growth and spread on the co-assembled membranes suggests that the hybrid material is cell friendly in vitro. While DP materials such as ELPs have been shown to support cell growth GO is known to be cytotoxic to endothelial cells in vitro at concentrations higher than about 100 ng/mL as a result of plasma membrane damage and oxidative stress. It may be important to keep in mind that GO cytotoxicity depends on the inherent properties of the specific GO used. Based on our results, negligible cytotoxicity was observed on the DP-GO membranes even when using GO concentrations of up to 4 mg/mL.

To further confirm the biocompatibility of the material, DP-GO tubes were implanted directly on an ex vivo pre-clinical chick chorioallantoic membrane (CAM) model for 7 days and assess their cytotoxicity and angiogenesis. Using a Chalkley count analysis, similar angiogenesis was observed on both tube-containing samples and control samples (blank model) (FIG. 3g). In addition, immunohistochemistry was applied to identify endothelial cells via labelling of alpha smooth muscle actin ($\alpha$-SMA) and Goldner's trichrome staining to distinguish cells from surrounding connective tissue. The results reveal the presence of capillary-like structures, which in many cases appeared to develop and spread in the vicinity of the DP-GO membrane (FIG. 3e, f). These results are in alignment with previous studies demonstrating the angiogenic potential of GO. However, our approach enables this angiogenic potential while enabling the use of much higher concentrations of GO.

As described herein, prior to admixing the DP and GO solutions, the method may further comprise suspending cells, additional structures and/or exosomes in the DP solution. The DP solution may further comprise cells in suspension. The DP solution may further comprise exosomes in suspension. The DP solution may further comprise additional structures, as described herein, in suspension. The cells may be human umbilical vascular endothelial cells (hUVECs). A person skilled in the art would be familiar with methods of culturing such cells and collecting exosomes.

The cells, exosomes and/or additional structures may also be added to the tubes once they are formed. The methods as described herein may further comprise a step of seeding cells, additional structures and/or exosomes onto the 3D structure during or after admixing the DP and GO solutions. Methods of seeding cells are known to the skilled person.

Where the tubes include cells or exosomes, the cells or exosomes may be found embedded within the assembled graphene oxide-protein matrix, present in the lumen of the 3D structure; and or adhered to the inner surface or outer surface of the membrane defining the lumen of the graphene oxide-protein matrix.

The cells cultured on the tubes may form characteristic tight-junctions such as are formed in blood vessels.

The tubes, as described herein, are capillary like and may find application in the fabrication of complex capillary-based microfluidic devices, methods of preparing artificial blood vessels and regenerative medicine.

As described herein, the present invention provides a graphene oxide-protein matrix comprising a disordered protein (DP) and graphene oxide (GO), wherein the DP has an opposite charge to the GO, further wherein the graphene oxide-protein matrix is in the form of a 3D structure having a lumen defined by a membrane having an inner and outer surface.

As described herein, the present invention provides a method of preparing a graphene oxide-protein matrix using a device comprising;

(a) a reservoir of an aqueous solution of DP (b) a nozzle in fluid connection/communication with the reservoir of DP solution wherein the DP solution is delivered via the nozzle to a reservoir of GO, wherein the nozzle may optionally be controlled by a computer, and further wherein the graphene oxide-protein matrix may be in the form of a 3D structure having a lumen defined by a membrane having an inner and outer surface.

The device as described herein may be a 3D printer that may be used to print the DP solution within a GO solution. The 3D printer may be an extrusion-based 3D printer, an inkjet printer or a laser-assisted printer.

Different types of 3D printer may be used to generate different structures. For example, inkjet printing, can be used to reproducibly generate well-defined sacs or microcapsules (See FIG. 9).

"Traditional" 3D printing methods typically require the printer to be able to move in all 3 dimensions in order to build up a 3D model based on multiple 2D layers that are built up using a process called fused deposition modelling.

Hydrodynamic forces generated during the admixing process, which may be a printing process, as the two liquids (DP and GO) hit each other, can be used to generate different kinds of hollow geometries. By changing the pressure used during admixing, or printing, when the DP and GO, well-defined spherical sacs, sacs with a tube attached, and elongated sacs with an opening on one end can be created (see FIG. 10). All these complex, yet reproducible, geometries are made by the process of injecting the material and its subsequent self-assembly. This is very different to what can be done with other bioinks that require the printer to move along all 3 axes to try to recreate the required geometry.

In the present invention, the resolution of the final structure is not determined by the printer (as it is in traditional 3D printing methods), but rather by the bioink itself. For example, in FIG. 11a, the thickness of the wall of each of the three geometries shown is defined by the bioink to be around 10 um. This is a much smaller feature than any bioink to date (which are around 20-50 um).

Further optimization of the admixing parameters, or printing parameters, are also possible. For example, the tube diameter can be modulated by modifying admixing, or printing, speed. Modifying the amount of GO used makes it possible to change the thickness of the membrane produced. (FIG. 11a).

The reservoirs of aqueous solutions of DP or GO may be a cartridge, a container, a receptacle, a holder, a repository, a tank, a sump or another container designed to hold fluid.

The nozzle may be a cylindrical or round spout at the end of a pipe, hose, or tube used to control a jet of gas or liquid. It may be a needle, a pipette tip, or another device capable of extruding fluid in a controlled manner.

The methods of 3D printing as described herein may comprise performing the methods as described herein using an apparatus for 3D printing. The methods as described herein, prior to admixing the DP and GO solutions, may further comprise the step of loading the solutions into a 3D printing apparatus.

A bioink, as defined herein, is a fluid, gel or hydrogel which may be used during additive manufacturing processes such as 3D bioprinting. The skilled person would readily understand that the aqueous DP solutions disclosed herein are suitable for use as bioinks. All features of aspects of the invention relating to bioinks apply mutatis mutandis as for the aspects relating to aqueous DP solutions, and vice versa.

Bioinks are compatible with cells and may comprise cells. Bioinks may be aqueous and may further comprise nutrients and matrix components (such as extracellular matrix components). Another major goal of bioinks is to recreate the extracellular matrix (ECM). This is one of the reasons why there is increasing interest in printing ECM. However, ECM inks are unpredictable in terms of their composition and also during their preparation (i.e. extraction from tissues) as many proteins can be modified. Our approach provides an alternative that is more predictable. Being able to assemble the material (at the time of printing) using multiple proteins found in the ECM (like elastin, collagen, fibronectin) offers a way to design and tune the composition of our final ECM-like printed material/structure. (see FIG. 8)

A bioink does not necessarily comprise cells and may comprise components to support cell growth and proliferation, or provide a scaffold for cells to grow. Described herein is a bioink comprised of an aqueous solution of DPs, which may further comprise a suspension of cells.

A bioink, as described herein, may comprise an aqueous solution of DP, wherein the aqueous solution of DP has a concentration of from about 0.2% wt/vol to about 7.5% wt/vol or preferably from about 0.5% wt/vol to about 3.0% wt/vol, wherein the aqueous solvent is water or a water-based medium such as cell culture medium or a buffer solution such as phosphate-buffered saline (PBS). The bioink may further comprise a suspension of cells, such as hUVECs in the aqueous solution of DP. The bioink may comprise a suspension of multiple cell types to give robustness to the material. The bioink may be loaded into a cartridge which is loaded into a 3D printer, or the bioink may be loaded directly into a 3D printer.

3D bioprinting requires a medium on which to deposit or print the bioink. Such mediums are often referred to in the art as "bio-paper". Such bio-papers may comprise a scaffold or hydrogel the bioinks may be printed on to. As described herein, the bio-paper medium for printing the bioink on to comprises an aqueous solution of GO, wherein the aqueous solution of GO has a concentration of from about 0.01% wt/vol to about 0.5% wt/vol or preferably from about 0.01% wt/vol to about 0.2% wt/vol wherein the solvent is water or another water-based medium such as cell culture medium or a buffer solution such as phosphate-buffered saline (PBS). The bio-paper medium comprising the aqueous solution of GO may be loaded into a cartridge which is loaded into a 3D printer, or the bio-paper may be loaded directly into a 3D printer. Alternatively, the bio-paper may remain separate from the 3D printer and simply be present as a medium to inject the bioink into.

Described herein is a kit comprising
a) a bioink comprised of an aqueous solution of DPs, which may further comprise a suspension of cells
b) a bio-paper comprised of an aqueous solution of GO wherein the bio-paper is a solution or gel into which the bioink can be admixed A person skilled in the art would understand how the methods described herein of preparing a graphene oxide-protein matrix, the method comprising; admixing an aqueous solution of a disordered protein (DP) with an aqueous solution of graphene oxide (GO), wherein the graphene oxide-protein matrix is in the form of a 3D structure having a lumen defined by a membrane having an inner and outer surface could be applied to a method of 3D printing. The skilled person would likewise be able to adapt the methods described herein to use a 3D printer.

Using a 3D printer to carry out the methods as described herein allows the 3D structures as described herein to be mass produced quickly and effectively and increases the range of tubular structures, networks and tissues that can be prepared. Complex capillary like microfluidic devices may be prepared, as well as complex tissues and organs with complex blood vessel or tubule networks to allow the tissues, cells or organs to proliferate and grow and oxygen and nutrients to diffuse throughout the structure.

Using a 3D printer may also allow the preparation of artificial blood vessels that are robust, biocompatible and dynamic.

This new bioink, as described herein, has the capacity to produce tubes or tubular networks (including bifurcations like in Figure h ii and iii) by itself via self-assembly. Current methods of 3D printing can be used to print tubular shapes, but by layering or depositing the materials in the shape of a tube, not based on the properties of the ink itself. The liquid-on-liquid printing method of the invention enables the fabrication of small 3D structures (such as tube geometries) in a single injection. This enables the printing of tubes on a much smaller scale than currently possible, for example small tubes (FIG. 2C) with diameters of less than about 50 μm and membranes down to about 10 μm in membrane thickness. Classical 3D printing can't do this since classical 3D printing requires the printer to move along all 3 axes in order to print such structures. Now, the inventors have also demonstrated that more complex and larger structures can be printed by printing in this traditional 3D printing manner, creating multiple layers of tubes by combination of self-assembly and also moving the printer along all 3 axes (see FIG. 9)

The bioinks further enables cells to be included, embedded within the membrane, and enables the cells to grow within and on the microtubes. The bioink is highly robust in terms of printing structures while also keeping many cell types alive, even more delicate cell types which are harder to print.

These opportunities in terms of its biocompatibility and ability to enable cell growth is partly due to the fact that cross-linking agents are not required. The "setting" or solidification of the ink takes place due to the DP-GO self-assembly and this setting process is highly biocompatible since no harsh crosslinkers or conditions are needed to provide or maintain the mechanical properties.

The bioinks as described herein have the advantageous properties of; ability to form functional tubes, ability to form functional tubes as small as about 10 μm in diameter and membranes of at least about 5 μm in thickness, ability to form "complex geometries" such as tubular networks (with bifurcations), ability to "set" without any cross-linking agent or process, ability to "set" by self-assembly. This enables printing solutions with very low viscosity, which enhances cell viability during the printing process, which is a key challenge in bioprinting.

All of these properties are demonstrated while also incorporating cells. The tubes and bioinks as described therein have the following additional advantageous properties; ability to stimulate endothelial cells to proliferate and function as in native tissue; enables printing of microfluidic devices.

Use of the methods as described herein, and methods of 3D printing these structures and the 3D structures, as described herein, may find application in new ways to grow complex and functional devices such as tissue engineering scaffolds, microfluidic systems, artificial blood vessels, labs-on-a-chip or organs-on-a-chip devices by self-assembly and may find application in fields such as regenerative medicine, synthesis and analysis.

Also described herein is a graphene oxide-protein matrix comprising a disordered protein (DP) and graphene oxide (GO), wherein the graphene oxide-protein matrix is in the form of a 3D structure having a lumen defined by a membrane having an inner and outer surface.

Also described herein is a kit for preparing a graphene oxide-protein matrix, the kit comprising;
a) an aqueous solution of a disordered protein (DP)
b) an aqueous solution of graphene oxide (GO)
wherein when the aqueous solution of DP and the aqueous solution of GO are admixed, a graphene oxide-protein matrix in the form of a 3D structure is formed spontaneously. The 3D structure may have a lumen defined by a membrane having an inner and outer surface.

The kit may also comprise instructions on how to use the components.

Microfluidic devices can be used in systems to achieve multiplexing, automation, and high-throughput screening, DNA chips, lab-on-a-chip technology, micro-propulsion, and micro-thermal technologies. Microfluids is concerned with the behaviour of fluids at the microscale and rely on passive fluid control using capillary action. Microfluidic technologies can be used in molecular biology procedures for enzymatic analysis, DNA analysis (e.g., polymerase chain reaction and high-throughput sequencing), and proteomics. Microfluidic biochips aim to integrate assay operations such as detection, sample pre-treatment and sample preparation on one chip, for example DNA or protein microarrays.

As described herein the simple, yet robust, tubular assembly and growth of the graphene oxide-protein matrix, as well as the capacity to incorporate cells and immediately withstand flow of solutions, presents the possibility to use rapid-prototyping techniques to control co-assembly spatio-temporally and fabricate more complex capillary-based microfluidic devices. Complex capillary like microfluidic devices may be prepared, as well as complex tissues and organs with complex blood vessel or tubule networks to allow the tissues, cells or organs to proliferate and grow and oxygen and nutrients to diffuse throughout the structure.

Lab-on-a-chip devices may use microfluidics and is concerned with laboratory experiments carried out on a very small scale. It can integrate several laboratory functions on a chip of size ranging from a few millimetres to a few square centimetres. This helps achieve high-throughput screening and automation and can be used in diagnostic, analysis, synthesis and sequencing. However, physical and chemical properties such as surface roughness, capillary forces, and chemical interactions between materials are more significant at the microscale level. This can often result in complications during lab-on-a-chip experiments which would not be found with traditional, full scale lab equipment. Furthermore, the micro-manufacturing process required to make them is complex and labour intensive, requiring expensive equipment and experienced personnel. There is a need in the art for a cheap, simple way to prepare robust and effective lab-on-a-chip devices.

An emerging application area for biochips is clinical pathology and biomedical engineering. For example, organ-on-a-chip devices are artificial organs on the microscale. They are 3D microfluidic cell culture chips that have the ability to simulate the activities, mechanics and physiological response of whole organs and organ systems. They are used in the study of human physiology in an organ-specific context, and represent a novel model of in vitro multicellular human organisms. An area of interest is regenerative medicine, drug and toxin testing and replacing animal testing. Nevertheless, even the best 3D culture models fail to mimic an organ's cellular properties including tissue-to-tissue interfaces (e.g., epithelium and vascular endothelium), spatiotemporal gradients of chemicals, and the mechanically active microenvironments. The application of microfluidics in organs-on-chips enables the efficient transport and distribution of nutrients and other soluble cues throughout the viable 3D tissue constructs. There is a need in the art for a cheap, simple way to prepare robust and effective organ-on-a-chip devices which better mimic an organ's properties.

Bioelectronics is a discipline resulting from the convergence of biology and electronics. It seeks to exploit biology in conjunction with electronics, for example, biological fuel cells, bionics and biomaterials for information processing, information storage, electronic components and actuators. A key aspect is the interface between biological materials and micro- and nano-electronics. Organic bioelectronics is the application of organic electronic material to the field of bioelectronics. Organic material, such as those comprising carbon, show great promise when it comes to interfacing with biological systems. Current applications focus around neuroscience and infection. Bio computers use systems of biological molecules, such as DNA and proteins, to perform computational functions involving storing, retrieving, and processing data. This incorporates the field of nano-biotechnology.

Use of the methods as described herein, and methods of 3D printing these structures and the 3D structures, as described herein, may find application in new ways to grow complex and functional devices such as tissue engineering scaffolds, microfluidic systems, bioelectronics, artificial blood vessels, labs-on-a-chip or organs-on-a-chip devices by self-assembly and may find application in fields such as regenerative medicine, synthesis and analysis.

All preferred features of the second and subsequent aspects of the invention are as for the first aspect mutatis mutandis.

LIST OF FIGURES

The present invention will now be described by way of example only with reference to the accompanying figures wherein:

FIG. 1. Molecular building blocks and rationale for co-assembly.

a. Table summarizes the key information of the three elastin-like polypeptides (ELPs) used in the study comprising similar molecular weight but different levels of hydrophobicity (VPGIG) and positive charge (VPGKG). b. Illustrations of the molecular structure of a GO sheet and the supramolecular organisation of ELK1 at its Tt (30° C.) indicating both the charged (red and green) and hydrophobic (brown) segments. c. Schematic of the proposed mechanism of formation illustrating the molecular and supramolecular conformation of the GO and ELK1 before and after co-assembly at the ELK1's transition temperature (Tt) as well as their interaction for membrane formation.

Figure 2:
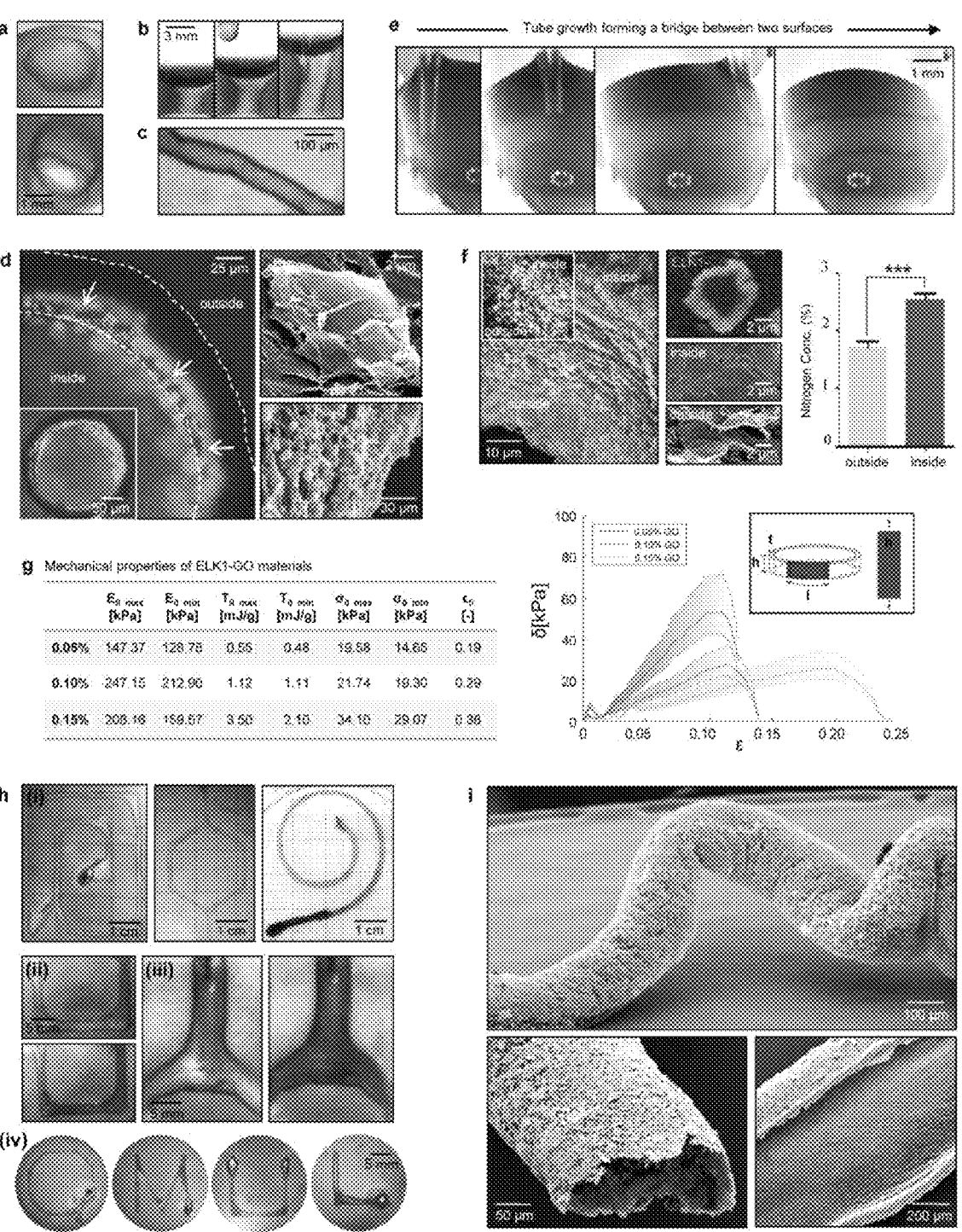

FIG. 2. Co-assembly, structure, properties, and biofabrication of the ELK1-GO system.

Time-lapse images illustrate the dynamic properties of the ELK1-GO membrane first a. Forming a closed sac when a drop of ELK1 solution is immersed in a larger GO solution, opening upon touching an interface within the first seconds of formation, and b. Growing into longer tubes on demand by displacing an interface. The robustness of the system enables c. Formation of capillaries down to about 50 μm in internal diameter with 10 μm thick walls. d. Co-assembly can take place in salt solutions, opening the possibility to embed cells (green identified by white arrows) within the membrane (outlined by dashed lines) as the tubes are formed. The images are taken after 24 h of culture and correspond to a live (green)/dead (red) assay. Scanning electron micrographs of cells embedded within layers of GO (top) and a cross-section of the ELK1-GO membrane comprising cells within different layers (bottom). e. Capability of the ELK1-GO system to bridge surfaces simply by touching two interfaces while injecting one solution into the other. f. The membrane exhibits a multi-layered architecture of about 50 μm thick comprising aligned GO sheets throughout (birefringence inset) interacting with ELK1 molecules (fluorescence image). ELK1 was observed to decrease in concentration from the inside to the outside as evidenced by wavelength-dispersive spectroscopy (WDS) (graph). Only ELK1 comprises nitrogen in its molecular structure. g. Nanotensile test results reveal that the strength, the strain at break, and the toughness modulus increased on tubes formed with increasing concentrations of GO but the elastic modulus was highest on tubes made with medium level (0.10%) GO compared to lower (0.05%) and higher (0.15%) amounts based on Weibull statistical distribution. h, i. Images demonstrate the versatility of the co-assembly system by incorporating it with 3D printing to fabricate well-defined fluidic devices consisting of high-aspect ratio tubular structures (i) of different internal diameters and comprising curves, angles of different sizes, and bifurcations (ii, iii, iv) capable of withstanding flow within a few minutes of formation (ii, iii).

Figure 3:
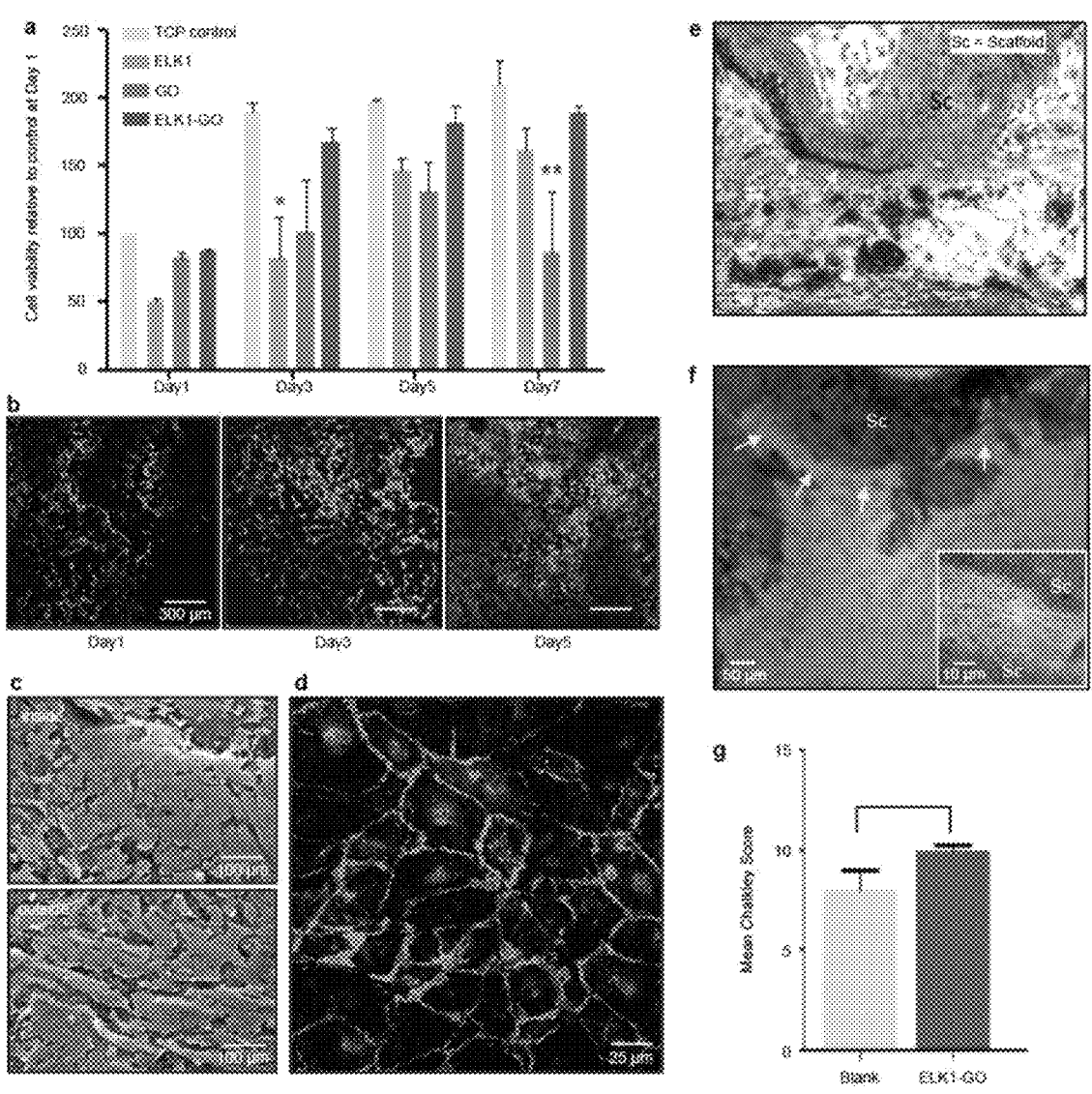

FIG. 3. In vitro biocompatibility and bioactivity of the ELK1-GO membrane.

a. The applicability of the material was assessed by an MTS assay to test cell viability and proliferation of hUVECS on both sides of the ELK1-GO membrane. The results revealed that cell viability and proliferation on ELK1-GO materials are at least similar to those of cells growing on tissue culture plastic (TCP) for 7 days. Error bars represent ±s.d. for n=3. *p<0.05. b. Live (green)/dead (red) assay confirmed the proliferation of hUVECs. c. Scanning electron micrographs demonstrate the formation of an integral endothelial layer on both sides of the ELK1-GO membrane. d. VE-cadherin (00144) was labelled to observe the organization of the intercellular junctions and revealed that cells exhibited strong intercellular junction staining, also suggesting the formation of an integral endothelial layer on the ELK1-GO membrane. e, f. Histological sections of the ELK1-GO tube implants within a chick chorioallantoic membrane (CAM) model for 7 days highlighting Goldner's trichrome (red), alpha smooth muscle actin (α-SMA, pink), and cell nuclei (blue). The results revealed endothelial cells forming capillary-like structures surrounding the ELK1-GO tubes (yellow arrows). g. Chalkley count analysis showing a slightly higher level of angiogenesis on tube-containing samples compared to control (blank model) samples.

Figure 4:
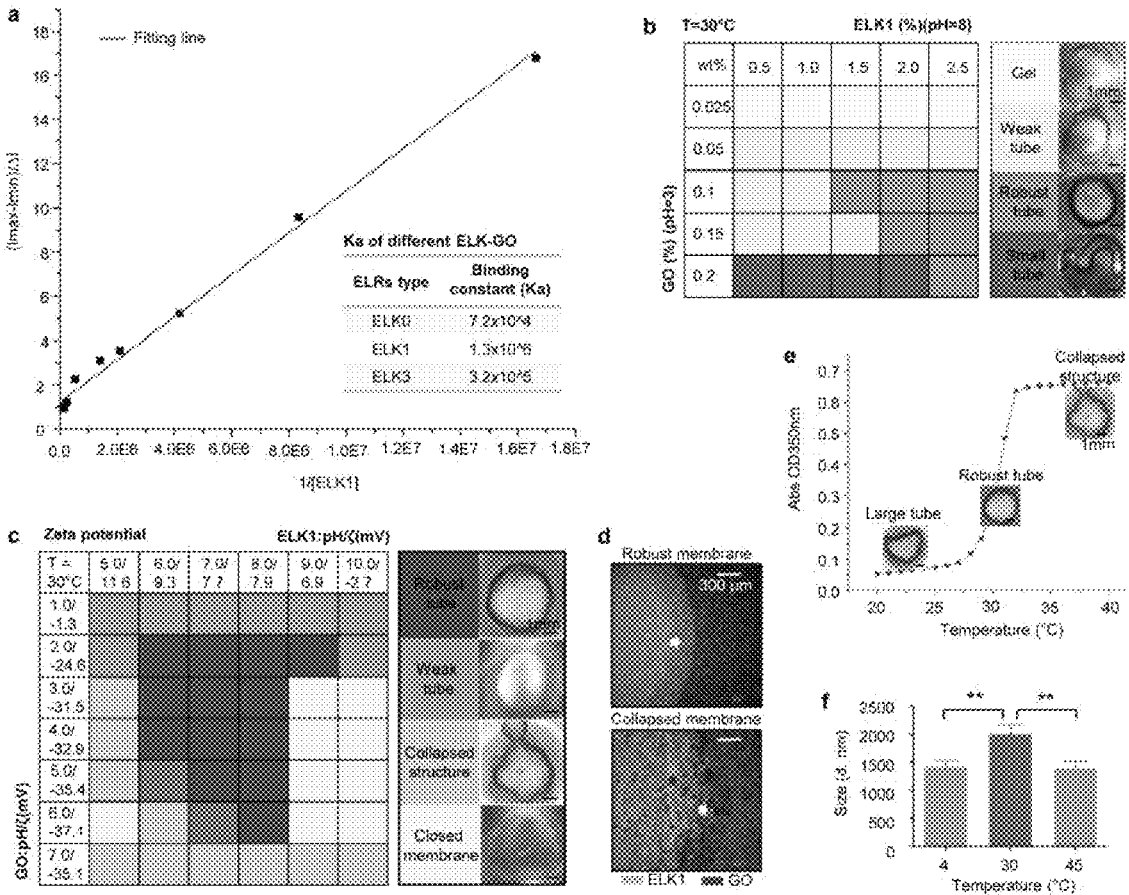

FIG. 4. Molecular interaction and composition of ELP-GO.

a. Binding constants (Ka) for the different ELP-GO combinations calculated by a Benesi-Hildebrand Equation based on fluorescence emission titration of a mixture of GO (2.5×10-3% wt) in MilliQ water solution and increasing concentrations of ELPs revealing higher Ka for ELK1-GO compared to ELK0-GO and ELK3-GO. b. Table illustrating the role of building-block concentration ratio on the formation of ELK1-GO tubes. c. Table illustrating the role of pH and $\zeta$ on the formation of the ELK1-GO tubes and their respective geometry definition. d. Confocal images qualitatively depict the interface between ELK1 (green) and GO (red) during tube formation with different levels of definition. e. Red line of the graph shows the turbidity changes of an ELK1 (2% wt) solution in MilliQ water while inserted images depict the definition of tubes formed at specific temperatures. f. Dynamic light scattering (DLS) revealing the presence of larger ELK1-GO aggregates at 30° C. compared to 4° C. and 45° C. Error bars represent ±s.d. for n=3. *p<0.05.

Figure 5:
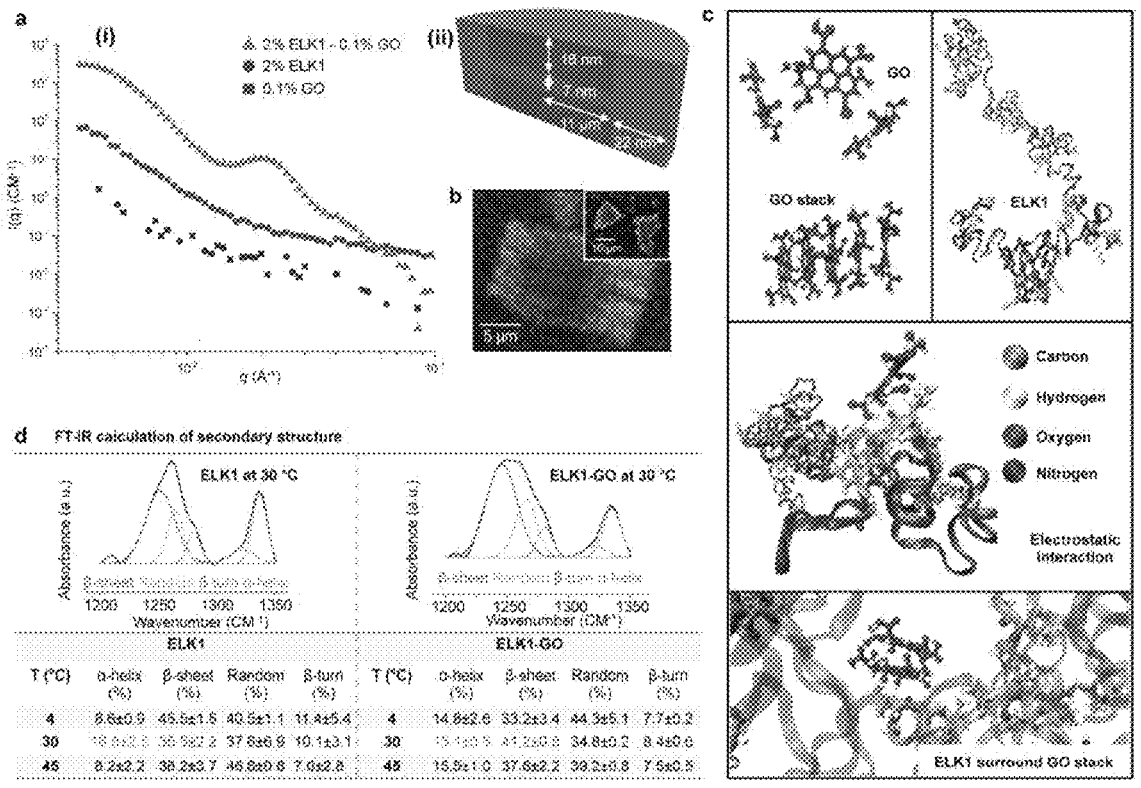
Figure 5:
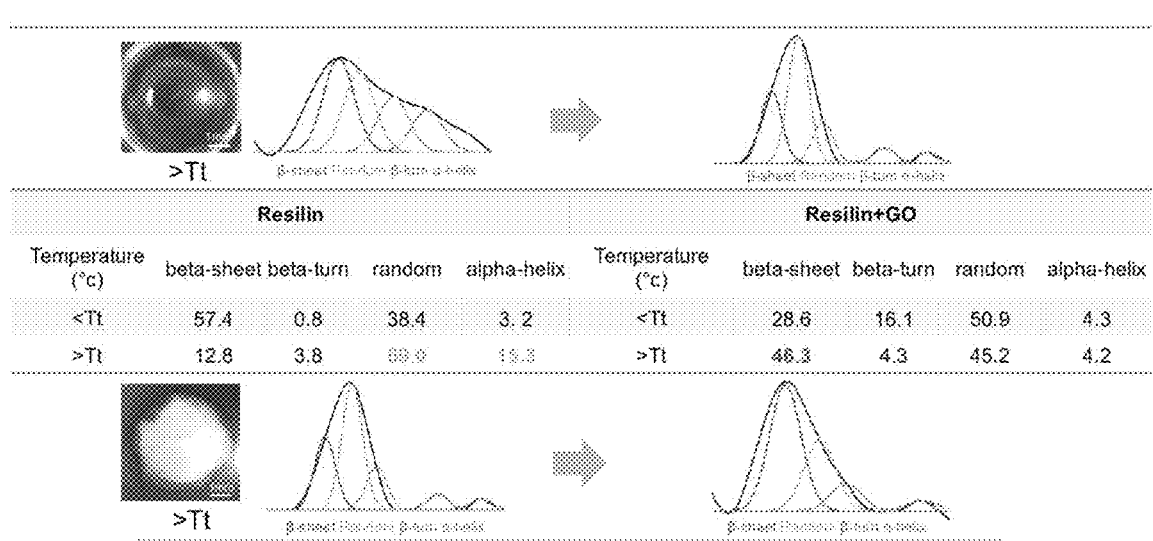

FIG. 5. Supramolecular assembly of the DP-GO system.

a (i). Small-angle neutron scattering (SANS) patterns demonstrating a resulting uniform microstructure formed when co-assembling ELK1-GO. Between the middle-q region (ca 0.007-0.04 Å-1), the EKL1-GO structure (yellow triangle) exhibits a characteristic scattering peak associated with pure ELK1 (green square) and GO (red circle) 30° C., confirming the formation of a new order structure different from the individual components. a (ii). The classical core-shell-bicelle-elliptical model that was fitted to the ELK1-GO microstructure as measured by SANS at 30° C. (green: ELK1, brown: GO). b. Confocal microscopy (green: ELK1, red: GO) corroborating the interaction between the ELK1 and the GO lamellae (inset depicts the top view of the ELK1-GO structure). c. Molecular dynamics (MD) simulation results illustrating how the ELK1 and GO interact in water at 30° C. for 40 ns. d. FT-IR calculation of secondary structure depicting the change and transition of conformation of the ELK1 molecule before and after binding to GO. e. FT-IR calculation of secondary structure depicting the change and transition of conformation of the resilin molecule before and after binding to GO.

Figure 6:
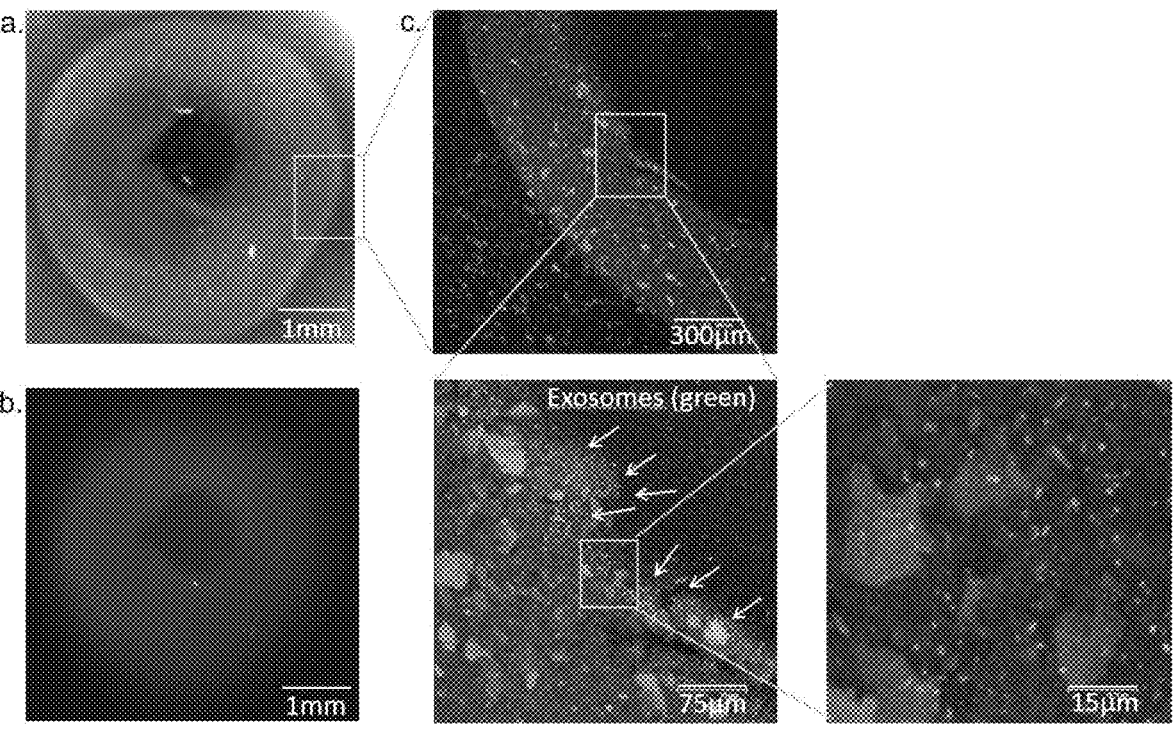

FIG. 6. Co-assembly of ELK1-GO tubes with exosomes a. Optical image of exosomes co-assembled within a ELK1-GO tube. b. Fluorescence images of exosomes co-assembled with a ELK1-GO tube (red: tube, green: exosomes.) c. confocal images of exosomes co-assembled with a ELK1-GO tube (exosomes are green and identified by white arrows) within the membrane as the tube (red) is formed. The exosomes are seen to be localised and embedded in the ELK1-GO tube.

FIG. 7. Carbonisation of the ELK1-GO system a. Scanning Electron Microscopy images show that the ELK1-GO membranes retain their multilayer structure after heating at 1000° C. in a Carbolite STF tubular furnace for 4 hours.

Figure 8:
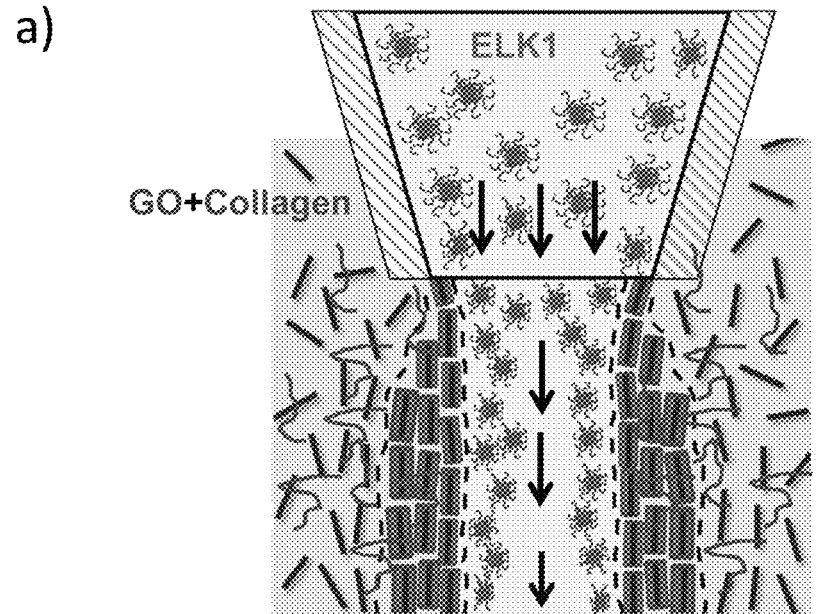
Figure 8:
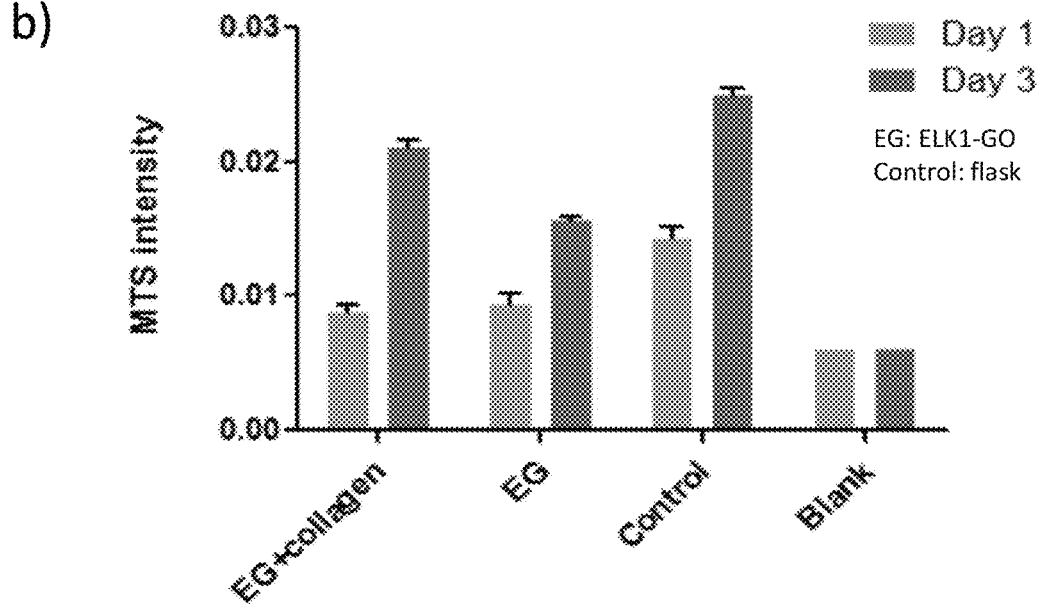
Figure 8:
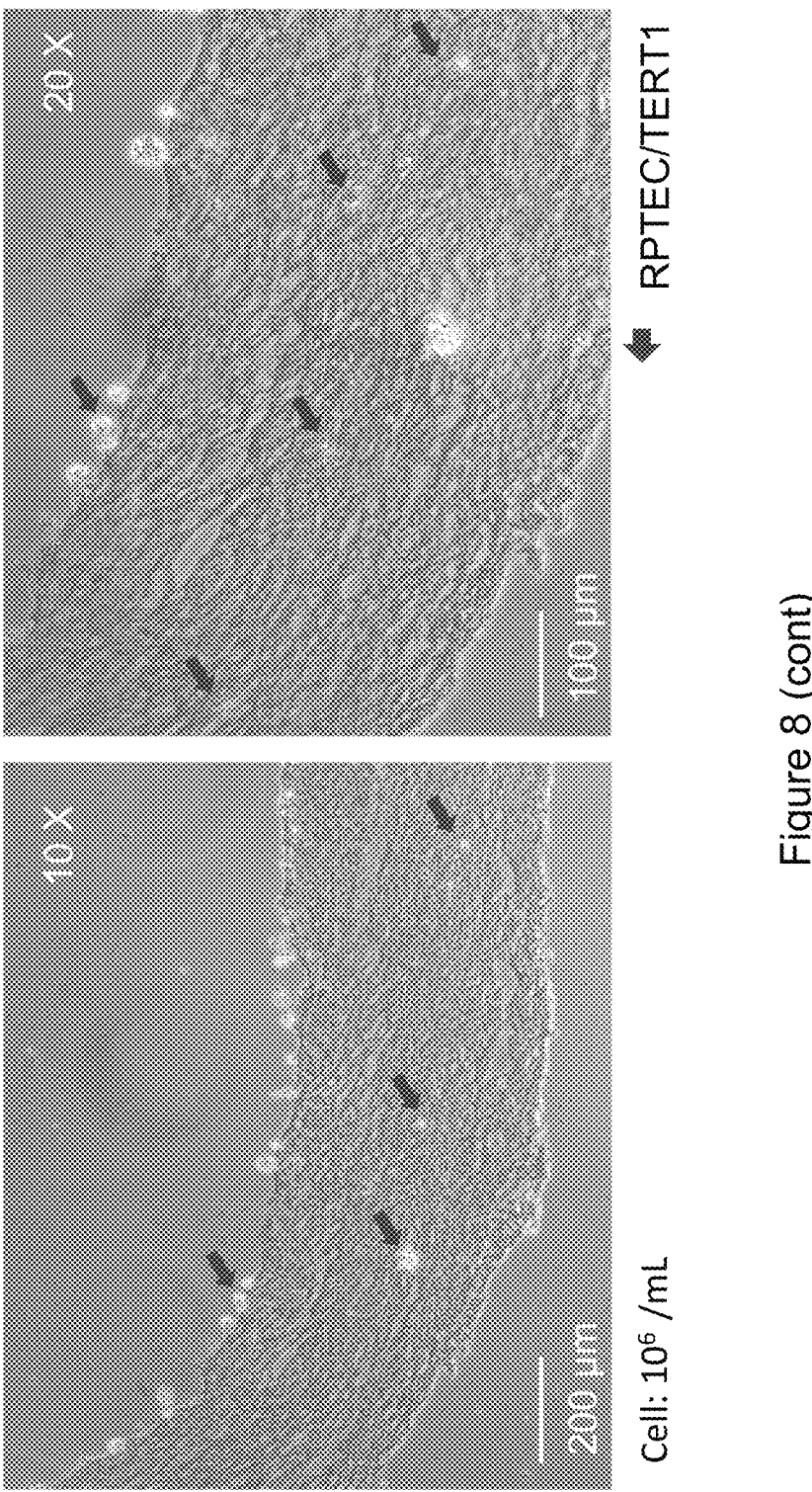

FIG. 8. Co-assembly of ELP-GO with collagen and RPTEC/TERT1 cell line.

a. Illustration shows collagen mixed with GO solution firstly and then together co-assembled with ELP (0.35% GO (+0.005% collagen) water solution, 2% ELK1 cell culture medium, RPTEC/TERT1: $10^6$/mL (20000/well)). b. MTS assay demonstrates a tendency that RPTEC/TERT1 proliferate better in ELP-GO-collagen group than ELP-GO group. c. Optical image of RPTEC/TERT1 cell line co-assembled within an ELP-GO tube. Co-assembled ELK1-GO material with RPTEC/TERT1 cells growing within the material. The cells were printed with the bioink. Histological slides show the cross-section of ELP-GO-RPTEC/TERT tube (red arrow: RPTEC/TERT cell). These results demonstrate that RPTEC/TERT1 cells proliferate both on the inside surface of the formed ELK1-GO tube wall and within the ELK1-GO tube wall.

Figure 9:
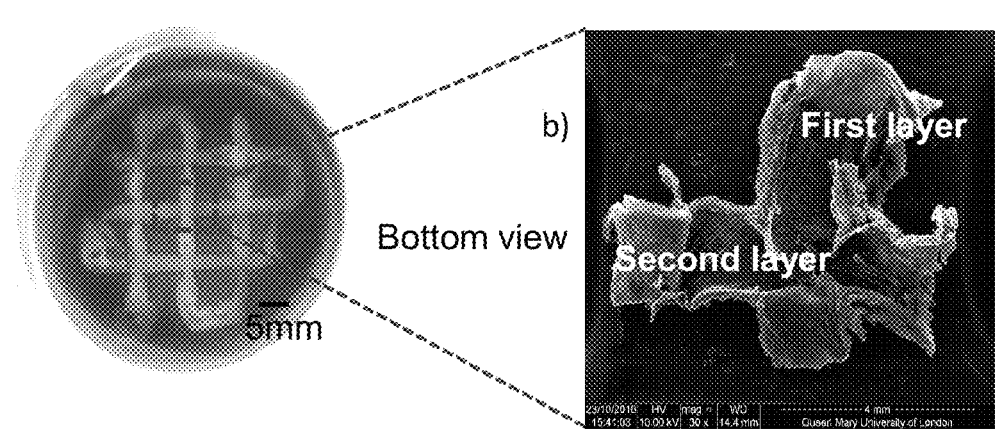
Figure 9:
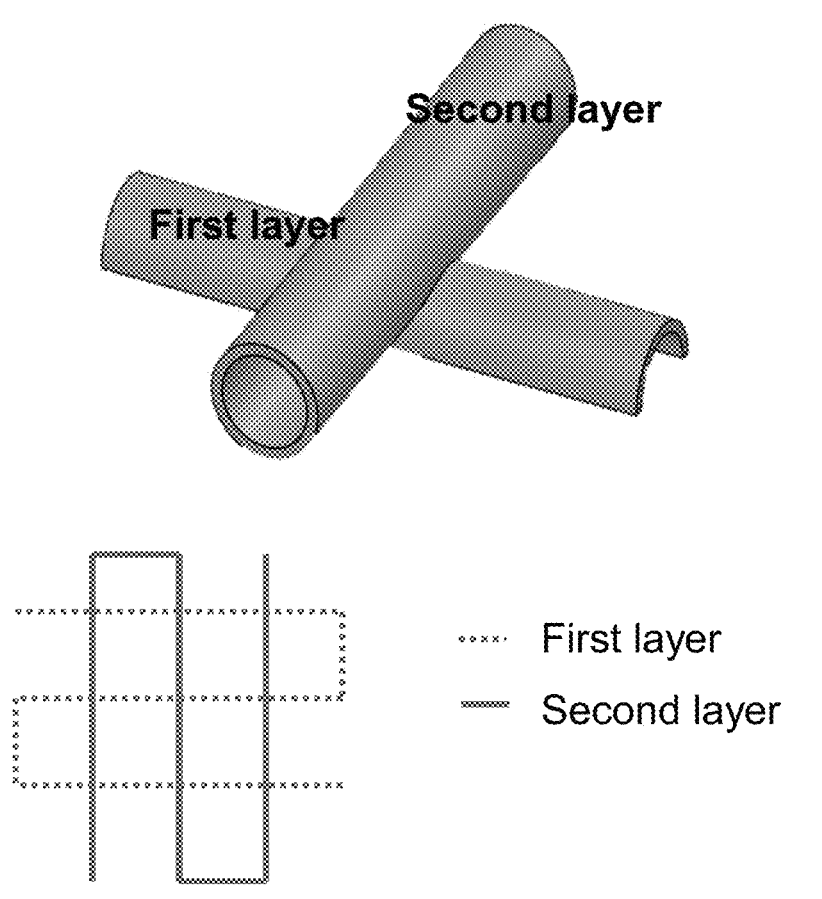

FIG. 9. Extrusion printing two-layer structure of ELP-GO.

a. (Top) Optical image and (Bottom) illustration of two layer ELP-GO tubular structure. b. SEM image of two-layer ELP-GO structure. Here the inventors demonstrate ELK1-GO materials can be used to print multilayer tubular structure. These image and SEM results demonstrate that the inventors are able to fabricate two layers of ELK1-GO tubular structure, which indicates the potential to fabricate bulk 3D tubular structure. Also, the inventors are able to fabricate full channels and half channels.

Figure 10:
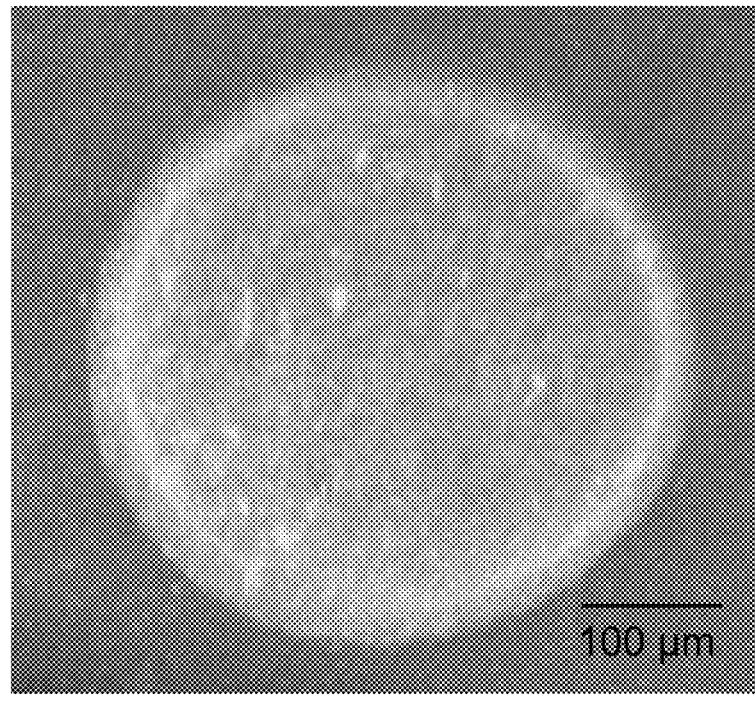
Figure 10:
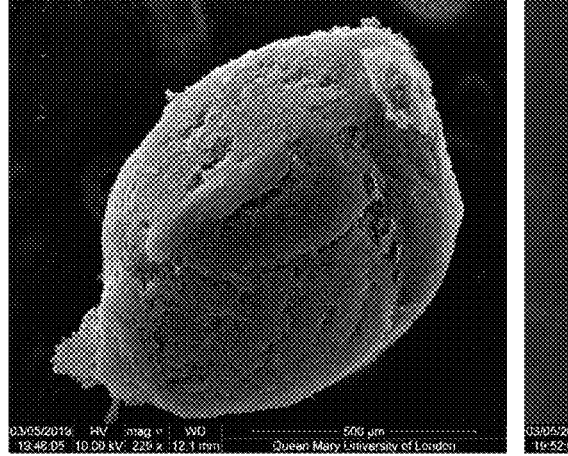
Figure 10:
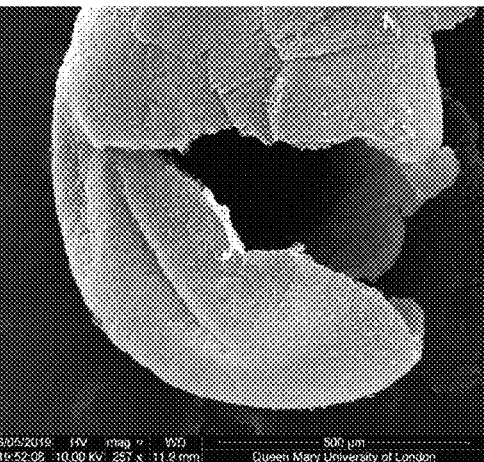
Figure 10:
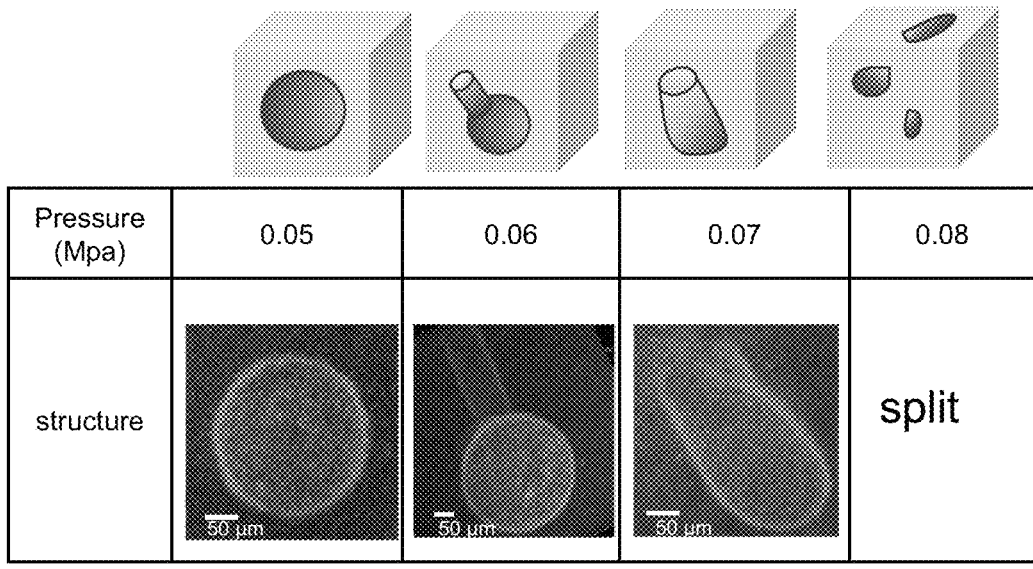

FIG. 10. Inkjet printing ELP-GO sac structure.

a. Inkjet printing parameters (Height=21 mm; Pressure=0.05 Mpa; Inject points=5; Open valve time=100 μs (Table), confocal image, and SEM show the sac structure with only 10 μm thickness wall. b. Adjust pressures of inkjet parameters to fabricate different sac structures. (Inkjet parameters: Height=21 mm; Inject points=5; Open valve time=100 μs; Close valve time=1000 μs) The illustrators show different sac structure. The inventors are able to fabricate different shapes of ELK1-GO sac structures by inkjet printing.

Figure 11:
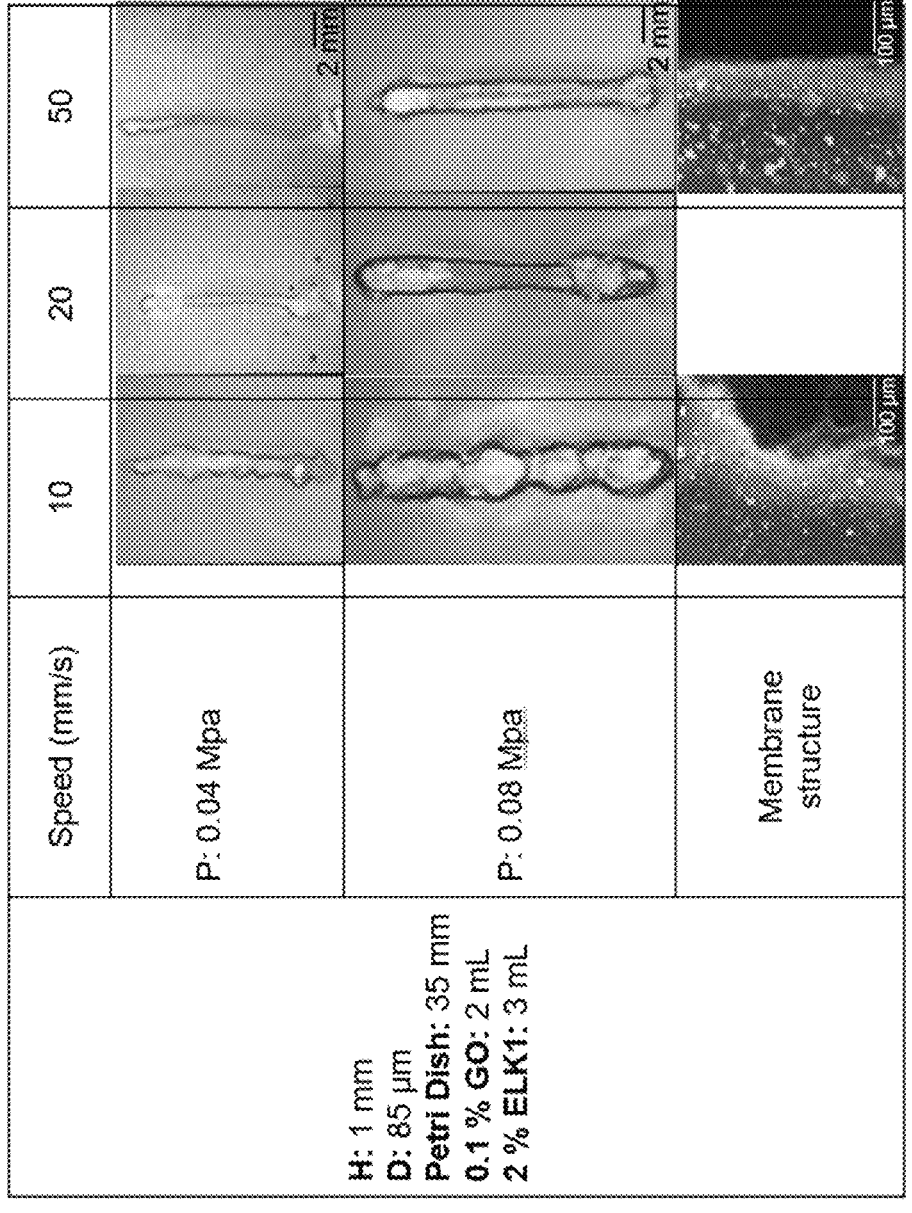
Figure 11:
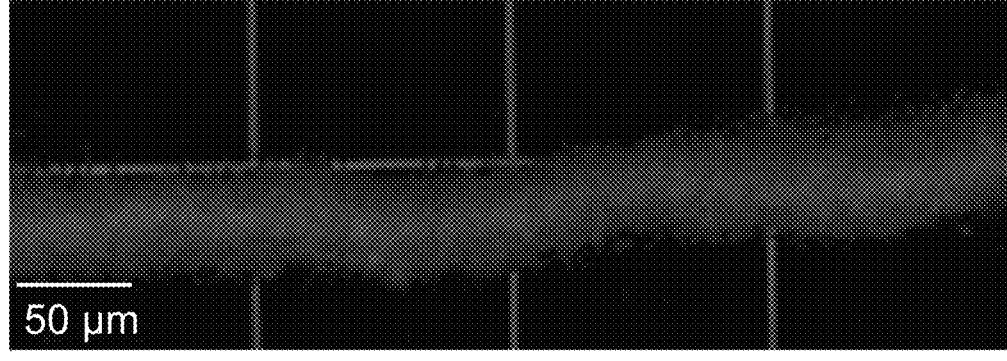
Figure 11:
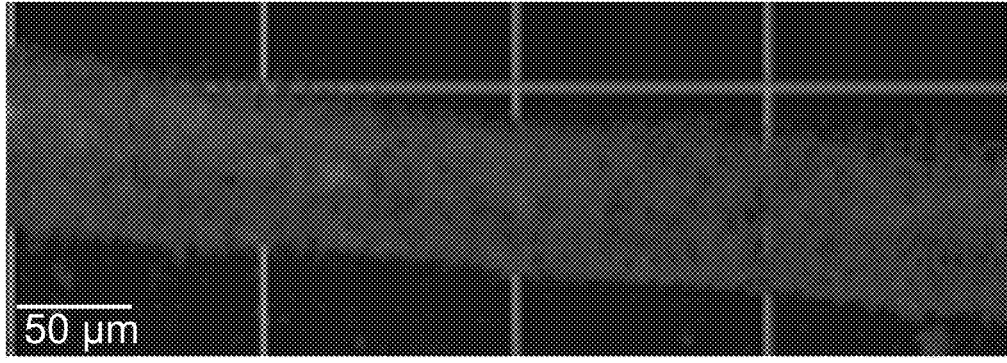
Figure 11:
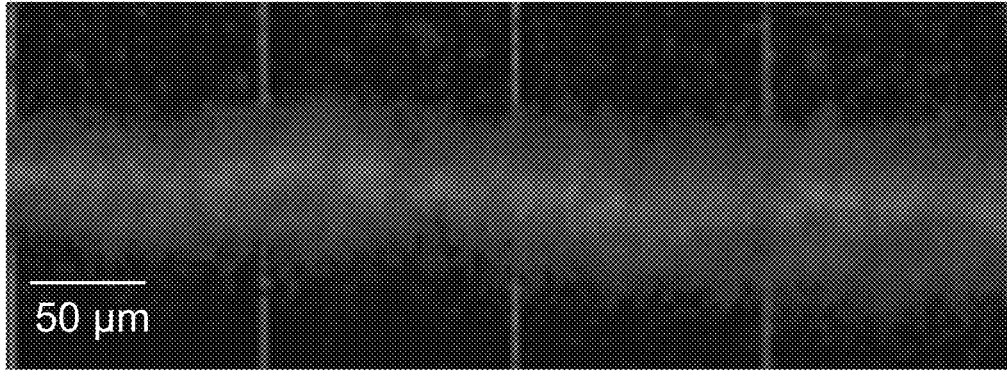
Figure 12:
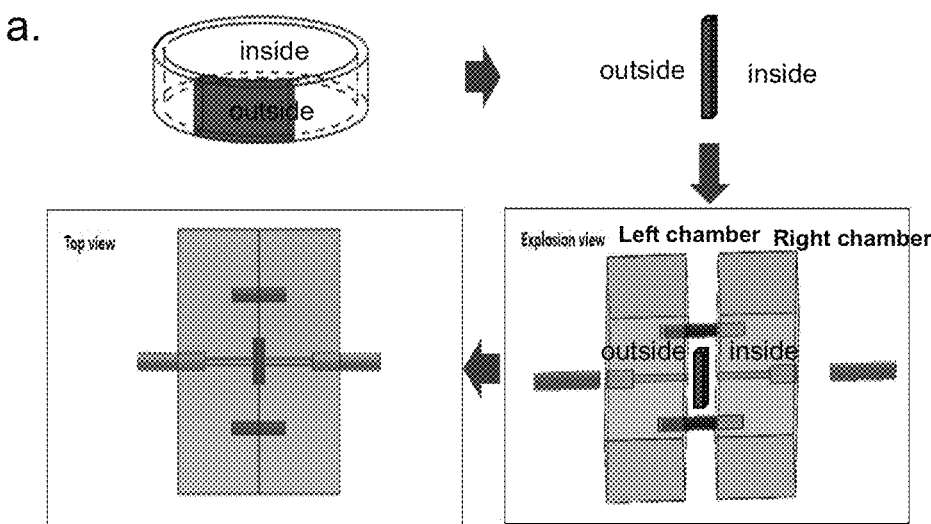
Figure 12:
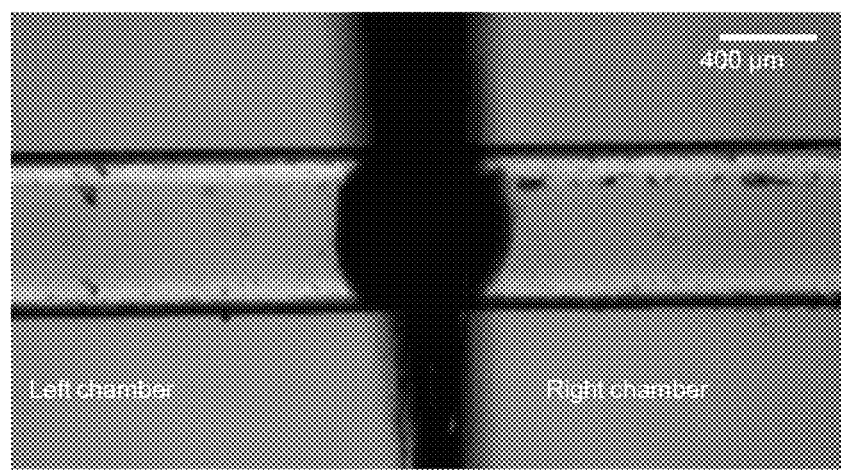
Figure 12:
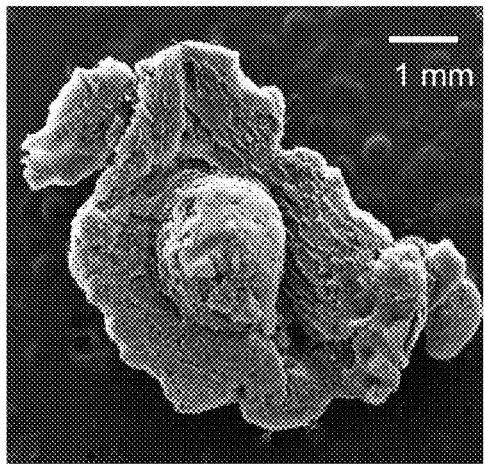

FIG. 11. Standardizing 3D extrusion printing parameters to control the geometry of tubes.

a. Fabricate different inner diameter sizes of tubular structures and change the morphologies of ELP-GO wall membranes by standardizing 3D extrusion printing parameters. (Extrusion parameters of 0.10% GO-2% ELK1) b. Fabricate different thicknesses of the ELP-GO tubular wall membranes by changing the concentration of GO. Confocal images of different % GO-2% ELK1 membrane's cross sections FIG. 12. The device of measuring the permeability of ELP-GO.

a. Illustrator show the device of measuring permeability of ELP-GO. b. Optical image of ELP-GO membrane within measuring device channel. c. SEM image of ELP-GO membrane in measuring device channel.

FIG. 13. Tuneable porosity Of ELP-GO membrane with different concentrations of GO.

a. SEM images show that the porosity of ELP-GO membrane is tuneable with different concentrations of GO. b. calculation of porosity percentage of ELP-GO. c. Table shows the average pore size of ELP-GO membrane.

FIG. 14. Tuneable permeability of ELP-GO membrane with different concentrations of GO.

a. Time slides of confocal images (top) and FEM models (bottom) show fluorescent tracker pass through ELP-GO membrane from right chamber to left chamber. b. Tuneable permeability of FITC-Dextran 20 kDa and fluorescein sodium salt with fitting curves. Table shows different permeability constants of ELP-GO by changing the concentration of GO.

FIG. 15. Tuneable permeability of ELP-GO membrane with different seeding hUVECs density.

a. illustrator shows how the inventors seed hUVECs on ELP-GO membrane and measure the permeability. Confocal images show different confluences of hUVECs are corresponding to different seeding density. b. Tuneable permeability constant with fitting curve.

Figure 16:
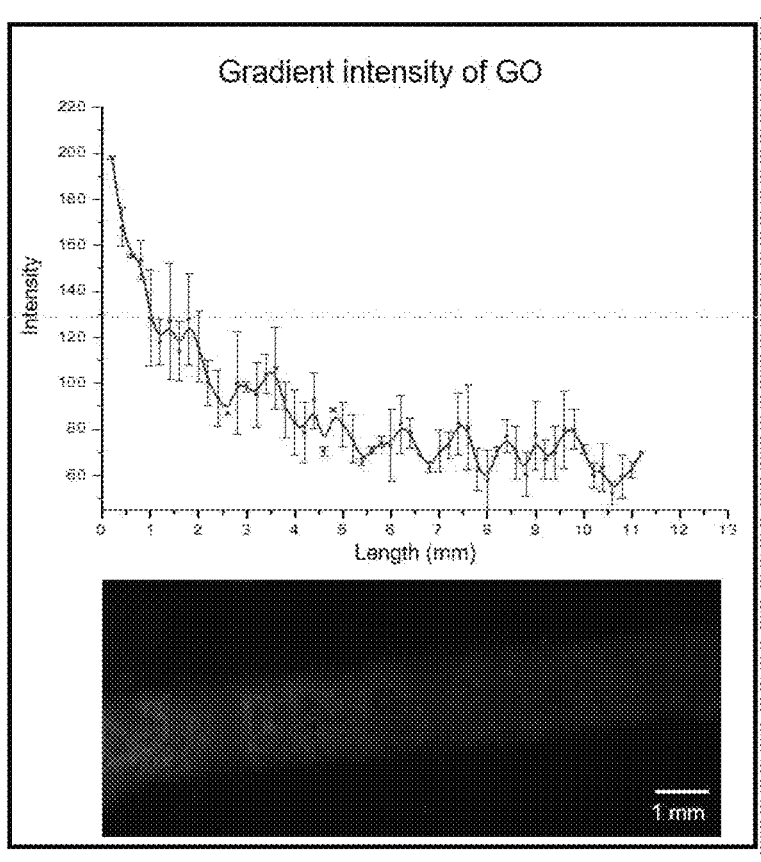
Figure 16:
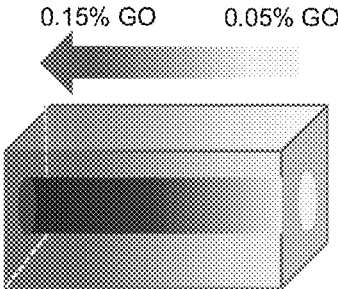
Figure 16:
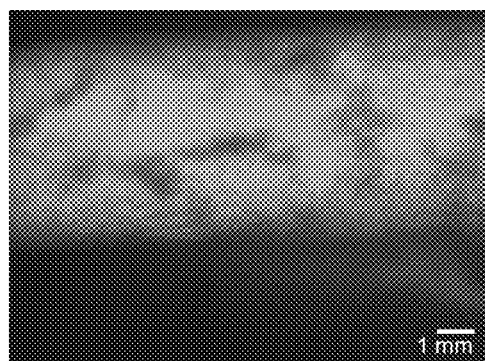

FIG. 16. Tube with gradient permeability.

Illustrator shows the inventors make a gradient of increasing GO % solution from 0.05 to 0.15%, and release 2% ELP from 0.05% to 0.15%. GO is stained with red Rhodamine B, red fluorescent intensity measurement (graph) demonstrates gradient GO components within the tube and gradient permeability (green) of 40 kDa FITC-dextran.

Figure 17:
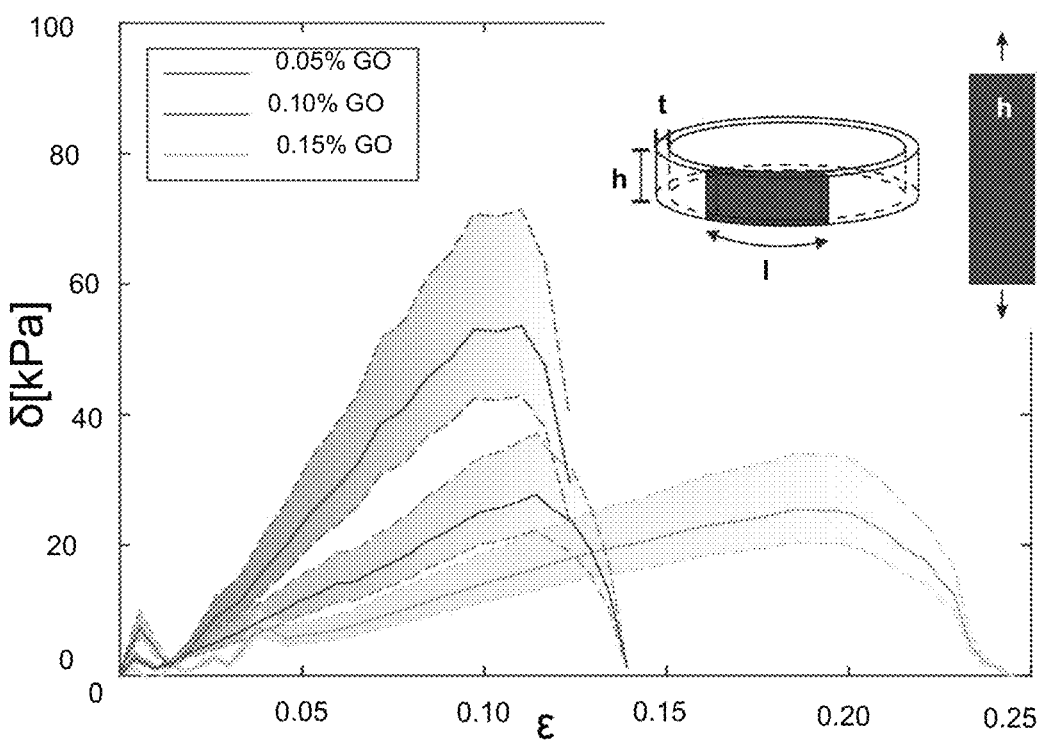

FIG. 17. Tuneable mechanical properties of ELP-GO material.

Nanotensile test results reveal that the strength, the strain at break, and the toughness modulus increased on tubes formed with increasing concentrations of GO but the elastic modulus was highest on tubes made with medium level (0.10%) GO compared to lower (0.05%) and higher (0.15%) amounts based on Weibull statistical distribution.

Figure 18:
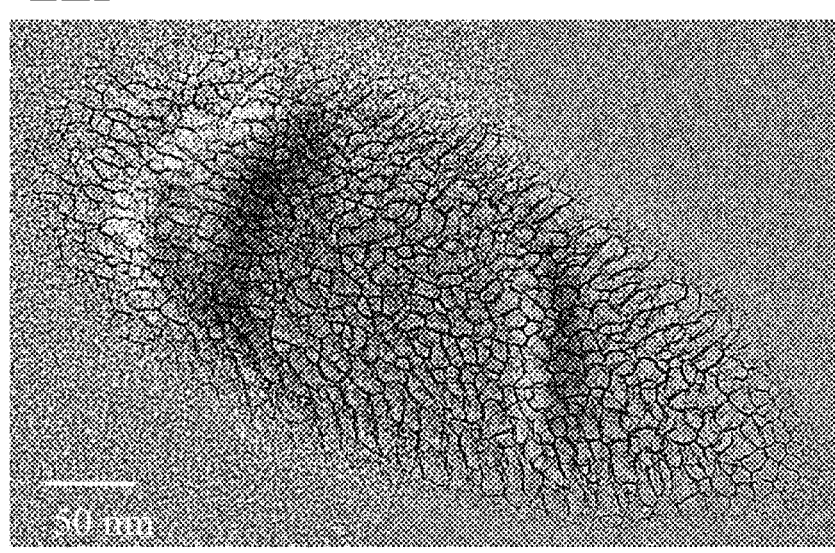
Figure 18:
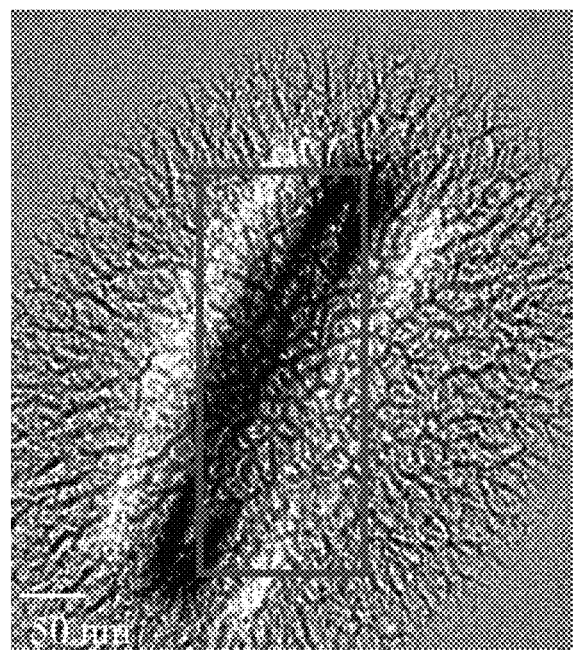

FIG. 18. Control liquid-liquid phase separation (LLPS) of ELP using GO.

Cryo-TEM images show that the GO solution will make ELP aggregate in solution dense, which indicate a LLPS of ELP solution. Control liquid-liquid phase separation (LLPS) of thermodynamic protein (ELP/RLP) using GO. LLPS is a phenomenon based on the unfavourable interactions of two liquids and results in phase separation of solutions even at a low concentration.

Figure 19:
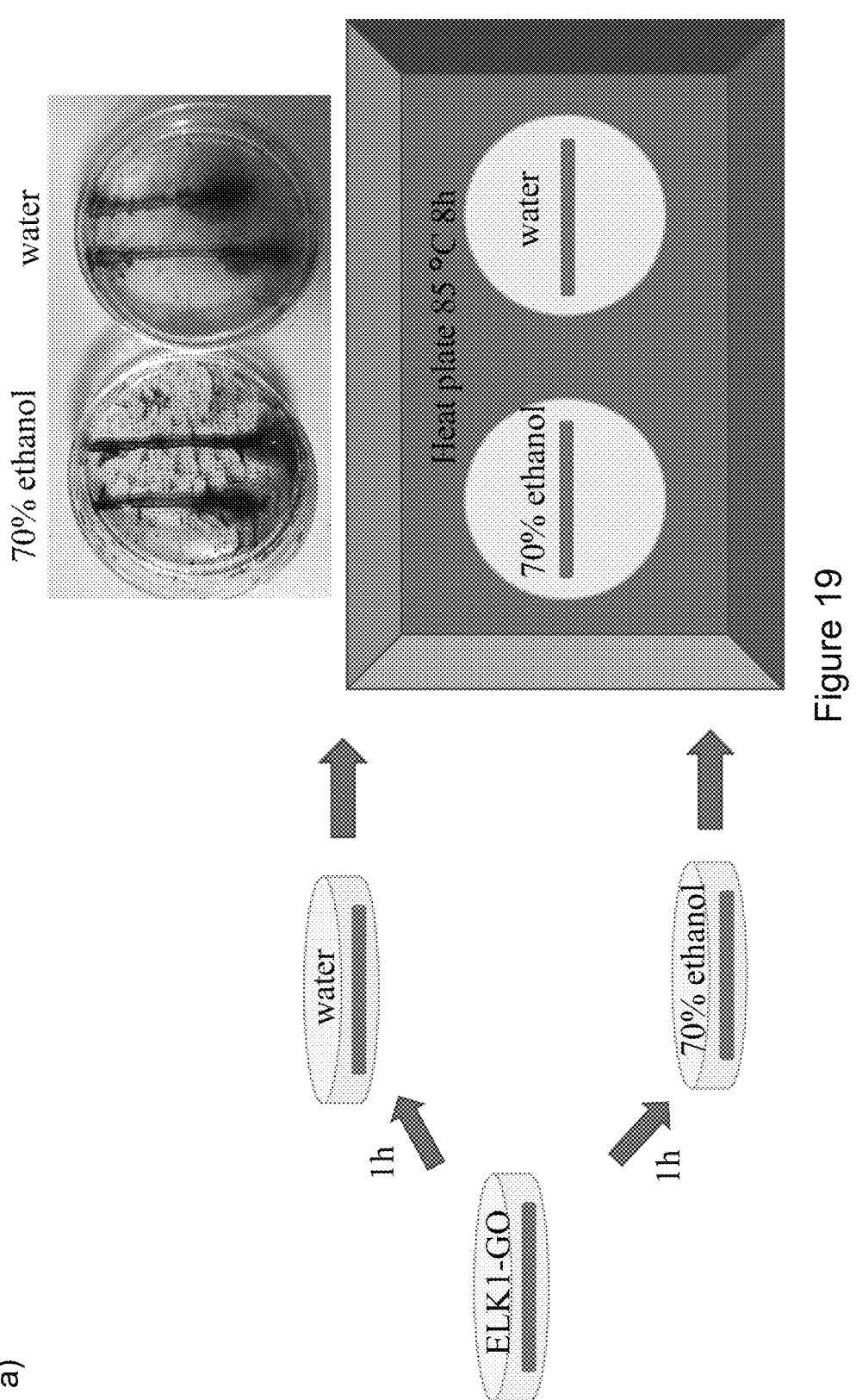
Figure 19:
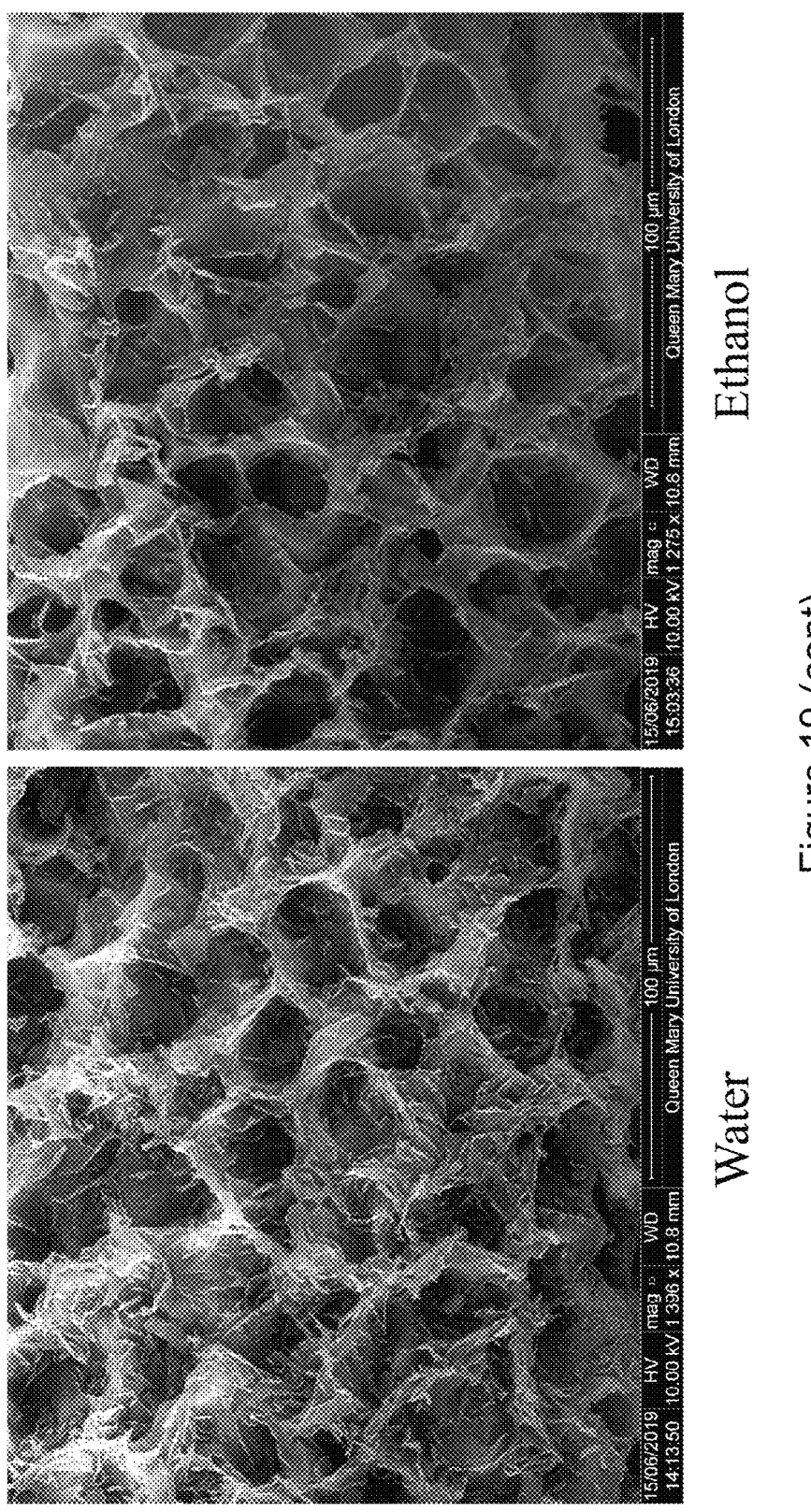

FIG. 19. Reduce GO of ELP-GO materials by heating in 70% ethanol.

a. Illustrator shows the protocol to reduce GO of ELP-GO materials by heating in 70% ethanol at 80° C. for more than 8 h and keep the integrated tubular structure after this procedure. Optical images show the colour of ELP-GO become darker by heating in 70% ethanol but not in water, which indicate the reduced of GO in 70% ethanol. b. SEM images of regular GO (left) and reduced GO (right) of ELP-GO materials. Regular GO is with scrambling sheet structure, while reduced GO is with integrated structure.

EXAMPLES

The invention is now described with reference to the following non-limiting examples:

Materials and Methods

Chemicals

Rhodamine B (95%, HPLC grade) and paraformaldehyde (95%) were obtained from Sigma-Aldrich. Two kinds of GO (GO-L with product number-777676; GO-S with product number-763705) were obtained from Sigma-Aldrich. Alexa Fluor™ 488 NHS Ester (Succinimidyl Ester) was obtained from Thermo Fisher Scientific.

Synthesis and Characterization of Elastin-Like Polypeptides (ELPs)

ELK0, ELK1, and ELK3 molecules were provided by TP Nanobiotechnology (Valladolid, Spain). FIG. 1a shows the sequences, molecular weights, and inverse-phase transition temperature (Tt) of the ELPs. ELPs were synthesised and purified by *E. coli* recombinant expression system. The sequence and molecular weights of the polymers were verified using amino acid analysis. SDS-PAGE and MALDI-TOF SIMS were used to carry out the ELPs characterisation.

Sample Preparation (ELPs-GO System)

Aqueous suspension of GO (0.1% wt, 100 μL) was added to a well of 96-well tissue culture plastic (TCP) and aqueous solution of the ELPs (2% wt, 18 μL) was slowly injected into the suspension of GO. The tip of the pipette was allowed to make contact with the bottom of the well before releasing the ELPs solution vertically at a constant speed. All samples were prepared in MilliQ water.

Temperature-Controlled Spectrophotometry

The thermo-responsive behaviour of ELK1 at certain concentration (2% wt) and pH 8 was determined on a temperature-controlled UV-visible spectrophotometer (Agilent Technologies). ELP samples (2% wt) were prepared in MilliQ water and the pH of the solutions was adjusted with HCl (0.5 M) and $NH_4OH$ (1.0 M) prior to heating at 1° C./min ramping rate. Absorbance of the samples was obtained at λ=350 nm.

Zeta Potential (ζ)

In order to optimize the formation of the ELK1-GO system, the zeta potential of both ELK1 and GO was measured on Zetasizer (Nano-ZS ZEN 3600, Malvern Instruments, UK) at 30° C. under various pH conditions. The concentration of ELK1 and GO used for the measurements is 0.025% wt and 0.00125% wt, respectively. The pH values of the two component solutions were adjusted using HCl (0.5 M) and $NH_4OH$ (1.0 M) and the samples were equilibrated for 10 min at the set temperature prior to the measurement of zeta potential.

Dynamic Light Scattering (DLS)

DLS was performed to measure changes in the particle size of ELK1-GO aggregates at 4° C. (below ELK1's Tt), 30° C. (at the Tt), and 45° C. (above the Tt). The ELK1 and GO were dissolved in MilliQ water at the concentrations of 0.2% and 0.01% separately. The two solutions were mixed in a 1:1 ratio and the particle sizes were measured using Zetasizer (Nano-ZS ZEN 3600, Malvern Instruments, UK). Samples were equilibrated for 10 min at the desired temperature before measurements.

Fluorescence Emission

Fluorescence emission was measured on LS 55 spectrofluorometer (Perkin Elmer). The aqueous solution of GO ($2.5 \times 10^{-3}$% wt, 1.5 mL) and the solution of various concentrations of ELPs (1.5 mL) were mixed in a 10 mm path length cuvette at 30° C. The excitation and emission slits were set at 10 nm. The GO was excited at 255 nm and the emission spectra were collected between 300-700 nm (200 nm/min). The fluorescence emission intensity was recorded at 518 nm. The data were fitted into the Benesi-Hildebrand equation (eq 1) in order to determine the association/binding constant (Ka) between GO and ELPs.

$$1/\Delta I = 1/\Delta I_{max} + (1/K[C])(1/\Delta I_{max}) \qquad (\text{eq 1})$$

Where [C] is the concentration of ELPs, $\Delta I = I - I_{min}$ and $\Delta I_{max} = I_{max} - I_{min}$, where $I_{min}$, I, and $I_{max}$ are the emission intensities of GO considered in the absence of ELPs, at an intermediate ELPs concentration and a concentration of complete saturation, respectively. From the plot of $(I_{max}-I_{min})/(I-I_{min})$ against $[C]^{-1}$ for GO, the value of Ka was determined from the slope.

Circular Dichroism (CD)

Variable temperature CD (VT-CD) measurements were carried out on Chirascan™ CD Spectrometer (Applied Photophysic Limited, U.K.) from 10° C. to 40° C. The solutions of ELK1 (0.01% wt) were prepared in MilliQ water and incubated at each temperature for 10 min before measurements. A quartz cuvette with 0.1 cm path length was used for the measurements and CD spectra were obtained by signal integrating 10 scans, from 190 to 260 nm at speed of 50 nm/min. Data were processed by a simple moving average and smoothing method.

Fourier Transform Infra-Red Spectroscopy (FT-IR)

FTIR analysis was conducted on FTIR spectrometer GX (PerkinElmer®, Waltham, MA, USA). A solution of ELK1 (2% wt) in a mixture of D2O and H2O (75/25 v/v) and the preformed ELK1-GO membranes prepared in the same solution were properly secured over the IR window before scanning. All samples were incubated and formed at 4° C., 30° C., and 45° C. for 10 min before measurements. The program was set to take the average of 160 scans at a resolution of 2 cm$^{-1}$ after subtracting the background and spectra were obtained at wavenumber 4000 cm$^{-1}$ to 600 cm$^{-1}$ with respect to the absorbance for all samples. In order to quantitatively determine the maximum absorption intensity corresponding to various secondary structures of the ELPs ($\alpha$-helix, $\beta$-sheets, $\beta$-turns, and random coils) amide III region (1350-1200 cm$^{-1}$) was analysed using second derivative of a Guassian and Lorentian curve fittings. The second derivative fingerprints for the secondary structures of the ELPs are as follows: 1220-1250 cm$^{-1}$ for $\beta$-sheets, 1250-1270 cm$^{-1}$ for random coils, 1270-1295 cm$^{-1}$ for $\beta$-turns, 1295-1330 cm$^{-1}$ for $\alpha$-helix, as previously suggested by Cai, S. et al.

Scanning Electron Microscopy (SEM) and Wavelength-Dispersive Spectroscopy (WDS)

The microstructures of ELPs-GO and ELK1-GO membranes co-cultured with HUVECs were examined by SEM. ELK1-GO membranes with HUVECs were fixed with 4% paraformaldehyde in MilliQ water for 20 min before dehydration while ELPs-GO membranes were dehydrated directly using increasing concentrations of ethanol (20, 50, 70, 90, 96, and 100%). All samples were subjected to critical point drying (K850, Quorum Technologies, UK) prior imaging. The SEM micrographs were captured on Inspect F50 (FEI Comp, the Netherlands) after sputter-coating with gold (10 nm thick). WDS elemental analyses were performed to study the molecular composition of both the inner and outer surfaces of the ELK1-GO membranes. Quantitative Nitrogen elements (nitrogen exists in ELPs not in GO.) were also analysed using the Inspect F50 (FEI Comp, the Netherlands). All samples consisting only ELPs or GO were prepared for SEM imaging without a prior cross-linking process.

Transmission Electron Microscopy (TEM)

The ELK1 solutions were prepared at 2% wt in MilliQ water. After being aged for 2 hrs at 4° C., 30° C. and 45° C., the ELK1 solutions were loaded onto the carbon film coated copper girds (400 mesh, Agar Scientific, UK) and negatively stained with 2% uranyl acetate (Agar Scientific, UK). The excess staining solution on the grids was removed with filter paper and the grids were allowed to dry at 4° C., 30° C. and 45° C. for at least 3 hrs. Bright field TEM imaging was performed on JEOL 1230 TEM operated at an acceleration voltage of 80 kV and the TEM images were recorded using SIS Mega view III wide angle CCD camera.

Confocal Microscopy

The interaction and localisation of ELK1 and GO was probed using laser scanning confocal and multiphoton microscopy (TCS SP2, Leica Microsystems, Germany). ELK1 (10-6% wt) was dissolved in an aqueous solution of Alexa Fluor™ 488 NHS Ester (2% wt) and GO were diluted to $10^{-6}$% wt with an aqueous solution of Rhodamine (0.1%). All solutions were incubated for 20 min at 30° C. and protected from light. The tubes were fabricated with 50 μL GO-Rhodamine solution and 10 μL ELK1-Alexa Fluor solution in a 96-well Petri dish as previously described. Images were acquired at laser wavelengths of 488 nm and 543 nm which correspond to the excitation wavelength of Alexa Fluor and rhodamine, respectively. Images were further processed using ImageJ.

Small-Angle Neutron Scattering (SANS)

The GO suspension and ELK1 were dissolved in H2O/D2O (25%/75%) respectively with 0.1% and 2%. Small-angle neutron scattering (SANS) measurements were performed on the fixed-geometry, time-of-flight LARMOR diffractometer (ISIS Neutron and Muon Source, Oxfordshire, UK). A white beam of radiation with neutron wavelengths spanning 2.2 to 10 Å was enabled access to Q [Q=4π sin (θ/2)/λ] range of 0.004 to 0.4 Å$^{-1}$ with a fixed-sample detector distance of 4.1 m. Solutions (0.4 mL) of individual components were contained in 1 mm path length UV spectrophotometer grade quartz cuvettes (Hellman) while the composite materials were prepared by mixing equal volume (0.2 mL) of both components in a demountable 1 mm path length cuvettes. The cuvettes were mounted in aluminium holders on top of an enclosed, computer-controlled sample chamber at 30° C. For the variable temperatures experiment (especially those involving ELK1 at 4° C., 30° C. and 45° C.), a thermostatted circulating water bath was fitted with the sample chamber. Time taken for each measurement was approximately 30 min. All scattering data were normalized for the sample transmission, the backgrounds was corrected using a quartz cell filled with D2O or H2O/D2O (25%/75%) and the linearity and efficiency of the detector response was corrected using the instrument-specific software.

In the present SANS experiments, the scattering length density (SLD) of the H2O/D2O (25%/75%) is a volume fraction weighted average of the SLDs of the individual components.

Given the SLDs for H2O and D2O are $-5.6\times10^{-7}$ Å$^{-1}$ and $6.3\times10^{-6}$ Å$^{-1}$, the SLD of the H2O/D2O (25%/75%) is $4.653\times10^{-6}$ Å$^{-1}$ was determined.

Permeability Testing

Fabrication of the Device

The device is produced by pouring a first base layer of PDMS (thickness 1 mm) in a Petri dish. After curing at 60° C. for 60 minutes, a metal needle of 0.8 mm outer diameter is placed on the first layer. A second layer of PDMS is then poured and cured in the dish. The level of PDMS in the second layer must cover the needle. The Petri dish is then placed in an oven at 60° C. for 24 hours to thoroughly cure both PDMS layers. Removal of the tube with forceps leaves a cylindrical cavity with a diameter of 0.8 mm.

Formation of the Membrane

An aqueous suspension of GO (0.1% wt, 20 μL) was added on the device and aqueous solution of ELP (2% wt, 5 μL) was slowly injected into the solution of GO. The tip of the pipette was allowed to make contact with the bottom of the surface before releasing ELP solution vertically at a constant speed. All samples were prepared in MilliQ water.

After the formation of a tube inside the drop of GO, it is necessary to create a flat membrane. With a forceps, it is possible to "cut" the tube and then create a membrane. Subsequently, the membrane is inserted into the device dividing the channel into two chambers.

Pore Size and Porosity

SEM (Scanning Electron Microscopy) was used to determine the porosity and average size of the pores that make up the membrane. The figure represents the inside of ELP-GO tube. Through the Matlab and ImageJ software, the image has been segmented and analyzed.

Epifluorescence Imaging of Diffusion Phenomena

The linear geometry of the device facilitates the characterisation of the transport properties of the membrane, such as effective membrane diffusion or permeability coefficients. To illustrate the use of the device to characterise the diffusivity of a membrane, it is possible to measure the diffusion of FITC-labelled dextran molecules across an ELF/GO membrane. After putting inside the channel ultrapure water (chamber on the left), dextran molecules were added to the water on the right side of the membrane.

The dextran molecules rapidly became uniformly distributed in the right chamber and subsequently diffused across the membrane, increasing the concentration on the left side. It is possible to assert that the dextran molecules are much smaller than the membrane pores (average diameter of a dextran molecule $\approx13$ nm, as provided by the supplier; average pore within the ELF/GO membrane $\approx0.5$ μm, as determined from SEM images), so direct sieving by the membrane is not expected. The time evolution of the fluorescence intensity on the convex side of the membrane is shown in FIG. 4. In this experiment, the intensity profile was obtained by capturing images at selected times via time-lapse fluorescence microscopy and measuring the average intensity on the left side of the membrane using the software ImageJ.

FEM Simulation

In order to have a clearer view of the diffusion process inside the device, an FEM simulation was performed with the COMSOL program. The device was simulated with: in the right-hand chamber the solution with dextran at a concentration of 0.5 mol/m3 and in left chamber only pure water. The simulation describes the process of diffusion from the right to the left chamber in a time interval of 8100 seconds.

Biological Applications

Cell Culture

Human Umbilical Vein Endothelial Cells (hUVECs) (Lonza, Isolated in EGM™-2 Media, C2519A) were cultured in EGM™-2 Media (Lonza, CC-3156& CC-4176). The medium was changed every 3 days until the cells reached 80% confluency. hUVECs between passage 2 and 4 were used for experiments. The tubes were first washed three times with PBS 8 h after assembly and sterilized with UV for 45 min. Then each tube was placed in a well of 48-well cell culture plate with inner or outer side facing up. The EGM™-2 Media (500 μL) containing 50,000 cells was added to each well containing ELK1-GO membranes, coated with ELPs solution (18 μL, 2% wt), GO (20 μL, 0.1% wt GO) or on tissue culture plastic (TCP—positive control). The coated wells were incubated for 8 hrs prior to cell seeding. The cells were incubated at 37° C. and 5% CO2 for different time points for all tests (protocol shown below).

Cell Viability and Proliferation Assay and LIVE-DEAD® Cytotoxicity Assay

The effect of ELK1-GO membranes on hUVECs viability and proliferation using the CellTiter 96® Aqueous One Solution Cell Proliferation Assay (Promega, Southampton, UK). Cells were seeded at a concentration of 50,000 cells/well in 48-well plates. After incubation for 24 hrs, 1 d, 3 d, 5 d, 7 d, cell culture medium was aspirated and 500 μL of EGM™-2 Media containing 10% MTS reagent was added to each well. Plates were subsequently incubated for 3 hrs at 37° C. and the absorbance was read at 490 nm using Infinite F50 plate reader (Tecan, Switzerland). Five replicates of each condition were performed with each assay repeated in triplicate. The cell viability was determined as a percentage of control cell viability and proliferation.

A LIVE-DEAD® Cytotoxicity Assay Kit (Invitrogen, USA) was used to measure the viability of hUVECs seeded on the ELK1-GO membranes. Five replicates of each condition were performed with each assay repeated in triplicate. A stock solution containing calcein AM (1 μM) and ethidium homodimer (2 μM) in PBS was prepared according to the assay instructions, and 200 μL of stock solution was added to each well. Fluorescence images were captured on laser scanning confocal and multiphoton microscopy (TCS SP2, Leica Microsystems, Germany). Viable cells were stained green with calcein AM (ex 495 nm, em 530±12.5 nm), while dead cells red with ethidium homodimer (ex 528 nm, em 645±20 nm).

Immunofluorescence Staining hUVECs on the ELK1-GO membrane were fixed with 4% paraformaldehyde (Sigma, USA), washed and permeabilized with 0.5% Triton X-100 (Sigma, USA), and then rinsed 3 times with PBS. Nonspecific binding sites were blocked by PBS containing 1% BSA. The CD144 marker was labelled by incubating the cells at room temperature for 1 hr with anti-rabbit monoclonal VE-cadherin primary antibody (1:400, Abcam, UK). Cells were then washed and incubated for 50 min at room temperature in Alexa 488 conjugated anti-Rabbit IgG as Secondary Antibody (1:1000, Invitrogen, USA). The stained ELK1-GO membranes were then transferred to slides and visualized on a laser scanning confocal and multiphoton microscopy (TCS SP2, Leica Microsystems, Germany) utilising ×10 and ×40 objectives.

Immunohistology Staining

Slides were first deparaffinized by washing in 2 changes of xylene (Sigma, UK) and graded ethanol baths (absolute ethanol, 90%, 70%). Antigen retrieval was performed to unmask the antigenic epitope of the tissue sample by boiling the deparaffinized sections in citrate buffer (Vector laboratories, UK) at pH 6.0. Endogenous peroxidase activity was blocked by incubating sections in 3% H2O2 solution (Sigma, UK) in PBS at room temperature for 10 min followed by 2 rinses in PBS. To reduce background staining and any other immunostaining application, the samples were incubated with normal goat serum (5% in PBS, Vector laboratories, UK) to block nonspecific binding sites in a humidified chamber at room temperature for 1 hour before staining. After draining the blocking buffer, 100 μL of diluted primary anti-α-SMA antibody (1:500, Abcam, UK) was added to the sections on the slides and incubated in a humidified chamber at room temperature for 1 hr, after which the slides were washed twice in PBS. Then 100 μL of diluted biotinylated secondary antibody (Vector laboratories, UK) was applied to the sections on the slides and incubated in a humidified chamber at room temperature for 30 min with the slides washed in PBS after that. Amplification of antigen was achieved using an Elite® ABC-HRP Kit (Vector Laboratories, UK) and positive staining was visualized by incubating in a peroxidase substrate solution using a DAB Peroxidase (HRP) Substrate Kit (Vector laboratories, UK).

Chick Chorioallantoic Membrane (CAM) Assay

Fertilised chick eggs (*Gallus domesticus*) were kept in a hatchmaster (Brinsea, UK) incubated at 37.5° C. and humidified with rotation. 12 (6 per group: blank control group and ELK1-GO group) day 1 fertilised eggs were maintained within the hatchmaster. After candling the egg to determine if the egg is fertilised a window was created at day 7 under sterile conditions. A window was created by scoring with a scalpel and an approximately 6 mm square opening created in the outer shell of the egg. The membrane was removed from the underlying CAM vascular membrane. ELK1-GO tube samples were inserted into the window and onto the chorioallantoic membrane. Eggs were transferred to a Hatchmaster incubator and incubated for a duration of 8 days at 37.5° C. 60% humidity without rotation. All procedures were performed in accordance with ethical approval and in accordance with the Animal (Scientific Procedures) Act 1986, UK (Project License number P3E01C456). After 8 days of the CAM culture the implanted samples were harvested.

Goldner's Trichrome Staining

CAM samples were prepared as histological slides. Mounted sections were rehydrated through Histo-Clear, graded ethanol's and dH2O before staining for the nuclear counter-stain Weigert's hematoxylin, followed by staining with 0.5% Alcian blue 8GX for proteoglycan-rich cartilage matrix and 1% Sirius red F3B for collagenous matrix. Additionally, slide sections were stained for Goldner's Trichrome to detect bone and osteoid according to standard protocols. Sections were then dehydrated and mounted with DPX before imaging with an Olympus BX-51/22 DotSlide digital virtual microscope using OlyVIA 2.1 software (Olympus Soft Imaging Solutions, GmBH)

Analysis of Goldner's Trichrome Staining by Chalkley Count

The Chalkley point-overlap morphometric technique is a relative area estimate method to measure the abundance of microvessels in an immunohistochemical sample. A "Chalkley point array graticule" was used to fit onto the eyepiece of a microscope. This graticule consists of a grid that contain 25 random dots which can be rotated 360°. An observer can overlay these dots over structures that have stained positively with Goldner's trichrome. The rotational position with the most dots that land on positively stained structures is described as the "Chalkley count" and samples have higher counts are considered to contain a greater abundance of blood vessels. A blank histological slide sample and three ELK1-GO histological slide samples were scoring by this technique.

Co-Assembly of ELK1-GO-hUVECs

EGM™-2 Media containing hUVECs (105 cells/ml) was used to dissolved the ELK1 (2% wt). The ELK1-hUVECs media (10 μL) was added into GO (50 μL, 0.4% wt) solution to make a tube as previously described. All these co-assembled ELK1-GO-hUVECs tubes were incubated at 37° C., 5% CO2 for 24 h, 1 d, 3 d, 5 d prior to LIVE-DEAD® cytotoxicity Assay and SEM procedures as described previously.

Statistical Analysis

GraphPad Prism 5 was applied for data analysis. Student T-test statistical analysis was applied for all the measured data.

Standardized 3D Printing Parameters of ELP-GO Materials

A RegenHU 3DDISCOVERY™ EVOLUTION 3D printer was applied for the 3-D printing of ELP-GO materials. For fabricating the different shapes of structures, an 80 μm inner diameter nozzle was used to release the solution of the ELP under tuneable pressure parameters at a range of speed between 10 mm/s and 100 mm/s. The printing nozzle is merged in a 35 mm diameter Petri dish with 3 mL 0.1% GO MilliQ water solution.

Example 1—Self-Assembly and Material Properties of Graphene Oxide-Protein Matrix a. Sample Preparation (ELPs-GO System)

The inventors used GO sheets of two different average lateral sizes including larger GO (GO-L) measuring 10.5±4.5 μm and smaller GO (GO-S) of 2.3±0.9 μm, both exhibiting a typical hydrophobic surface and negatively charged carboxylic groups on their periphery. The inventors chose ELPs as the protein component because of their modular and disordered nature34 and the possibility to systematically modify their structure.

The ELK1 sequence (FIG. 1*a*) consists of a long penta-block molecule (51.9 kDa) where four of its blocks are hydrophobic (VPGIG) and one is positively charged (VPGKG) and has a transition temperature (Tt) of 30° C. (at 2% ELK1 in MilliQ water). ELPs with similar molecular weight but different levels of charge and hydrophobicity were used as controls (FIG. 1*a*).

Aqueous suspension of GO (0.1% wt, 100 μL) was added to a well of 96-well tissue culture plastic (TCP) and aqueous solution of the ELPs (2% wt, 18 μL) was slowly injected into the suspension of GO. The tip of the pipette was allowed to make contact with the bottom of the well before releasing the ELPs solution vertically at a constant speed. All samples were prepared in MilliQ water.

When an ELK1 solution at its transition temperature (30° C.) is immersed in a larger volume of a GO solution, a multi-layered membrane of up to 50 μm in thickness develops at the interface around the immersed drop maintaining both solutions separated (FIG. 2*a*). This multi-layered structure suggests the emergence of a diffusion-reaction mechanism and the formation of a membrane capable of responding to modifications in local chemical gradients. By touching the interface with any surface within the first few seconds of formation, the membrane adheres, spontaneously and reproducibly opens into a well-defined spherical shape, and can be manipulated to grow into tubular structures with spatiotemporal control (FIG. 2*b*).

b. Material Properties of Graphene Oxide-Protein Matrix

Critically, in this case, the underlying disordered protein-graphene oxide (DP-GO) mechanism of interaction and supramolecular assembly lead to the growth of a material with enhanced properties.

First, the resulting ELK1-GO membrane is both dynamic, enabling opening and controlled anisotropic growth, and highly stable. These membranes can withstand large temperature changes exhibiting no apparent effects on their multi-layered structure when the temperature drops below (down to 4° C.) or raises above (up to 70° C.) the Tt of ELK1. This enhanced stability is also evidenced by the capability to co-assemble capillary-like structures down to about 50 μm in internal diameter and with walls down to 10 μm in thickness (FIG. 2*c*). Furthermore, the assembly can occur in salt-containing solutions such as cell culture media, which enables co-assembly in the presence of cells without affecting the structural integrity of the generated membrane. This capability opens new opportunities to grow robust geometrically complex tissue engineered constructs comprising and embedding cells in the absence of chemical crosslinking agents (FIG. 2*d*).

Grown ELK1-GO tubular structures were able to support the flow of separate solutions at flow rates of at least 8 mL/min without apparent damage and within a couple of minutes after formation. These properties suggest that the ELK1 and GO exhibit both strong interactions at the molecular scale and integration at higher size scales. This was further demonstrated by scanning electron microscopy (SEM) and birefringence, which revealed the presence of GO-containing layers throughout the cross-section of the membrane (FIG. 20. Furthermore, these layers comprised GO sheets and ELK1 as evidenced from confocal microscopy observations (FIG. 2f, top right), with ELK1 decreasing in concentration from the inside to the outside of the membrane (FIG. 2f, graph). This presence of ELK1 throughout the membrane is further supported by the observed adhesiveness of the ELK1-GO membrane.

c. Nanotensile Mechanical Tests

To characterize the resulting mechanical properties of the tubular structures, an established nanotensile test was conducted on tubes made of ELK1 and increasing concentrations of GO (0.05%, 0.10%, 0.15%).

Tensile tests were performed on three kinds of different tube samples: 2% ELK1-0.05% GO, 2% ELK1-0.10% GO, and 2% ELK1-0.15% GO samples to test if the mechanical properties changed with increasing concentration of GO. 40 μL ELP solution was added into 200 μL GO solution in a well of 48-well Petri dish. Rectangular membranes were cut about 10 min after their preparation. Ten samples for each composition were tested. Since the core of these structures is made of GO, density was assumed to be equal to 1.8 g/cm3 based on previous studies. Samples were immediately tested in order to avoid their drying. The main purpose of this test was to characterize the mechanical properties of the bulk material through tensile test. Thus, every type of membrane was tested with a nanotensile machine Agilent Technologies T150 UTM (https://www.agilent.com/home): it is provided with high load resolution (about 50 nN), relatively high maximum load (500 mN) and high displacement resolution (about 0.1 nm).

Membranes were mounted one by one on rectangular paper holders. Both ends of the samples were attached using small amounts of super glue, then each sample holder was mounted in the machine and carefully blocked using two grips. The lateral parts of the paper holder were cut so the machine could perform a traction test and calculate samples mechanical characteristics. Samples had a gauge length of 5 mm and were tested with a strain speed of 0.05%/s. The output of the nanotensile test is a load-displacement curve, from which global properties can be derived. Experimental Young's modulus, strength, strain at break, and toughness modulus were analysed and consequently described by Weibull statistical distribution In the following the Weibull distribution, parameters are obtained by assuming the probability of failure F for a sample of volume V under uniaxial stress a, and related Young's modulus E, strain at break ε, and toughness modulus T. The probability function is expressed as follows (for x equal to σ, E, ε and T):

$$F(x) = 1 - e^{\left[\frac{V}{V0}\left(\frac{x}{x_0}\right)^{\alpha_x}\right]}$$

Where $x_0$ and $\alpha_x$ represent the Weibull's scale and shape parameters, respectively, and $V_0$ is a unit volume. For a generic quantity x, $x_0$ is obtained from the y-intercept of the best fit equation and has the same unit as x, while the cumulative probability estimators for experimental tests can be obtained as:

$$F(x_i) = \frac{1 - 0.5}{N}$$

Where N is the number of tests. All the experimental quantities are ranked in ascending order. For each quantity, $\sigma_0$ (or $E_0$, $\varepsilon_0$, $T_0$) and $\alpha_0$ (or $\alpha_E$, $\alpha_\varepsilon$, $\alpha_T$) are the Weibull's scale and shape parameters respectively. $\sigma_0$, $E_0$, $\varepsilon_0$ and $T_0$ could be considered also as an index of the mean value of the distribution, while $\alpha_0$, $\alpha_E$, $\alpha_\varepsilon$ and $\alpha_T$ are the Weibull modulus.

From the statistical analysis, it is possible to state that the Weibull distribution well describes the mechanical properties of samples, as it is possible to deduce from the high values of R2. Samples with a concentration of 0.10% of GO show a Young's modulus probability distribution that is smoother than the other types of samples. This means that in this case there is a major probability to have high values of E. Thus, it is possible to assert that 0.10% GO samples are stiffer than the others. Apart from the elastic modulus, the other mechanical properties increase when increasing the GO concentration. However, these preliminary results suggest that samples with 0.10% GO could exhibit higher stiffness without compromising its strain and dissipated energy.

As expected, the strength, the strain at break, and the toughness modulus increased on tubes formed with increasing concentrations of GO (FIG. 2g, table). However, based on a Weibull statistical distribution, the results revealed that the elastic modulus was highest on tubes fabricated with 0.10% GO (212.90-247.15 kPa) compared to 0.05% (128.78-147.37 kPa) and 0.15% (159.57-208.16 kPa). This result is also visible from the stress-strain curves of the ELK1-GO (FIG. 2g, graph), where the samples made with 0.1% GO show a steeper slope, meaning that the material is stiffer.

Tables 3 to 9 show Weibull statistics parameters for the mechanical tests and the experimental results obtained from tensile tests.

TABLE 3

| Weibull statistics parameters for the strength of samples, obtained from the best fit curves. | | | | | | |
|---|---|---|---|---|---|---|
| | $\sigma_{0\,max}$ [kPa] | $\sigma_{0\,min}$ [kPa] | $\alpha_\sigma$ | $\beta_\sigma$ t = 0.03 | $\beta_\sigma$ t = 0.05 | $R^2$ |
| 0.05% | 19.58 | 14.65 | 2.31 | 6.88 | 6.21 | 0.93 |
| 0.10% | 21.74 | 19.30 | 1.30 | 4.01 | 3.86 | 0.85 |
| 0.15% | 34.10 | 29.07 | 1.45 | 5.13 | 4.90 | 0.81 |

$\sigma_{0\,max}$ and $\sigma_{0\,min}$ refer to the minimum and maximum thickness t respectively.

TABLE 4

| Weibull statistics parameters for the Young's modulus of samples, obtained from the best fit curves. | | | | | | |
|---|---|---|---|---|---|---|
| | $E_{0\,max}$ [kPa] | $E_{0\,min}$ [kPa] | $\alpha_E$ | $\beta_E$ t = 0.03 | $\beta_E$ t = 0.05 | $R^2$ |
| 0.05% | 147.37 | 128.78 | 1.36 | 6.78 | 6.60 | 0.88 |
| 0.10% | 247.15 | 212.90 | 1.41 | 7.78 | 7.57 | 0.95 |
| 0.15% | 208.16 | 159.57 | 2.08 | 11.12 | 10.57 | 0.88 |

$E_{0\,max}$ and $E_{0\,min}$ refer to the minimum and maximum thickness t respectively.

TABLE 5

| | Weibull statistics parameters for the strain at break of samples, obtained from the best fit curves. | | | | |
|---|---|---|---|---|---|
| | $\varepsilon_{0\,max}$ [—] | $\varepsilon_{0\,min}$ [—] | $\alpha_\varepsilon$ | $\beta_\varepsilon$ t = 0.03 | $\beta_\varepsilon$ t = 0.05 | $R^2$ |
| 0.05% | 0.07 | 0.09 | 1.76 | 4.80 | 4.29 | 0.87 |
| 0.10% | 0.16 | 0.19 | 2.68 | 4.90 | 4.39 | 0.88 |
| 0.15% | 0.22 | 0.27 | 2.37 | 3.61 | 3.09 | 0.65 |

$\varepsilon_{0\,max}$ and $\varepsilon_{0\,min}$ refer to the minimum and maximum thickness t respectively.

TABLE 6

| | Weibull statistics parameters for the toughness modulus of samples, obtained from the best fit curves. | | | | |
|---|---|---|---|---|---|
| | $T_{0\,max}$ [mJ/g] | $T_{0\,min}$ [mJ/g] | $\alpha_T$ | $\beta_T$ t = 0.03 | $\beta_T$ t = 0.05 | $R^2$ |
| 0.05% | 0.55 | 0.48 | 1.33 | −0.80 | −0.97 | 0.92 |
| 0.10% | 1.12 | 1.11 | 1.02 | 0.12 | 0.11 | 0 84 |
| 0.15% | 3.50 | 2.10 | 1.21 | 1.12 | 0.90 | 0.75 |

$T_{0\,max}$ and $T_{0\,min}$ refer to the minimum and maximum thickness t respectively.

TABLE 7

| | Mechanical tests results for samples with 0.05% of GO, | | | | | | |
|---|---|---|---|---|---|---|---|
| | $E_{max}$ [kPa] | $E_{min}$ [kPa] | $\sigma_{max}$ [kPa] | $\sigma_{min}$ [kPa] | $\varepsilon_m$ [—] | $\varepsilon_u$ [—] | $T_{max}$ [mJ/g] | $T_{min}$ [mJ/g] |
| Test 1 | 461.63 | 276.98 | 23.51 | 14.11 | 0.21 | 0.28 | 1.95 | 1.17 |
| Test 2 | 117.89 | 70.74 | 44.87 | 26.92 | 0.28 | 0.31 | 3.61 | 2.17 |
| Test 4 | 198.36 | 119.02 | 21.49 | 12.90 | 0.13 | 0.17 | 1.32 | 0.79 |
| Test 5 | 185.30 | 111.18 | 57.66 | 34.60 | 0.23 | 0.26 | 4.01 | 2.41 |
| Test 6 | 343.85 | 206.31 | 37.11 | 22.27 | 0.11 | 0.14 | 1.49 | 0.90 |
| Test 7 | 673.10 | 403.86 | 52.33 | 31.40 | 0.07 | 0.13 | 1.88 | 1.13 |
| Test 9 | 1137.03 | 682.22 | 26.43 | 15.86 | 0.05 | 0.07 | 0.50 | 0.30 |
| Test 10 | 354.08 | 212.45 | 65.76 | 39.45 | 0.13 | 0.14 | 2.86 | 1.72 |
| Test 11 | 313.29 | 187.98 | 15.72 | 9.43 | 0.07 | 0.08 | 0.36 | 0.22 |
| Test 12 | 2533.44 | 1520.06 | 51.47 | 30.88 | 0.06 | 0.08 | 1.64 | 0.98 |

TABLE 8

| | Mechanical tests results for samples with 0.10% of GO. | | | | | | |
|---|---|---|---|---|---|---|---|
| | $E_{max}$ [kPa] | $E_{min}$ [kPa] | $\sigma_{max}$ [kPa] | $\sigma_{min}$ [kPa] | $\varepsilon_m$ [—] | $\varepsilon_u$ [—] | $T_{max}$ [mJ/g] | $T_{min}$ [mJ/g] |
| Test 1 | 190.71 | 114.42 | 49.59 | 29.75 | 0.24 | 0.29 | 3.67 | 2.20 |
| Test 2 | 1063.90 | 638.34 | 27.31 | 16.39 | 0.15 | 0.44 | 1.76 | 1.06 |
| Test 3 | 964.28 | 578.57 | 45.10 | 27.06 | 0.03 | 0.33 | 3.31 | 1.98 |
| Test 4 | 870.28 | 522.17 | 334.08 | 200.45 | 0.22 | 0.32 | 30.36 | 18.21 |
| Test 6 | 437.63 | 262.58 | 12.46 | 7.48 | 0.13 | 0.17 | 0.73 | 0.44 |
| Test 7 | 810.44 | 486.26 | 71.44 | 42.87 | 0.11 | 0.12 | 2.64 | 1.59 |
| Test 8 | 347.09 | 208.25 | 52.71 | 31.63 | 0.15 | 0.19 | 3.31 | 1.99 |
| Test 9 | 1991.04 | 1194.62 | 130.71 | 78.43 | 0.08 | 0.44 | 16.66 | 10.00 |
| Test 10 | 639.44 | 383.67 | 76.94 | 46.16 | 0.18 | 0.26 | 6.00 | 3.60 |
| Test 11 | 294.72 | 176.83 | 33.34 | 20.01 | 0.12 | 0.17 | 1.68 | 1.01 |
| Test 12 | 92.73 | 55.64 | 10.94 | 6.56 | 0.12 | 0.14 | 0.40 | 0.24 |

TABLE 9

| | Mechanical tests results for samples with 0.15% of GO. | | | | | | |
|---|---|---|---|---|---|---|---|
| | $E_{max}$ [kPa] | $E_{min}$ [kPa] | $\sigma_{max}$ [kPa] | $\sigma_{min}$ [kPa] | $\varepsilon_m$ [—] | $\varepsilon_u$ [—] | $T_{max}$ [mJ/g] | $T_{min}$ [mJ/g] |
| Test 1 | 207.86 | 124.72 | 37.52 | 22.51 | 0.26 | 0.27 | 2.03 | 1.22 |
| Test 2 | 286.85 | 172.11 | 44.40 | 26.64 | 0.29 | 0.37 | 4.04 | 2.42 |
| Test 3 | 261.16 | 156.70 | 119.87 | 71.92 | 0.39 | 0.55 | 17.52 | 10.51 |
| Test 4 | 236.31 | 141.79 | 221.89 | 133.13 | 0.68 | 0.69 | 15.23 | 9.14 |
| Test 5 | 670.22 | 402.13 | 69.22 | 41.53 | 0.12 | 0.19 | 4.24 | 2.54 |
| Test 6 | 877.23 | 526.34 | 97.59 | 58.55 | 0.20 | 0.30 | 7.66 | 4.60 |
| Test 7 | 276.14 | 165.68 | 68.86 | 41.32 | 0.17 | 0.22 | 4.15 | 2.49 |
| Test 8 | 482.86 | 289.72 | 56.48 | 33.89 | 0.18 | 0.24 | 4.05 | 2.43 |
| Test 9 | 150.05 | 90.03 | 19.35 | 11.61 | 0.29 | 0.32 | 1.63 | 0.98 |
| Test 11 | 214.86 | 128.91 | 34.04 | 20.42 | 0.19 | 0.24 | 2.50 | 1.50 |

These insights further demonstrate that the properties of the material result from the interactions between both components. These results were also confirmed qualitatively by assessing tube geometry visually and robustness manually.

Example 2—Biofabrication and Self-Assembling Fluidic Devices

Taking advantage of the spontaneous assembly, stability and robustness, dynamic properties, and adhesiveness of the ELK1-GO system, it was possible to grow tubular structures as bridges between gaps by touching two distant surfaces while injecting the ELK1 solution into the GO solution (FIG. 2e). As the material touches a surface soon after co-assembly, it adheres, opens, and seals to the surface, enabling growth by continual injection of ELK1 solution until the next surface touch. Given the capability to incorporate cells during the assembly process, the inventors successfully attempted to grow capillary-like structures having cells embed within and on the tube wall (FIG. 2d). Based on this simple, yet robust, tubular assembly and growth, as well as the capacity to incorporate cells and immediately withstand flow of solutions, this enables the use of rapid-prototyping techniques to control co-assembly spatio-temporally and fabricate more complex capillary-based microfluidic devices (FIG. 2h, 2i). To demonstrate this, the inventors used an extrusion-based 3-D printer to print the ELK1 solution within a GO solution. Through this approach, the inventors fabricated fluidic devices containing high-aspect ratio tubular structures of different internal diameters and comprising curves (FIG. 2h (i)), angles of different sizes (FIG. 2h (i), (iv)), and bifurcations (FIG. 2h (i), (iii)). The fluidic devices were able to withstand aqueous flows of at least 2 mL/min for at least 10 min and within 20 min of formation (FIG. 2h (ii), (iii)).

Example 3—Biological Validation and Cell Culture

The capacity of the material to self-assemble in cell friendly environments opens opportunities to biofabricate complex and functional capillary-based fluidic devices that may offer a higher level of biological relevance compared with traditional devices. This potential was assessed by suspending human umbilical vascular endothelial cells (hUVECs) within the ELK1 solution prior to co-assembly and growing the tubes in a similar manner.

a. Cell Culture

Human Umbilical Vein Endothelial Cells (hUVECs) (Lonza, Isolated in EGM™-2 Media, C2519A) were cultured in EGM™-2 Media (Lonza, CC-3156& CC-4176). The medium was changed every 3 days until the cells reached 80% confluency. hUVECs between passage 2 and 4 were used for experiments. The tubes were first washed three times with PBS 8 h after assembly and sterilized with UV for 45 min. Then each tube was placed in a well of 48-well cell culture plate with inner or outer side facing up. The EGM™-2 Media (500 μL) containing 50,000 cells was added to each well containing ELK1-GO membranes, coated with ELPs solution (18 μL, 2% wt), GO (20 μL, 0.1% wt GO) or on tissue culture plastic (TCP—positive control). The coated wells were incubated for 8 hrs prior to cell seeding. The cells were incubated at 37° C. and 5% CO2 for different time points for all tests.

Fluorescence microscopy revealed the cells were present both within the assembled ELK1-GO membrane as well as inside the lumen of the corresponding tubes right after co-assembly (FIG. 2d).

As the diffusion-reaction mechanism of formation takes place, cells located at the interface between both solutions are either trapped within or adhered to the assembling membrane. At this point, cells suspended in the newly enclosed ELP solution further bind to the inner wall (lumen) of the tube. Cells were observed to spread and grow for at least 7 days both within the membrane and on the lumen of the tubular structures, indicating that the material is able to support cell survival and growth.

To confirm this finding, cell adhesion, proliferation and viability assays were conducted on both sides of ELK1-GO wall of preformed tubes (using the CellTiter 96® Aqueous One Solution Cell Proliferation Assay (Promega, Southampton, UK) and A LIVE-DEAD® Cytotoxicity Assay Kit (Invitrogen, USA)).

Remarkably, cells were found to adhere and proliferate at similar levels as those growing on tissue culture plastic surface (FIG. 3a, b), forming a confluent layer on both sides of the membrane (FIG. 3c). To further assess the cell behaviour on the tubular structures, VE-cadherin (CD144) was labelled to observe the organization of the intercellular junctions, which may be critical for the formation of an intact endothelial monolayer. Confocal images revealed that hUVECs were able to form an integral monolayer on both sides of the ELK1-GO membrane (FIG. 3d). The formation of such intercellular junctions is of particular implication for the vasculogenesis on the ELK1-GO membrane.

This notable cell growth and spread on the co-assembled membranes suggests that the hybrid material is cell friendly in vitro. While ELP materials have been shown to support cell growth39,40, GO is known to be cytotoxic to endothelial cells in vitro at concentrations higher than 100 ng/mL as a result of plasma membrane damage and oxidative stress. It may be important to keep in mind that GO cytotoxicity depends on the inherent properties of the specific GO used. Based on our results, negligible cytotoxicity was observed on the ELK1-GO membranes even when using GO concentrations of up to 4 mg/mL.

Example 4—Underlying Molecular Mechanism and Interactions

Here, the inventors demonstrate that the GO lamella conformation in aqueous environments and its flat-sheet organization at air-liquid interfaces would provide both a supramolecular framework for interaction with disordered ELP molecules as well as the capacity to form a diffusion barrier upon co-assembly. In this way, the inventors demonstrate that the co-assembly of GO and ELPs leads to a supramolecular system driven by a diffusion-reaction process that can be guided to generate a dynamic multi-layered membrane (FIG. 2a, b, f) with enhanced properties (FIG. 2c, e, d, g) and functionality (FIG. 2h, FIG. 3).

The inventors first tested the presence of both electrostatic and hydrophobic forces by quantifying ELK-GO binding constants using ELPs with varying levels of charge and hydrophobicity. Tubes formed on application of ELK1 and ELK3 but not ELK0, confirming the need for electrostatic forces for its assembly. MD simulations revealed that these electrostatic interactions are first to take place. Interestingly, the highest binding constant (Ka) was obtained with ELK1 ($1.3 \times 10^6$) compared to ELK0 ($7.2 \times 10^4$) and ELK3 ($3.2 \times 10^5$) (FIG. 4a).

To further explore the role of electrostatic forces, the inventors formed tubes with ELP and GO solutions at varying pHs and again found that more robust membranes formed when the charge difference between both components was marginal (FIG. 4c, d). These results suggest that optimum co-assembly does not solely depend on electrostatic forces but rather on a synergistic effect between both electrostatic and hydrophobic forces, which the inventors infer could be related to the 3D conformation of the ELK1 and its ability to interact with the GO lamellae. To test this hypothesis, and taking advantage of the ELP's capacity to change its conformation at different temperatures (FIG. 4e, graph), the inventors assembled tubes using GO and ELK1 (2% wt) at either below (4° C.), above (45° C.), or the ELK1's Tt (30° C.) (FIG. 4e). While tubes formed at all temperatures, they were more robust and exhibited better-defined multilayers and tubular geometry (FIG. 4e, images) at 30° C., suggesting stronger interactions at this temperature. This enhanced interaction was confirmed by DLS, which revealed the presence of larger ELK1-GO aggregates at 30° C. compared to 4° C. and 45° C. (FIG. 40. These results indicate that the 3D conformation of ELK1 at the different temperatures determines its interaction with the GO lamellae, which would in turn play a role in the diffusion-reaction mechanism and consequently on the structure and properties of the resulting ELK1-GO tubes (FIG. 4e, images).

a. ELK1-GO Conformations

To shed light on this enhanced ELK1-GO interaction at 30° C., the inventors used small angle neutron scattering (SANS) and found that, as expected, ELK1 exhibited an expanded conformation at 4° C. and a collapsed aggregated conformation with a 74 nm radius of gyration core at 45° C. Furthermore, at 30° C., the molecule acquired a conformation that combined both an expanded structure and a collapsed aggregate core, consisting of a 60 nm radius of gyration core surrounded by a larger 500 nm radius corona of expanded structures. These conformations were investigated by transmission electron microscopy (TEM). On the other hand, GO sheets are known to stack and form lamellae in aqueous environments, which was confirmed by MD simulation. Is important to mention that although MD simulations were generated using smaller GO sheets, they have been shown to behave similarly to larger ones in terms of solution behaviour of GO at the molecular level and their propensity to form lamellae. The inventors hypothesised that the disordered nature of ELK1 could contribute to its interaction with the GO lamella. To test this hypothesis, the inventors used SANS to investigate the size and shape of the ELK1-GO aggregates upon co-assembly (FIG. 5a).

The inventors found that at 30° C., the GO and ELK1 aggregate acquires a classical core-shell-bicelle-elliptical model47 with a core measuring 7 nm in length, a thick_rim of 22 nm, and a thick_face of 16 nm. In this model, the core is formed by GO and the shell by ELK1. This core-shell conformation was confirmed by confocal microscopy (FIG. 5b). On the other hand, at 4° C. and 45° C., the ELK1-GO aggregates acquire longer cores and thinner shells, which suggests that at these temperatures the GO lamellae are less infiltrated by ELK1 molecules. In contrast, at 30° C., the shorter core of the ELK1-GO aggregates indicates that the GO lamella stacks are more infiltrated by and likely interacting more with the ELK1. This difference in aggregation was also confirmed by MD simulation.

b. Disorder-to-Order Transitions to Enhance Integration

The inventors hypothesize that this enhanced infiltration by ELK1 within the GO lamella at 30° C. is associated to the disordered nature of the ELK1 and its ability to acquire different secondary structures upon interaction with other molecules. The inventors first used FTIR amide III spectra to conduct a quantitative analysis of the ELK1's secondary structure20,48. The results confirmed that ELK1 at 30° C. comprises a variety of secondary structures including α-helix, β-sheet, β-turn, and random coil (FIG. 5d). Interestingly, at 30° C. and prior to co-assembly, ELK1 exhibits higher amounts of α-helix and lower amounts of β-sheet compared to the ELK1 at 4° C. and 45° C. (FIG. 5d). This increased α-helix was verified by circular dichroism (CD) and hydrogen bond estimation algorithm (DSSP) based on MD simulations. While the presence of α-helix in ELPs is not common, previous studies have confirmed that lysine-rich ELP sequences can exhibit α-helix49. In addition, it has been found that, upon binding with GO, proteins rich in α-helix exhibit an increased protein-GO aggregate stability50. It is possible that the increased α-helix present in ELK1 at 30° C. decreases the entropy of the system by enhancing the ELK1-GO aggregate stability compared to 4° C. and 45° C., generating a more stable ELK1-GO diffusion barrier at the beginning of the co-assembly process. This more stable diffusion barrier would then have an effect on the assembly of the membrane, as has been previously reported for interfacial systems. From qualitative observations, tubes assembled at 30° C. seemed to develop from a better-defined diffusion barrier compared to those at 4° C. and 45° C. To further confirm this, the inventors attempted to form tubular structures using the GO-S, which instead lead to a gel-like structure, suggesting the formation of a weaker and more permeable diffusion barrier. Furthermore, it is possible that the increase in ELK1-GO stability causes a slower diffusion-reaction process as the ELK1 infiltrates the GO lamella.

To shed light on this phenomenon, MD simulations confirmed that ELK1-GO interactions are slower at 30° C. compared to those at 4° C. and 45° C. The inventors speculate that this slower interaction, diffusion, and multi-layered assembly may facilitate the observed increase in β-sheet at 30° C. It is known that higher levels of β-sheet conformation generate more collapsed and denser aggregates.

Consequently, it is possible that increasing levels of β-sheet within the ELK1-GO complex may further lead to denser ELK1 aggregation within the GO lamella. As ELK1 diffuses through the GO lamella at 30° C., ELK1 binds to and interacts with the GO and consequently changes its conformation (FIG. 5d).

Proteins rich in disordered regions are known to change their conformation upon binding to other molecules or surfaces. This change in conformation then enables the ELK1 to infiltrate within the GO lamellae (FIG. 5a, b, d). The inventors speculate that this infiltration is aided by the small aggregate hydrophobic core of ELK1 binding primarily with the hydrophobic surface of GO while the larger and positively charged corona of ELK1 binds with the negatively charged edge of GO.

Example 5-3D Printing of ELP/GO Materials

A PAM2 system (Centro Piaggio, Pisa University, Italy) was applied for the 3-D printing of ELK1-GO materials. Blue food dye (5 μL) was added into aqueous solution of ELK1 (2 mL, 2% wt) to make the printing procedure visible. For fabricating the different shapes of structures and the 60 μm diameter small tube, a 65 μm diameter glass tube tip was used as nozzle to release the solution of the ELK1 and the dye under 4 kPa pressure at a range of speed between 10 mm/s and 18 mm/s. The printing nozzle is merged in a container with 0.1% GO MilliQ water solution. All the 3D pathway was controlled by the Repetier software. A peristaltic pump was used to perfuse 1 v/v green food dye in MilliQ water. For the vertical tube, the perfusion speed is from 4.7 mL/min to 8.3 mL/min. For other structures, the perfusion speed was 2 mL/min.

A RegenHU 3DDISCOVERY™ EVOLUTION 3D printer was applied for the 3-D printing of ELP-GO materials. For fabricating the different shapes of structures, an 80 µm inner diameter nozzle was used to release the solution of the ELP under tuneable pressure parameters at a range of speed between 10 mm/s and 100 mm/s. The printing nozzle is merged in a 35 mm diameter Petri dish with 3 mL 0.1% GO MilliQ water solution.

Example 6—Carbonisation and Reduced GO of the GO-DP Structures

ELK1-GO membranes, prepared as described herein, were heated to 1000° C. for 4 hr by Carbolite STF tubular furnace. This reduces the graphene oxide to graphene. SEM images show that the structures retain the multilayer structure after heating (FIG. 7). The structure also becomes conductive (as graphene is an excellent electrical conductor). To reduce GO of ELP-GO materials by heating in 70% ethanol. Optical images (FIG. 19*a*) show the colour of ELP-GO become darker by heating in 70% ethanol but not in water, which indicate the reduced of GO in 70% ethanol. SEM (FIG. 19*b*) images of regular GO (left) and reduced GO (right) of ELP-GO materials. Regular GO is with scrambling sheet structure, while reduced GO is with integrated structure.

Table 10 shows the results of conductivity tests carried out on the reduced-GO-protein membranes which have been heated to 1000° C.

TABLE 10

| 1000° C. | Length (m) | Width (m) | Thickness (m) | Cross-section area (m) | Electrical resistance (Ω) | Electrical conductivity (S/m) |
|---|---|---|---|---|---|---|
| 1 | 0.00282 | 0.00376 | 0.00001 | 3.76E−08 | 6.44 | 11645.96 |
| 2 | 0.00282 | 0.00376 | 0.00001 | 3.76E−08 | 6.39 | 11737.09 |
| 3 | 0.00282 | 0.00376 | 0.00001 | 3.76E−08 | 6.18 | 12135.92 |
| | | | | | Average | 11839.66 |

The electrical conductivity of the reduced GO-protein structures was measured under ambient conditions using a standard two-probe method. 40 nm silver contacts were patterned onto thin graphene-protein membranes as the electrodes through a shadow mask for a better ohmic contact. Conductivity (σ) is the reciprocal of the resistivity (ρ) and measures the ability of a material to conduct an electric current. Therefore σ=1/ρ and has the unit of siemens per metre, S/m. Conductivity ranges from zero (for a perfect insulator) to infinity (for a perfect conductor).

$\sigma = l/RA$ (l=length, R=electrical resistance, A=cross-section area)

$A = T*W$ (T=thickness, W=width)

The conductivity of the GO-protein structure is zero before reduction by heating takes place indicating the GO-protein structure is an insulator before reduction. Once the structure has been heated to 1000° C. and the GO reduced to graphene the conductivity is 11839.66 S/m. This data shows the reduced-GO-protein membrane is conductive once reduced. This demonstrates the possibility of making the materials described herein conductive while retaining the multi-layered structures.

Example 7—Tuneable Porosity & Permeability of ELK1-GO Material

Fabrication of the Device

The device is produced by pouring a first base layer of PDMS (thickness 1 mm) in a Petri dish. After curing at 60° C. for 60 minutes, a metal needle of 0.8 mm outer diameter is placed on the first layer and two pins for subsequent alignment of the device. A second layer of PDMS is then poured and cured in the dish. The level of PDMS in the second layer must cover the needle. The Petri dish is then placed in an oven at 60° C. for 24 hours to thoroughly cure both PDMS layers. Removal of the tube with forceps leaves a cylindrical cavity with a diameter of 0.8 mm.

Formation of the Membrane

After the formation of a tube inside the drop of GO, it is necessary to create a flat membrane (FIG. 12*a*). With forceps, it is possible to "cut" the tube and then create a membrane. Subsequently, the membrane is inserted into the device dividing the channel into two chambers (FIG. 12*a*). SEM (FIG. 13) was used to determine the porosity and average size of the pores that make up the membrane. The porosity is directly connected with the diffusion and permeability of the membrane, for this reason it may be important to determine the porosity as it allows to understand which kind of molecules can cross the membrane. The figure represents the porosity inside of ELP/GO tube. Through the Matlab and ImageJ software, the image has been segmented and analyzed in order to find the porosity and the pores size.

Epifluorescence Imaging of Diffusion Phenomena

The linear geometry of the device facilitates the characterization of the transport properties of the membrane, such as effective membrane diffusion or permeability coefficients. To illustrate the use of the device to characterize the diffusivity of a membrane, it is possible to measure the diffusion of FITC-labelled dextran molecules across an ELF/GO membrane. After putting inside the channel ultrapure water (chamber on the left), dextran molecules were added to the water on the right side of the membrane (FIG. 14*a*).

The dextran molecules rapidly became uniformly distributed in the right chamber and subsequently diffused across the membrane, increasing the concentration on the left side. It is possible to assert that the dextran molecules are much smaller than the membrane pores (average diameter of a dextran molecule ≈13 nm, as provided by the supplier; average pore within the ELP/GO membrane ≈0.5 µm, as determined from SEM images), so direct sieving by the membrane is not expected.

FITC-Dextran 20 Kda Permeability.

To understand if that constant is comparable with the permeability constants of vivo tissue. It has been compared with some values shown in the table. As can be seen from table 11, the permeability values of ELP/GO membrane are comparable and similar to the permeability constants of BBB chip model and in vivo tissue.

TABLE 11

| | FITC-dextran 20 kDa |
| Model | (10–6 cm/s) |
| --- | --- |
| In vivo | 0.45 |
| 3D microvessel chip | 3 |
| BBB chip model | 2 |
| Vascular Network and Astrocytes | 1.8/0.45 |
| ELMC Pc | 2.23 |
| HUVEC Pc | 3.8 |
| ELP/GO | 4.9 |

Permeability coefficients measured in various models by 20 kDa FITC-dextran

Fluorescein Sodium Salt Permeability

Using the same equation and procedure, it was possible to measure and observe the diffusion of sodium molecules across the membrane. Using equation 1 it is possible to measure the constant permeability. In this experiment the parameters was: Ci is the initial fluorescence intensity in the right side of the membrane, V is the volume of both chambers (3.16*10-9 m3), Cf is the final concentration intensity in the left chamber of the membrane, T is the time (3.100 s) and A is the area of the membrane. Consequently, the Permeability coefficient for dextran across the specific membrane considered can be estimated to be P≅4.6*10-5 cm/s.

Using this equation:

$$D = P * L$$

Where L is the thickness of the membrane, it is possible to measure the diffusion constant. The diffusion constants depend on the thickness of the membrane, it turned out to be equal to 1.5*10-6 cm2/s.

To understand if that constant is comparable with the permeability constants of vivo tissue, It has been compared with some values shown in table 12. As can be seen from the table, the permeability values of ELP/GO membrane are higher than the permeability constants of BBB chip model and in vivo tissue. This difference is due to the fact that the permeability constants of BBB model and in vivo depend on the use of cells on the membrane decreasing the permeability constant.

TABLE 12

Permeability coefficients measured in various models by Fluorescein sodium salt.

| Model | Fluorescein Sodium Salt (10–5 cm/s) |
| --- | --- |
| Inward retina | 0.15 |
| Outward retina | 5.6 |
| BBB chip model | 2.3 |
| ELP/GO | 4.6 |

TABLE 13 cells confluence on the surface of the membranes

| HUVECs concentration | Confluence |
| --- | --- |
| $5 \times 10^3$ | <50% |
| $10^4$ | 60 + 70% |

TABLE 13-continued cells confluence on the surface of the membranes

| HUVECs concentration | Confluence |
| --- | --- |
| $5 \times 10^4$ | 80 + 90% |
| $10^5$ | >95% |

As can be seen from table 13, the percentage of confluence increases with increasing cell density. HUVECs cells have a diameter of about 20 μm and therefore, increasing the peremptory confluence will create a cellular layer that will completely cover the membrane and consequently its pores.

FITC-Dextran 40 kDa Permeability Constant

Using the epifluorescence microscope, picture of the device with dextran was obtained at different time intervals. Subsequently with ImageJ software the various intensity values of the chamber on the left were measured during this time interval. This procedure was applied to all membranes with different cell densities and to the control membrane Assuming that the light intensity is proportional to the dextran concentration, the data can be used to extract an effective permeability coefficient P associated to transport within the membrane. The permeability coefficient P was calculated from the following equation [2]:

$$P = \frac{Cf * V}{Ci * T * A} \tag{2}$$

Where Ci is the initial fluorescence intensity in the right side of the membrane, V is the volume of both chambers (9×10-10 m3), Cf is the final concentration intensity in the left chamber of the membrane, T is the time (10.800 s) and A is the area of the membrane. Consequently, the Permeability coefficient for dextran across the specific membrane considered can be estimated to be P≅2,2×10–6 cm/s. The same process was used to calculate the permeability of membranes with various cell densities. Using equation (2) of permeability coefficient P, the different constants of permeability were measured. The FITC-Dextran 40 kDa permeability constants have been reported in the table below (Table 14).

TABLE 14 summary of the permeability constants

| Cell density (cells/mL) | FITC-Dextran 40 kDa Permeability constant $10^{-6}$ cm/s |
| --- | --- |
| Control (ELK1-GO membrane) | 2.2 |
| $5 \times 10^3$ | 1.2 |
| $10^4$ | 0.72 |
| $5 \times 10^4$ | 0.65 |

Clauses

Aspects and features of the present invention include those set out in the following numbered clauses.

1. A method of preparing a graphene oxide-protein matrix, the method comprising; admixing an aqueous solution of a disordered protein (DP) with an aqueous solution of graphene oxide (GO), wherein the DP has an opposite charge to the GO, further wherein the graphene oxide-protein matrix is in the form of a three-dimensional (3D) structure having a lumen defined by a membrane having an inner and outer surface.

2. A graphene oxide-protein matrix comprising a disordered protein (DP) and graphene oxide (GO), wherein the DP has an opposite charge to the GO, further wherein the graphene oxide-protein matrix is in the form of a 3D structure having a lumen defined by a membrane having an inner and outer surface.

3. A kit for preparing a graphene oxide-protein matrix, the kit comprising;
 a. an aqueous solution of a disordered protein (DP)
 b. an aqueous solution of graphene oxide (GO)
wherein when the aqueous solution of DP and the aqueous solution of GO are admixed, a graphene oxide-protein matrix in the form of a 3D structure having a lumen defined by a membrane having an inner and outer surface is formed spontaneously, further wherein the DP has an opposite charge to the GO.

4. The method, graphene oxide-protein matrix, or kit of any previous clause, wherein the graphene oxide-protein matrix is prepared using a device comprising;
 (c) a reservoir containing the aqueous solution of DP; and
 (d) a nozzle in fluid connection with the reservoir of DP solution
wherein the DP solution is delivered via the nozzle to a reservoir comprising the GO.

5. The method, graphene oxide-protein matrix, or kit of any previous clause, wherein the nozzle is controlled by a computer 6. The method, graphene oxide-protein matrix, or kit of any previous clause, wherein the 3D structure is a tube.

7. The method, graphene oxide-protein matrix, or kit of any previous clause, wherein the 3D structure is selected from the group consisting of; a multi-lamella tube, a tubular network, a sphere, a cavity, a sac, a membrane or a vesicle.

8. The method, graphene oxide-protein matrix, or kit of any previous clause, wherein the internal diameter of the lumen of 3D structure is at least 10 μm.

9. The method, graphene oxide-protein matrix, or kit of any previous clause, wherein the membrane of the 3D structure is from about 5 μm to about 50 μm thick.

10. The method, graphene oxide-protein matrix, or kit of any previous clause, wherein the aqueous solution of DP is added to the aqueous solution of GO.

11. The method, graphene oxide-protein matrix, or kit of any previous clause, wherein the aqueous solution of DP is introduced to the aqueous solution of GO under pressure.

12. The method, graphene oxide-protein matrix, or kit of any previous clause, wherein the aqueous solution of DP is introduced to the aqueous solution of GO via injection, pipetting, immersion or via a drop.

13. The method, graphene oxide-protein matrix, or kit of any previous clause, wherein the aqueous solution of DP has a concentration of from about 0.2% wt/vol to about 7.5% wt/vol.

14. The method, graphene oxide-protein matrix, or kit of any previous clause, wherein the aqueous solution of GO has a concentration of from about 0.01% wt/vol to about 0.5% wt/vol.

15. The method, graphene oxide-protein matrix, or kit of any previous clause, wherein the ratio of concentration of DP solution to concentration of GO solution is at least 10:1.

16. The method, graphene oxide-protein matrix, or kit of any previous clause, wherein the pH of the DP solution is from about pH5 to about pH9.

17. The method, graphene oxide-protein matrix, or kit of any previous clause, wherein the pH of the GO solution is from about pH2 to about pH6.

18. The method, graphene oxide-protein matrix, or kit of any previous clause, wherein the 3D structure is formed at a temperature of from about 18° C. to about 75° C.

19. The method, graphene oxide-protein matrix, or kit of any previous clause, wherein the DP has a transition temperature.

20. The method, graphene oxide-protein matrix, or kit of any previous clause, wherein the 3D structure is formed at or above the transition temperature of the DP.

21. The method, graphene oxide-protein matrix, or kit of any previous clause, wherein the DP solution and GO solution is formed within 10 seconds.

22. The method, graphene oxide-protein matrix, or kit of any previous clause, wherein the DP and the GO have opposite charges.

23. The method, graphene oxide-protein matrix, or kit of any previous clause, wherein the DP is positively charged.

24. The method, graphene oxide-protein matrix, or kit of any previous clause, wherein the GO is negatively charged.

25. The method, graphene oxide-protein matrix, or kit of any previous clause, wherein the disordered protein comprises a polypeptide having a repeating amino acid sequence motif.

26. The method, graphene oxide-protein matrix, or kit of any previous clause, wherein the repeating amino acid sequence motif is comprised of from about 4 to about 30 amino acids.

27. The method, graphene oxide-protein matrix, or kit of any previous clause, wherein the repeating amino acid sequence motif is a pentamer.

28. The method, graphene oxide-protein matrix, or kit of any previous clause, wherein the disordered protein is a naturally occurring protein.

29. The method, graphene oxide-protein matrix, or kit of any previous clause, wherein the disordered protein is a synthetic protein.

30. The method, graphene oxide-protein matrix, or kit of any previous clause, wherein the disordered protein is resilin.

31. The method, graphene oxide-protein matrix, or kit of any previous clause, wherein the sequence of the DP consists of MSKGP-$(GRGDQPYQ)_n$, wherein n is greater than 5.

32. The method, graphene oxide-protein matrix, or kit of any previous clause, wherein the DP comprises an elastin-like polymer (ELP)

33. The method, graphene oxide-protein matrix, or kit of any previous clause, wherein the ELP comprises the amino acid pentamer motif $(VPGXG)_n$, wherein X is any amino acid apart from proline, and n is any number from 2 to 50.

34. The method, graphene oxide-protein matrix, or kit of any previous clause, wherein one or more of the repeating pentamers are hydrophobic.

35. The method, graphene oxide-protein matrix, or kit of any previous clause, wherein one or more of the repeating pentamers are positively charged.

36. The method, graphene oxide-protein matrix, or kit of any previous clause, wherein X in one or more of the repeating pentamers is a positively charged amino acid.

37. The method, graphene oxide-protein matrix, or kit of any previous clause, wherein X in one or more of the repeating pentamers is a hydrophobic amino acid.

38. The method, graphene oxide-protein matrix, or kit of any previous clause, wherein at least 15% of the repeating pentamers are positively charged.

39. The method, graphene oxide-protein matrix, or kit of any previous clause, wherein at least 50% of the repeating pentamers are hydrophobic.

40. The method, graphene oxide-protein matrix, or kit of any previous clause, wherein the pentamers are selected from the group consisting of; VPGIG and VPGKG.

41. The method, graphene oxide-protein matrix, or kit of any previous clause, wherein the disordered protein is ELR-IK24.

42. The method, graphene oxide-protein matrix, or kit of any previous clause, wherein the DPs have an average molecular weight of from about 15 kDa to about 55 kDa.

43. The method, graphene oxide-protein matrix, or kit of any previous clause, wherein prior to matrix assembly the DP is comprised of at least 35% random coil structure and at least 5% α-helical structure.

44. The method, graphene oxide-protein matrix, or kit of any previous clause, wherein the percentage of ß-sheet structure DP increases when complexed with GO.

45. The method, graphene oxide-protein matrix, or kit of any previous clause, wherein the lumen comprises one or more apertures.

46. The method, graphene oxide-protein matrix, or kit of any previous clause, wherein the 3D structure forms a bridge between two or more surfaces.

47. The method, graphene oxide-protein matrix, or kit of any previous clause, wherein the 3D structure comprises bifurcations.

48. The method, graphene oxide-protein matrix, or kit of any previous clause, wherein the 3D structure is biocompatible.

49. The method, graphene oxide-protein matrix, or kit of any previous clause, wherein the 3D structure is permeable.

50. The method, graphene oxide-protein matrix, or kit of any previous clause, further comprising the step of manipulating the 3D structure during formation to determine the final shape of the 3D structure.

51. The method, graphene oxide-protein matrix, or kit of any previous clause, wherein the matrix further comprises cells 52. The method, graphene oxide-protein matrix, or kit of any previous clause, wherein prior to admixing the DP and GO solutions, the method further comprises suspending cells in the DP solution.

53. The method, graphene oxide-protein matrix, or kit of any previous clause, wherein the cells are human umbilical vascular endothelial cells (hUVECs).

54. The method, graphene oxide-protein matrix, or kit of any previous clause, further comprising a step of seeding cells onto the 3D structure during or after admixing the DP and GO solutions.

55. The method, graphene oxide-protein matrix, or kit of any previous clause, further comprising a step of adding exosomes to the 3D structure prior to, during or after admixing the DP and GO solutions.

56. The method, graphene oxide-protein matrix, or kit of any previous clause, further comprising a step of adding additional structures to the 3D structure prior to, during or after admixing the DP and GO solutions.

57. The method, graphene oxide-protein matrix, or kit of any previous clause, wherein the matrix further comprises additional structures.

58. The method, graphene oxide-protein matrix, or kit of any previous clause, wherein the additional structures are selected from the group consisting of; vesicles, nanostructures, nano-capsules, growth factors, polysaccharides, exosomes, liposomes or quantum dots.

59. The method, graphene oxide-protein matrix, or kit of any previous clause, wherein the method further comprises a step of reducing the matrix by heating to reduce the GO to graphene 60. The method, graphene oxide-protein matrix, or kit of any previous clause, wherein the reduced matrix is electrically conductive.

---

The invention claimed is:

1. A graphene oxide-protein matrix comprising a disordered protein (DP) and graphene oxide (GO), wherein the DP has an opposite charge to the GO, further wherein the graphene oxide-protein matrix is in the form of a 3D structure having a lumen defined by a membrane having an inner and outer surface wherein the membrane comprises the graphene oxide protein matrix and at least partially surrounds the lumen.

2. The graphene oxide-protein matrix of claim 1, wherein the 3D structure is
   a. multilamellar
   b. a tube; or
   c. a membrane, a multi-lamella tube, a tubular network, a sphere, a cavity, a sac, or a vesicle optionally wherein the 3D structure:
   d. comprises bifurcations;
   e. is biocompatible; and/or
   f. is permeable.

3. The graphene oxide-protein matrix of claim 1, wherein;
   a. the internal diameter of the lumen of 3D structure is at least 10 pm; and/or
   b. the membrane of the 3D structure is from about 5 pm to about 50 pm thick; and/or
   c. wherein the lumen comprises one or more apertures.

4. The graphene oxide-protein matrix of claim 1, wherein the DP is positively-charged and the GO is negatively charged.

5. The graphene oxide-protein matrix of claim 1, wherein the disordered protein comprises a polypeptide having a repeating amino acid sequence motif.

6. The graphene oxide-protein matrix of claim 1, wherein the disordered protein is;
   a. Resilin, optionally comprising the sequence MSKGP-(GRGDQPYQ)n, wherein n is greater than
   b. ELR-IK24, optionally comprising the sequence MESLLP-(VPGIG VPGIG VPGKG VPGIG VPGIG)n, wherein n is greater than 5.

7. The graphene oxide-protein matrix of claim 1, wherein the DP is or comprises an elastin-like polymer (ELP), optionally wherein the ELP comprises an amino acid motif (VPGXG)n, wherein X is any amino acid apart from proline, and n is any number from 2 to 50.

8. The graphene oxide-protein matrix of claim 1, wherein the DP comprises a polymer having one or more repeating units of between 3 and 10 amino acids, optionally wherein at least 50% of the repeating units are hydrophobic.

9. The graphene oxide-protein matrix of claim 1, wherein the DP comprises a polymer having one or more repeating units of between 3 and 10 amino acids, optionally wherein at least 15% of the repeating units are positively charged.

10. The graphene oxide-protein matrix of claim 1, wherein the matrix further comprises:
   a. cells, optionally wherein the cells are human umbilical vascular endothelial cells (hUVECs);
   b. additional structures, optionally wherein the additional structures are selected from the group consisting of: vesicles, nanostructures, nano-capsules, growth factors, polysaccharides, exosomes, liposomes or quantum dots.

11. The graphene oxide-protein matrix of claim 1, wherein the GO is reduced GO.

12. A kit for preparing a graphene oxide-protein matrix, the kit comprising;
   a. an aqueous solution of a disordered protein (DP)
   b. an aqueous solution of graphene oxide (GO)
   wherein when the aqueous solution of DP and the aqueous solution of GO are admixed, a graphene oxide-protein matrix in the form of a 3D structure having a lumen defined by a membrane having an inner and outer surface wherein the membrane comprises the graphene oxide protein matrix and at least partially surrounds the lumen is formed spontaneously, further wherein the DP has an opposite charge to the GO.

13. A method of preparing a graphene oxide-protein matrix, the method comprising; admixing an aqueous solution of a disordered protein (DP) with an aqueous solution of graphene oxide (GO), wherein the DP has an opposite charge to the GO, further wherein the graphene oxide-protein matrix is in the form of a three-dimensional (3D) structure having a lumen defined by a membrane having an inner and outer surface, wherein the membrane comprises the graphene oxide protein matrix and at least partially surrounds the lumen.

14. The method of claim 13, wherein the graphene oxide-protein matrix is prepared using a device comprising;
   (a) a reservoir containing the aqueous solution of DP; and
   (b) a nozzle in fluid connection with the reservoir of DP
   wherein the DP solution is delivered via the nozzle to a reservoir comprising the GO, optionally wherein the nozzle is controlled by a computer.

15. The method of claim 13, wherein
   a. the aqueous solution of DP is added to the aqueous solution of GO; and/or
   b. prior to matrix assembly the DP is comprised of at least 35% random coil structure and at least 5% α-helical structure; and/or
   c. the percentage of β-sheet structure DP increases when complexed with GO.

16. The method of claim 13, wherein
   a. the aqueous solution of DP has a concentration of from about 0.2% wt/vol to about 7.5% wt/vol; and/or
   b. the aqueous solution of GO has a concentration of from about 0.01% wt/vol to about 0.5% wt/vol; and/or
   c. the ratio of concentration of DP solution to concentration of GO solution is at least 10:1.

17. The method of claim 13, wherein;
   a. the pH of the DP solution is from about 5 to about 9; and/or
   b. the pH of the GO solution is from about pH2 to about pH6.

18. The method of claim 13, wherein when the DP has a transition temperature, the 3D structure is formed at or above the transition temperature of the DP.

19. The method of claim 13, wherein;
   a. prior to admixing the DP and GO solutions, the method further comprises suspending cells in the DP solution; and/or
   b. further comprising a step of seeding cells onto the 3D structure during or after admixing the DP and GO solutions.

20. The method of claim 13, further comprising a step of adding additional structures to the 3D structure prior to, during or after admixing the DP and GO solutions.

* * * * *